United States Patent [19]

Winn et al.

[11] Patent Number: 5,326,776
[45] Date of Patent: Jul. 5, 1994

[54] ANGIOTENSIN II RECEPTOR ANTAGONISTS

[75] Inventors: Martin Winn, Deerfield, Ill.; Biswanath De, Cincinnati, Ohio; Thomas M. Zydowsky, Waukegan, Ill.; Daniel J. Kerkman, Lake Villa, Ill.; John F. DeBernardis, Lindenhurst, Ill.; Saul H. Rosenberg, Libertyville, Ill.; Kazumi Shiosaki, Libertyville, Ill.; Fatima Z. Basha, Lake Forest, Ill.; Kenneth P. Spina, Chicago, Ill.; Thomas W. von Geldern, Richmond, Ill.; Steven Boyd, Mundelein, Ill.; Diane M. Yamamoto, Gurnee, Ill.; Anthony K. L. Fung, Gurnee, Ill.

[73] Assignee: Abbott Laboratories, Abbott Park, Ill.

[21] Appl. No.: 21,839

[22] Filed: Feb. 24, 1993

Related U.S. Application Data

[63] Continuation-in-part of Ser. No. 844,817, Mar. 2, 1992, abandoned.

[51] Int. Cl.$^5$ .............. A61K 31/41; A61K 31/415; C07D 403/10; C07D 403/12
[52] U.S. Cl. ...................... 514/382; 514/92; 514/93; 514/94; 514/362; 514/363; 514/364; 548/112; 548/119; 548/127; 548/128; 548/130; 548/131; 548/132; 548/133; 548/134; 548/135; 548/138; 548/142; 548/143; 548/251; 548/252; 548/253; 548/254
[58] Field of Search .............. 514/382, 362, 363, 364; 548/127, 128, 131, 134, 135, 143, 252, 254

[56] References Cited

U.S. PATENT DOCUMENTS

| | | | |
|---|---|---|---|
| 5,015,651 | 5/1991 | Carini et al. | 514/381 |
| 5,043,349 | 8/1991 | Carini et al. | 514/427 |
| 5,081,127 | 1/1992 | Carini et al. | 514/359 |
| 5,137,902 | 8/1992 | Carini et al. | 514/381 |
| 5,138,069 | 8/1992 | Carini et al. | 514/253 |
| 5,189,048 | 2/1993 | Carini et al. | 514/359 |

FOREIGN PATENT DOCUMENTS

| | | |
|---|---|---|
| 9180163 | 1/1992 | Australia . |
| 323841 | 7/1989 | European Pat. Off. . |
| 409332 | 1/1991 | European Pat. Off. . |
| 412594 | 2/1991 | European Pat. Off. . |
| 454511 | 10/1991 | European Pat. Off. . |
| 505098 | 9/1992 | European Pat. Off. . |
| WO91/14367 | 10/1991 | PCT Int'l Appl. . |
| WO91/15479 | 10/1991 | PCT Int'l Appl. . |
| WO91/00277 | 1/1992 | PCT Int'l Appl. . |
| WO92/00977 | 1/1992 | PCT Int'l Appl. . |
| WO92/21666 | 12/1992 | PCT Int'l Appl. . |

Primary Examiner—Mary C. Lee
Assistant Examiner—Jacqueline Haley
Attorney, Agent, or Firm—Steven R. Crowley

[57] ABSTRACT

Compounds are disclosed having the formula:

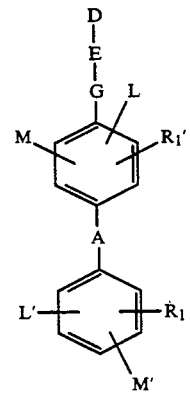

wherein the substituents are defined herein. The compounds of the invention are angiotensin II receptor antagonists.

26 Claims, No Drawings

ANGIOTENSIN II RECEPTOR ANTAGONISTS

This is a continuation-in-part of U.S. patent application Ser. No. 844,817, filed Mar. 2, 1992, now abandoned.

TECHNICAL FIELD

This invention relates to compounds and compositions which block angiotensin II receptors, processes for making such compounds, synthetic intermediates employed in these processes and a method of treating hypertension, edema, renal failure, benign prostatic hypertrophy, diabetic nephropathy, diabetic retinopathy, Alzheimer's disease or congestive heart failure with such compounds. The present invention also relates to compositions and a method for treating glaucoma, preventing or treating atherosclerosis, preventing or treating stroke and treatment of a variety of obesity-related disorders with such compounds. The present invention also relates to compositions and a method for treating CNS disorders.

BACKGROUND OF THE INVENTION

Blood pressure is regulated by a multitude of interrelated factors involving neural, vascular and volume-related effects. The renin-angiotensin system (RAS) is one of the important blood pressure regulating systems.

The RAS functions as shown in the scheme below. Low renal perfusion pressure stimulates the juxtaglomerular cells of the kidney to produce the proteolytic enzyme renin. This enzyme acts on a circulating protein, angiotensinogen, cleaving off a decapeptide angiotensin I. Angiotensin I is then cleaved to the octapeptide angiotensin II by angiotensin converting enzyme (ACE). Angiotensin II is the most powerful pressor substance in the RAS. Angiotensin II binds to vascular smooth muscle receptors and induces vasoconstriction, but has little or no stimulating action on the heart.

Peptidyl and non-peptidyl angiotensin II receptor antagonists are known. The peptidyl compound saralasin or [Sar[1],Ala[8]] angiotensin II has been found to be a potent antagonist of the actions of angiotensin II. Saralasin, however, has several disadvantages. Because it is a peptide, saralasin has very poor oral bioavailability. The use of saralasin, therefore, is limited to administration to hospitalized patients by continuous intravenous infusion. Saralasin is also known to cause an initial increase in blood pressure after intravenous administration due to its activity as an angiotensin receptor agonist. Therefore, non-peptidyl angiotensin II receptor antagonists are preferred.

DISCLOSURE OF THE INVENTION

In accordance with the present invention, there are compounds of the formula (I):

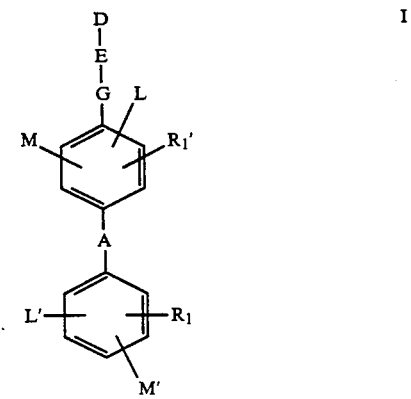

wherein
A is
(i) a covalent bond,
(ii) —O—,
(iii) —C(O)—,

Renin-Angiotensin System

Human
Angiotensinogen: H$_2$N—Asp—Arg—Val—Tyr—Ile—His—Pro—Phe—His—<u>Leu—Val</u>—Ile—His—
Protein Sequence ID No. 1

↓ Renin

Angiotensin I: H$_2$N—Asp—Arg—Val—Tyr—Ile—His—Pro—<u>Phe—His</u>—Leu—OH
Sequence ID No. 2

↓ ACE

Angiotensin II: H$_2$N—<u>Asp—Arg</u>—Val—Tyr—Ile—His—Pro—Phe—OH
Sequence ID No. 3

↓ Aminopeptidase

Angiotensin III: H$_2$N—Arg—Val—Tyr—Ile—His—Pro—Phe—OH
Sequence ID No. 4

↓ Angiotensinases

Inactive Fragments

Inhibitors of renin (for example enalkiren) and inhibitors of ACE (for example, captopril and enalapril) have clinical efficacy in treating hypertension and congestive heart failure. ACE inhibitors, however, have reported side effects including cough and skin rash.

(iv) —CH$_2$—,
(v) —S—, —S(O)— or —S(O)$_2$—;
E—G is
(i) —N(R$_5$)—,
(ii) —O—, (iii) —S—,
(iv) —N(R$_5$)—CH(R$_5$)—,
(v) —O—CH(R$_5$)—,
(vi) —S—CH(R$_5$)—,
(vii) —C(R$_5$')(R$_5$)—CH(R$_5$)—,
(viii) —CH(R$_5$)—C(R$_5$')(R$_5$)—,
(ix) —CH(R$_5$)—N(R$_5$)—,
(x) —CH(R$_5$)—O—,
(xi) —CH(R$_5$)—S—,
(xii) —N(R$_5$)—N(R$_5$)—,
(xiii) —C(R$_5$)=C(R$_5$)— or
(xiv) —CH(R$_5$)—C(R$_5$')(R$_5$)—N(R$_5$)— wherein at each occurrence R$_5$ is independently selected from hydrogen, loweralkyl, alkoxy-substituted loweralkyl, halo-substituted loweralkyl, carboxy-substituted loweralkyl, heterocyclic-substituted loweralkyl, alkenyl, alkynyl, cycloalkyl or cycloalkylalkyl and R$_5$' is hydrogen, halo, hydroxy, carboxy, alkoxy or thioalkoxy;

L, L', M and M' are independently selected from
(i) hydrogen,
(ii) loweralkyl,
(iii) halo-substituted loweralkyl,
(iv) halo,
(v) —CN,
(vi) —NO$_2$,
(vii) —OH,
(viii) hydroxy-substituted loweralkyl,
(ix) alkoxy-substituted loweralkyl,
(x) —NH$_2$,
(xi) alkylamino,
(xii) dialkylamino,
(xiii) —SH,
(xiv) alkoxy and
(xv) thioalkoxy;

R$_1$ and R$_1$' are independently selected from
(i) tetrazolyl,

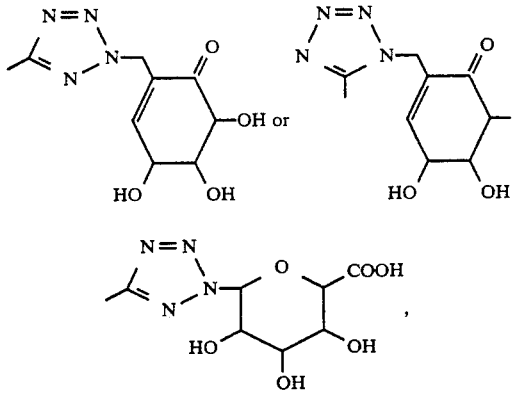

(iv) —NH—C(=N(R$_{50a}$))(R$_{51a}$) wherein R$_{50a}$ is hydrogen, —CN or —NO$_2$ and R$_{51a}$ is hydrogen, loweralkyl, alkylamino, dialkylamino, alkoxy or thioalkoxy,
(v) —NH(R$_{51b}$) wherein R$_{51b}$ is a 5-membered aromatic heterocyclic ring wherein the heterocyclic ring contains 1, 2, 3 or 4 nitrogen atoms or 1 nitrogen atom and 1 oxygen atom or 2 nitrogen atoms and 1 oxygen atom or 1 oxygen atom and 1 sulfur atom and wherein the 5-membered heterocyclic ring is unsubstituted or substituted with a substituent selected from amino, alkylamino, dialkylamino, hydroxy, alkoxy, thioalkoxy, halo, loweralkyl and halo-substituted loweralkyl,
(vi) —COOR$_6$ or —CH$_2$COOR$_6$ wherein R$_6$ is hydrogen or a carboxy-protecting group or
(vii) —NHS(O)$_2$R$_7$ or —CH$_2$NHS(O)$_2$R$_7$ or —NHC(O)R$_{7a}$ or —CH$_2$NHC(O)R$_{7a}$ wherein R$_7$ is loweralkyl, halo-substituted loweralkyl or —NR$_{7b}$R$_{7c}$ wherein R$_{7b}$ and R$_{7c}$ are independently selected from hydrogen and loweralkyl and R$_{7a}$ is loweralkyl, halo-substituted loweralkyl, amino, alkylamino, dialkylamino or —COOH;
(viii) —C(O)NR$_{50}$R$_{51}$ or —CH$_2$C(O)NR$_{50}$R$_{51}$ or —NHC(O)NR$_{50}$R$_{51}$ or —CH$_2$NHC(O)NR$_{50}$R$_{51}$ or —NHC(S)NR$_{50}$R$_{51}$ or —CH$_2$NHC(S)NR$_{50}$R$_{51}$ wherein R$_{50}$ and R$_{51}$ are independently selected from hydrogen, loweralkyl, hydroxy, alkoxy, hydroxy-substituted loweralkyl, alkoxy-substituted loweralkyl, alkoxy-substituted alkoxy and —S(O)$_2$R$_{50a}$ wherein R$_{50a}$ is loweralkyl or aryl, or R$_{50}$ and R$_{51}$ taken together with the nitrogen atom to which they are attached form a 5-to 7-membered aliphatic heterocycle;
(ix) —CH$_2$OR$_{52}$ wherein R$_{52}$ is selected from hydrogen, loweralkyl and —C(O)R$_{53}$ wherein R$_{53}$ is hydrogen, loweralkyl or aryl;
(x) —CH(OH)R$_{52a}$ or —C(O)R$_{52a}$ wherein R$_{52a}$ is loweralkyl, halo-substituted loweralkyl, —CF$_2$COOR$_{53a}$ or —CH$_2$COOR$_{53a}$ wherein R$_{53a}$ is hydrogen or a carboxy-protecting group,
(xii) —CH$_2$NR$_{54}$R$_{55}$ wherein R$_{54}$ is selected from hydrogen, loweralkyl, —C(O)R$_{56}$, —C(O)NR$_{56}$R$_{57}$ and —S(O)$_2$R$_{58}$ wherein R$_{56}$ is selected from hydrogen, loweralkyl and aryl and R$_{58}$ is selected from lower alkyl and halo-substituted loweralkyl and wherein R$_{55}$ and R$_{57}$ are independently selected from hydrogen, loweralkyl, hydroxy and alkoxy;
(xiii) —SO$_3$H, —OSO$_3$H or —CH$_2$SO$_3$H,
(xiv) —OPO$_3$H$_2$, —PO$_3$H$_2$ or —CH$_2$PO$_3$H$_2$,
(xv) —SO$_2$NR$_{50}$R$_{51}$ or —CH$_2$SO$_2$NR$_{50}$R$_{51}$ wherein R$_{50}$ and R$_{51}$ are defined as above and
(xvi) —C(O)NHSO$_2$R$_{60}$, —C(O)NHC(O)R$_{60}$ or —C(O)NHNHSO$_2$R$_{60}$ wherein R$_{60}$ is loweralkyl, halo-substituted loweralkyl or aryl; and (xvii) hydrogen; with the proviso that one of R$_1$ and R$_1$' is hydrogen, but R$_1$ and R$_1$' are not both hydrogen; and D is a 5-membered heterocyclic ring comprising 1, 2, 3 or 4 nitrogen atoms or 2 nitrogen atoms and 1 oxygen atom or 2 nitrogen atoms and 1 sulfur atom or 1 nitrogen atom and 1 sulfur atom or 1 nitrogen atom and 1 oxygen atom or 1 sulfur atom and 1 oxygen atom or 1 oxygen atom or 1 sulfur atom, the remaining ring atoms being carbon atoms and the 5-membered heterocyclic ring comprising 0, 1 or 2 double bonds; the nitrogen atoms of the 5-membered heterocyclic ring can be substituted with a substitutent R$_2$ wherein at each occurrence R$_2$ is independently selected from hydrogen, loweralkyl, carboxy-substituted loweralkyl or alkoxycarbonyl-substituted loweralkyl; one or two carbon atoms of the 5-membered heterocyclic ring can also be substituted with an oxo (=O) substituent and the sulfur atoms of the 5-membered heterocyclic ring can be substituted with one or two oxo (=O) substituents; the nitrogen atoms of the 5-membered heterocyclic ring can be oxidized; the 5-membered heterocyclic ring can also be substituted with one or two substitutents independently selected from R$_3$ and R$_4$, R$_3$ being bonded to a carbon atom or a nitrogen atom of the 5-membered heterocyclic ring and $R_4$ being bonded to a carbon atom or a nitrogen atom of the 5-membered heterocyclic ring, wherein $R_3$ is (i) hydrogen,
(ii) loweralkyl,
(iii) halo,
(iv) halo-substituted loweralkyl,
(v) thioalkoxy,
(vi) alkoxy-substituted loweralkyl,
(vii) thioalkoxy-substituted loweralkyl,
(viii) aryl,
(ix) arylalkyl,
(x) —$NO_2$,
(xi) —$COOR_8$ wherein $R_8$ is hydrogen or a carboxy-protecting group,
(xii) —$OR_9$ wherein $R_9$ is hydrogen, loweralkyl, halo-substituted loweralkyl, aryl, arylalkyl, heterocyclic-substituted loweralkyl or —$C(O)R_{10}$ wherein $R_{10}$ is loweralkyl, halo- substituted loweralkyl, —$PO_3H_2$ or —$NR_{11}R_{12}$ wherein $R_{11}$ and $R_{12}$ are independently selected from hydrogen and loweralkyl and
(xiii) —$NR_{13}R_{14}$ or —$CH_2NR_{13}R_{14}$ wherein $R_{13}$ and $R_{14}$ are independently selected from (1) hydrogen, (2) lower alkyl, (3) arylalkyl, (4) —$C(O)R_{15}$, (5) —$S(O)_2R_{15}$ wherein $R_5$ is loweralkyl or halo- substituted loweralkyl and (6) —$R_{16}$—$R_{17}$ wherein $R_{16}$ is alkylene and $R_{17}$ is (a) —$NR_{18}R_{19}$ wherein $R_{18}$ and $R_{19}$ are independently selected from hydrogen and loweralkyl or (b) unsubstituted or loweralkyl substituted aziridinyl, azetidinyl, pyrrolidinyl, piperidinyl, piperazinyl, morpholinyl, thiomorpholinyl, pyridinyl or pyrimidinyl, or $R_{13}$ and $R_{14}$ taken together with the nitrogen atom to which they are attached form a 5-to 7-membered aliphatic heterocycle and $R_4$ is (i) hydrogen,
(ii) loweralkyl,
(iii) halo-substituted loweralkyl,
(iv) —CN,
(v) —$NO_2$,
(vi) —$NH_2$,
(vii) —NH—C(=N($R_{25a}$))($R_{26a}$) wherein $R_{25a}$ is hydrogen, —CN or —$NO_2$ and $R_{26a}$ is hydrogen, loweralkyl, alkylamino, dialkylamino, alkoxy or thioalkoxy,
(viii) —NH($R_{26b}$) wherein $R_{26b}$ is a 5-membered aromatic heterocyclic ring wherein the heterocyclic ring contains 1, 2, 3 or 4 nitrogen atoms or 1 nitrogen atom and 1 oxygen atom or 2 nitrogen atoms and 1 oxygen atom or 1 oxygen atom and 1 sulfur atom and wherein the 5-membered heterocyclic ring is unsubstituted or substituted with a substituent selected from amino, alkylamino, dialkylamino, hydroxy, alkoxy, thioalkoxy, halo, loweralkyl and halo-substituted loweralkyl,
(ix) —CHO or —CH(=N—OH),
(x) tetrazolyl,
(xi) —$NHS(O)_2R_{20}$ or —$CH_2NHS(O)_2R_{20}$ or —NHC(O)$R_{21}$ or —N(OH)C(O)$R_{21}$ or —$CH_2NHC(O)R_{21}$ or —$CH_2N(OH)C(O)R_{21}$ wherein $R_{20}$ is loweralkyl, halo- substituted loweralkyl or —$NR_{27a}R_{27b}$ wherein $R_{27a}$ and $R_{27b}$ are independently selected from hydrogen, —OH and loweralkyl and $R_{21}$ is loweralkyl, halo-substituted loweralkyl, amino, alkylamino, dialkylamino or —COOH, (xii) —CH(OH)$R_{22}$ or —C(O)$R_{22}$ wherein $R_{22}$ is loweralkyl, halo-substituted loweralkyl, —$CF_2COOR_{23}$ or —$CH_2COOR_{23}$ wherein $R_{23}$ is hydrogen or a carboxy-protecting group,
(xiii) —$COOR_{24}$ or —$CH_2COOR_{24}$ wherein $R_{24}$ is hydrogen or a carboxy-protecting group,
(xiv) —$C(O)NR_{25}R_{26}$ or —$CH_2C(O)NR_{25}R_{26}$ or —$NHC(O)NR_{25}R_{26}$ or —$CH_2NHC(O)NR_{25}R_{26}$ or —$NHC(S)NR_{25}R_{26}$ or —$CH_2NHC(S)NR_{25}R_{26}$ wherein $R_{25}$ and $R_{26}$ are independently selected from hydrogen, loweralkyl, hydroxy, alkoxy, hydroxy-substituted loweralkyl, alkoxy-substituted loweralkyl, alkoxy-substituted alkoxy and —$S(O)_2R_{28a}$ wherein $R_{28a}$ is loweralkyl or aryl, or $R_{25}$ and $R_{26}$ taken together with the nitrogen atom to which they are attached form a 5-to 7-membered aliphatic heterocycle;
(xv) —$CH_2OR_{27}$ wherein $R_{27}$ is selected from hydrogen, loweralkyl and —$C(O)R_{28}$ wherein $R_{28}$ is hydrogen, loweralkyl or aryl;
(xvi) —$CH_2NR_{29}R_{30}$ wherein $R_{29}$ is selected from hydrogen, loweralkyl, —$C(O)R_{31}$, —$C(O)NR_{31}R_{32}$ and —$S(O)_2R_{33}$ wherein $R_{31}$ is selected from hydrogen, loweralkyl and aryl and $R_{33}$ is selected from loweralkyl and halo-substituted loweralkyl and wherein $R_{30}$ and $R_{32}$ are independently selected from hydrogen, loweralkyl, hydroxy and alkoxy;
(xvii) —$SO_3H$, —$OSO_3H$ or —$CH_2SO_3H$,
(xviii) —$OPO_3H$, —$PO_3H_2$ or —$CH_2PO_3H_2$,
(xix) —$SO_2NR_{25}R_{26}$ or —$CH_2SO_2NR_{25}R_{26}$ wherein $R_{25}$ and $R_{26}$ are defined as above and
(xx) —$C(O)NHSO_2R_{59}$, —$C(O)NHC(O)R_{59}$ or —$C(O)NHNHSO_2R_{59}$ wherein $R_{59}$ is loweralkyl, halo-substituted loweralkyl or aryl;

or a pharmaceutically acceptable salt or prodrug thereof.

Preferred compounds of the invention are compounds wherein D is a substituted imidazolyl group, a substituted thiazolyl group, a substituted oxazolyl group, a substituted thiadiazolyl group, a substituted pyrazolyl group, a substituted isoxazolyl group, a substituted isothiazolyl group, a substituted thienyl group, a substituted oxadiazolyl group, a substituted triazolyl group or a substituted pyrrolidinyl group.

Preferred compounds of the invention are compounds wherein A is a covalent bond, E—G is —N($R_5$)—$CH_2$—, $R_1'$ is hydrogen and $R_1$ is tetrazolyl.

More preferred compounds of the invention are compounds wherein D is

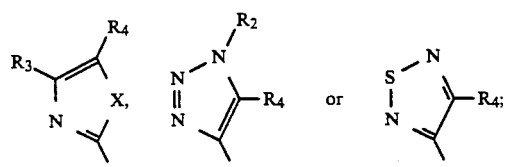

wherein X is NH, O or S; A is a covalent bond; E—G is —N($R_5$)—$CH_2$—, $R_1'$ is hydrogen and $R_1$ is tetrazolyl.

Even more preferred compounds of the invention are compounds wherein D is

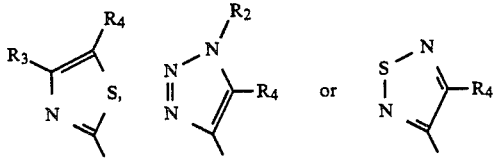
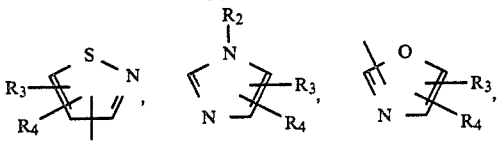
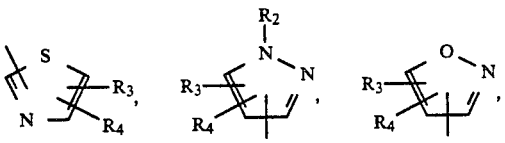

wherein R2 is hydrogen or loweralkyl; R3 is hydrogen, loweralkyl or halo-substituted loweralkyl; R4 is —COOR24 wherein R24 is hydrogen or a carboxy-protecting group; A is a covalent bond; E—G is —N(R5)—CH2— wherein R5 is hydrogen, loweralkyl, cycloalkyl, cycloalkylalkyl, alkenyl or alkynyl; R1' is hydrogen; R1 is tetrazolyl; and L, L', M and M' are independently selected from hydrogen, loweralkyl, halo, halo-substituted loweralkyl, —OH and alkoxy.

Representative 5-membered heterocyclic rings are:

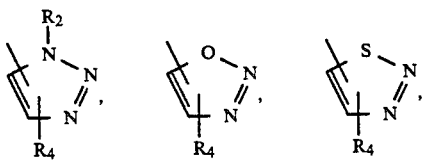
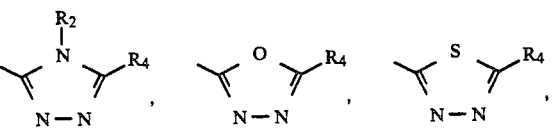
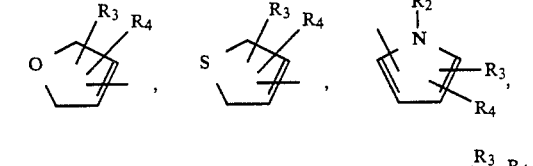
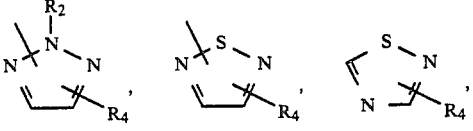
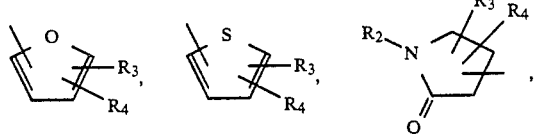
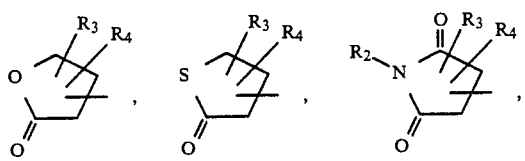
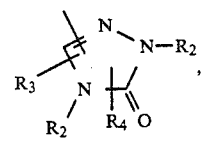
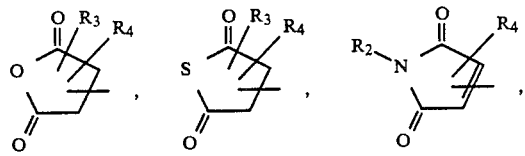
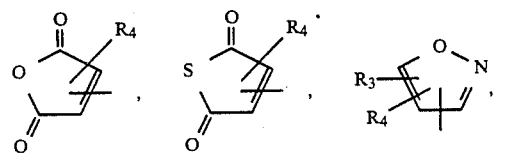
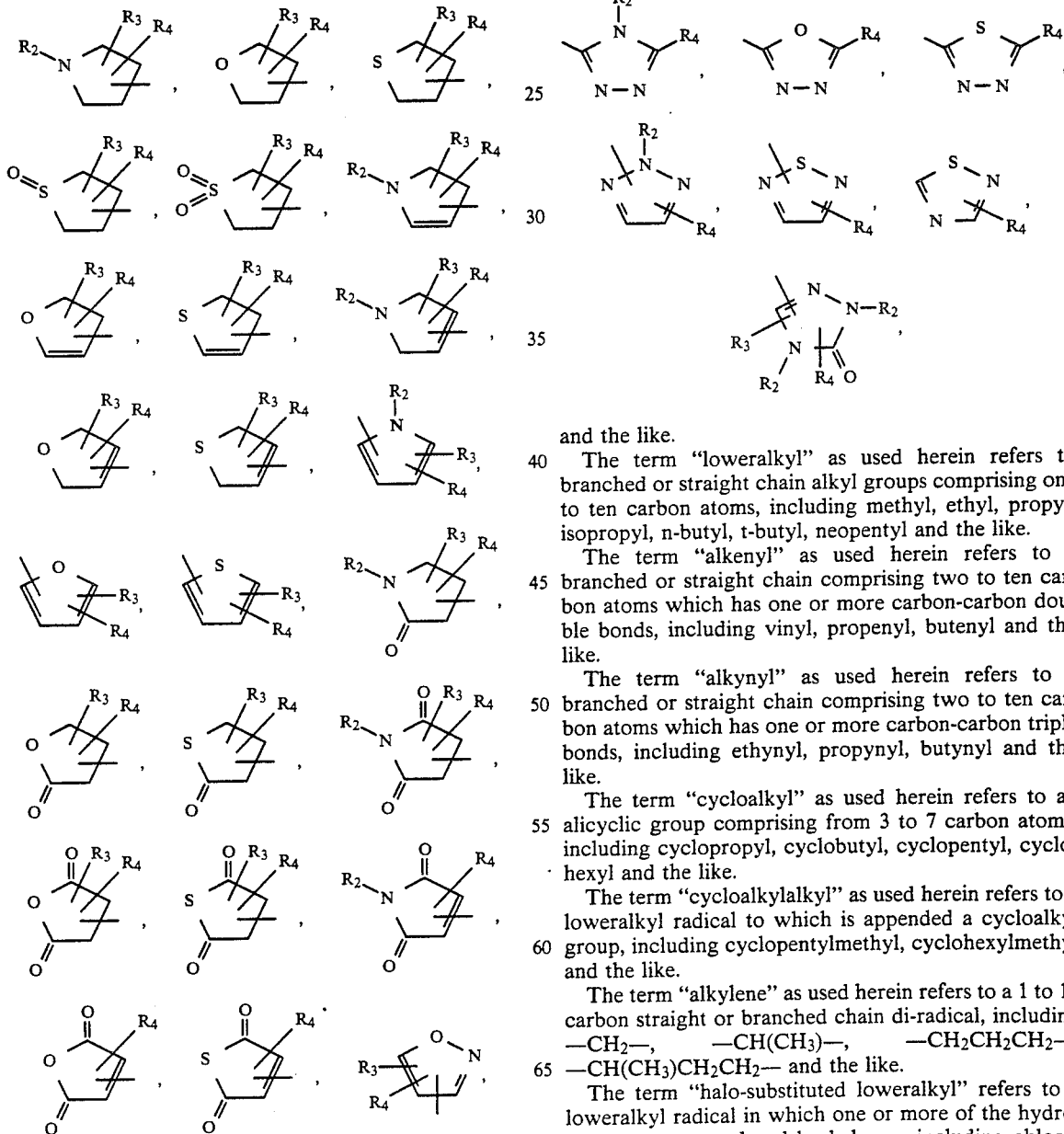

and the like.

The term "loweralkyl" as used herein refers to branched or straight chain alkyl groups comprising one to ten carbon atoms, including methyl, ethyl, propyl, isopropyl, n-butyl, t-butyl, neopentyl and the like.

The term "alkenyl" as used herein refers to a branched or straight chain comprising two to ten carbon atoms which has one or more carbon-carbon double bonds, including vinyl, propenyl, butenyl and the like.

The term "alkynyl" as used herein refers to a branched or straight chain comprising two to ten carbon atoms which has one or more carbon-carbon triple bonds, including ethynyl, propynyl, butynyl and the like.

The term "cycloalkyl" as used herein refers to an alicyclic group comprising from 3 to 7 carbon atoms, including cyclopropyl, cyclobutyl, cyclopentyl, cyclohexyl and the like.

The term "cycloalkylalkyl" as used herein refers to a loweralkyl radical to which is appended a cycloalkyl group, including cyclopentylmethyl, cyclohexylmethyl and the like.

The term "alkylene" as used herein refers to a 1 to 10 carbon straight or branched chain di-radical, including —CH2—, —CH(CH3)—, —CH2CH2CH2—, —CH(CH3)CH2CH2— and the like.

The term "halo-substituted loweralkyl" refers to a loweralkyl radical in which one or more of the hydrogen atoms are replaced by halogen, including chloro-methyl, fluoroethyl, trifluoromethyl, pentafluoroethyl and the like.

The term "hydroxy-substituted loweralkyl" refers to a loweralkyl radical to which is appended one or two hydroxy (—OH) groups.

The term "halogen" or "halo" as used herein refers to I, Br, Cl or F.

The term "alkoxy" refers to $R_{34}O-$ wherein $R_{34}$ is a loweralkyl or benzyl group. Representative examples of alkoxy groups include methoxy, ethoxy, t-butoxy, benzyloxy and the like.

The term "thioalkoxy" as used herein refers to $R_{35}S-$ wherein $R_{35}$ is a loweralkyl or benzyl group.

The term "alkoxy-substituted loweralkyl" as used herein refers to a loweralkyl radical to which is appended an alkoxy group.

The term "thioalkoxy-substituted loweralkyl" as used herein refers to a a loweralkyl radical to which is appended a thioalkoxy group. Representative thioalkoxy-substituted loweralkyl groups include methylthiomethyl, methylthioethyl, ethylthioethyl, propylthiomethyl and the like.

The term "hydroxy-substituted loweralkyl" as used herein refers to a loweralkyl radical to which is appended one or two hydroxy (—OH) groups.

The term "carboxy-substituted loweralkyl" as used herein refers to a loweralkyl radical to which is appended a carboxy group (—COOH), including carboxymethyl, carboxyethyl and the like.

The term "alkoxycarbonyl" as used herein refers to $-C(O)OR_{36}$ wherein $R_{36}$ is a carboxy-protecting group.

The term "alkoxycarbonyl-substituted loweralkyl" as used herein refers to a loweralkyl radical to which is appended an alkoxycarbonyl group.

The term "alkoxy-substituted alkoxy" as used here refers to an alkoxy radical to which is appended another alkoxy radical, including methoxymethoxy, methoxy ethoxy, ethoxyethoxy and the like.

The term "alkylamino" as used herein refers to $-NHR_{37}$ wherein $R_{37}$ is a loweralkyl group.

The term "dialkylamino" as used herein refers to $-NR_{38}R_{39}$ wherein $R_{38}$ and $R_{39}$ are independently selected from loweralkyl.

The term "alkanoyloxyalkyl" as used herein refers to a loweralkyl radical to which is appended $-OC(O)R_{40}$ wherein $R_{40}$ is loweralkyl.

The term "aroyloxyalkyl" as used herein refers to a loweralkyl radical to which is appended $-OC(O)R_{41}$ wherein $R_{41}$ is aryl.

The term "alkoxycarbonylalkyl" as used herein refers to a loweralkyl radical to which is appended an alkoxycarbonyl group.

The term "alkoxycarbonyloxyalkyl" as used herein refers to a loweralkyl radical to which is appended $-OC(O)OR_{42}$ wherein $R_{42}$ is loweralkyl or cycloalkyl.

The term "alkoxycarbonylaminoalkyl" as used herein refers to a loweralkyl radical to which is appended $-NHC(O)OR_{43}$ wherein $R_{43}$ is loweralkyl.

The term "alkylaminocarbonylaminoalkyl" as used herein refers to a loweralkyl radical to which is appended $-NHC(O)NHR_{44}$ wherein $R_{44}$ is loweralkyl.

The term "alkanoylaminoalkyl" as used herein refers to a loweralkyl radical to which is appended $-NHC(O)R_{45}$ wherein $R_{45}$ is loweralkyl.

The term "heterocycliccarbonyloxyalkyl" as used herein refers to a loweralkyl radical to which is appended $-OC(O)R_{46}$ wherein $R_{46}$ is a heterocyclic group.

The term "aryl" as used herein refers to a phenyl or a $C_9$ or $C_{10}$ bicyclic carbocyclic ring system having one or more aromatic rings, including naphthyl, tetrahydronaphthyl, indanyl, indenyl and the like. Aryl groups can be unsubstituted or substituted with one, two or three substituents independently selected from loweralkyl, halo-substituted loweralkyl, alkoxy, thioalkoxy, alkoxycarbonyl, hydroxy, halo, mercapto, nitro, amino, alkylamino, dialkylamino, carboxaldehyde, carboxy and carboxamide.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "aliphatic heterocycle" as used herein refers to a saturated cyclic group containing 5 to 7 ring atoms and, in particular, at least 1 nitrogen atom in the ring and optionally 1 additional heteroatom selected from S, $S(O)_2$, O and N, with the remaining ring atoms being carbon atoms. The ring can be substituted on a carbon atom or a heteroatom, for example, with loweralkyl, alkoxy or alkoxy-substituted alkoxy. Representative aliphatic heterocycles include, pyrrolidine, piperidine, piperazine, morpholine, thiomorpholine, S,S-dioxothiomorpholine, 4-methoxymethoxypiperidine and the like.

The term "heterocyclic group" or "heterocyclic" as used herein refers to any 3- or 4-membered ring containing a heteroatom selected from oxygen, nitrogen and sulfur, or a 5-, 6- or 7-membered ring containing one, two or three nitrogen atoms; one nitrogen and one sulfur atom; or one nitrogen and one oxygen atom; wherein the 5-membered ring has 0-2 double bonds and the 6- or 7-membered ring has 0-3 double bonds; wherein the nitrogen and sulfur heteroatoms can optionally be oxidized; wherein the nitrogen heteroatom can optionally be quaternized; and including any bicyclic group in which any of the above heterocyclic rings is fused to a benzene ring or another 5-, 6- or 7-membered heterocyclic ring independently as defined above. Heterocyclics include indolyl, quinolyl, isoquinolyl, tetrahydroquinolyl, benzofuryl, benzothienyl, azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazoiyl, isothiazolidinyl, indolyl, quinolinyl, isoquinolinyl, benzimidazolyl, benzothiazolyl, benzoxazolyl, furyl, thienyl, triazolyl, benzothienyl, homopiperazinyl, homopiperidinyl, homomorpholinyl and the like.

Heterocyclics can be unsubstituted or monosubstituted or disubstituted with substitutents independently selected from hydroxy, halo, oxo (=O), amino, alkylamino, dialkylamino, alkoxy, thioalkoxy, carboxy, alkoxycarbonyl, loweralkyl, cycloalkyl, $-OSO_3H$ and halo-substituted loweralkyl.

The term "heterocyclic-substituted loweralkyl" as used herein refers to a loweralkyl radical to which is appended a heterocyclic group.

The term "N-protecting group" or "N-protected" as used herein refers to those groups intended to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, t-butyloxycarbonyl (Boc), benzyloxycarbonyl (Cbz) and the like.

As used herein, the term "carboxy-protecting group" refers to a carboxy group which has been esterified with one of the commonly used carboxylic acid protecting ester groups employed to block or protect the carboxylic acid functionality while the reactions involving other functional sites of the compound are carried out. Carboxy-protecting groups are disclosed in Greene, "Protective Groups in Organic Synthesis" pp. 152–186 (1981), which is incorporated herein by reference. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975). Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. Examples of esters useful as prodrugs for compounds containing carboxyl groups can be found on pages 14-21 of "Bioreversible Carriers in Drug Design: Theory and Application", edited by E. B. Roche, Pergamon Press: New York (1987). Representative carboxy-protecting groups are $C_1$ to $C_8$ alkyl (e.g., methyl, ethyl or tertiary butyl and the like), benzyl and substituted derivatives thereof such as alkoxybenzyl or nitrobenzyl groups and the like, dialkylaminoalkyl (e.g., dimethylaminoethyl and the like), alkanoyloxyalkyl groups such as pivaloyloxymethyl or propionyloxymethyl and the like, aroyloxyalkyl, such as benzoyloxyethyl and the like, alkoxycarbonylalkyl, such as methoxycarbonylmethyl, cyclohexyloxycarbonylmethyl and the like, alkoxycarbonyloxyalkyl, such as t-buyloxycarbonyloxymethyl and the like, alkoxycarbonylaminoalkyl, such as t-butyloxycarbonylaminomethyl and the like, alkylaminocarbonylaminoalkyl, such as methylaminocarbonylaminomethyl and the like, alkanoylaminoalkyl, such as acetylaminomethyl and the like, heterocycliccarbonyloxyalkyl, such as 4-methylpiperazinylcarbonyloxymethyl and the like, dialkylaminocarbonylalkyl, such as dimethylaminocarbonylmethyl and the like, (5-(loweralkyl)-2-oxo-1,3-dioxolen-4-yl)alkyl, such as (5-t-butyl-2-oxo-1,3-dioxolen-4-yl)methyl and the like and (5-phenyl-2-oxo-1,3-dioxolen-4-yl)alkyl, such as (5-phenyl-2-oxo-1,3-dioxolen-4-yl)methyl and the like.

When the compounds of formula I contain one asymmetric carbon atom, they can exist as pure enantiomers or mixtures of enantiomers. When the compounds of formula I contain more than one asymmetric carbon atom, they can exist as diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem (1976) 45, 13–30.

In addition, in the compounds of the invention, combinations of substituents and/or variables (i.e., A, D, E, G, $R_1$, $R_2$, $R_3$, $R_4$, etc.) are permissible only if such combinations result in stable compounds.

In general, the compounds of this invention can be prepared by the processes illustrated in Schemes I through XXXII. It should be understood that substituents A, D, E, G, $R_1$, $R_2$, $R_3$, $R_4$, etc. as used herein correspond to the groups identified by formula (I). P is a protecting group. In the course of synthesis, certain groups present in the molecule, particulary carboxylic acid and tetrazole groups, are protected and deprotected as necessary. The term "protecting group" is well known in the art and refers to substituents on functional groups of compounds undergoing chemical transformation which prevent undesired reactions and degradations during a synthesis; see, for example, T. H. Greene, "Protective Groups in Organic Synthesis", John Wiley & Sons, New York (1981) for methods of introducing and removing appropriate protecting groups. Suitable carboxy-protecting groups include t-butyl and benzyl groups. Suitable tetrazole nitrogen-protecting groups include triphenylmethyl (Tr), benzyl, t-butyl, methoxymethyl, benzyloxymethyl, p-nitrobenzyl, 1-ethoxyethyl and the like.

The compounds of formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformation proposed. This will frequently necessitate judgment as to the order of synthetic steps, protecting groups required and deprotection conditions. Throughout the following section, not all compounds of formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

Schemes I–XV illustrate methods of preparing compounds of the invention comprising various —G—E— substitutents.

Scheme I

Reaction Scheme I illustrates a method of preparing compounds wherein —G—E— is —N(R$_5$)—. According Scheme XVIII, a biphenylamine of Formula 82 is alkylated under standard conditions (e.g., R$_5$—X′ wherein X′ is a leaving group) and then reacted with a chloro-heterocycle to give a compound of Formula 81.

Scheme II

According to Scheme II, compounds wherein —G—E— is —O— are prepared by coupling a hydroxy-substituted heterocycle with a bromo-biphenyl compound of Formula 80 in the presence of a copper salt to give a compound of Formula 83.

Scheme III

Reaction Scheme III illustrates a method of preparing compounds wherein —G—E— is —S—. According to Scheme XX, a biphenyl thiol of Formula 85 is reacted with a chloro-heterocycle to give a compound of Formula 84.

Scheme IV

Reaction Schemes IVA and IVB illustrate alternative methods of preparing compounds wherein —G—E— is —$CH_2$—N($R_5$)—. According to Scheme IVA, a biphenylmethylamine of the Formula 86 is reacted with a chloroheterocycle in the presence of a base, such as triethylamine or lithium hexamethyldisilazide, to give a compound of Formula 87. Alternatively, according to Scheme IVB, a chloro-heterocycle is reacted with a primary amine to give a compound of Formula 88. This secondary amine is reacted with a biphenylmethyl bromide 89 to give a compound of Formula 87.

Scheme V

According to Scheme V, compounds wherein —G—E— is —CH($R_5$)—NH— are prepared by oxidizing a compound of Formula 90 to aldehyde 91. Addition of an organometallic reagent (e.g., $R_5$—M is propyl-Grignard reagent, yields secondary alcohol 92. The alcohol is converted to a leaving group (e.g., X' is a mesylate) which is displaced with a heterocyclic amine to afford a compound of Formula 94.

Scheme VI

Reaction Schemes VIA and VIB illustrate alternative methods of preparing compounds wherein —G—E— is —CH($R_5$)—O—. According to Scheme VIA, a compound of Formula 93 having a leaving group X', e.g., mesylate, is reacted with a hydroxy-substituted heterocyclic in the presence of a base to give a compound of Formula 95. Alternatively, according to Scheme VIB, secondary alcohol 92, whose preparation is illustrated in Scheme XXII, is reacted with a chloro-heterocycle in the presence of a base to give a compound of Formula 95.

Scheme VII

According to Scheme VII, compounds wherein —G—E— is —CH($R_5$)—S— are prepared by reacting a compound of Formula 93, whose preparation is illustrated in Scheme XXII, with a thiol-substituted heterocycle in the presence of a base to give a compound of Formula 96.

Scheme VIII

According to Scheme VIII, compounds wherein —G—E— is —$CH_2$—CH($R_5$)— are prepared by reacting a heterocyclic aldehyde of Formula 97 with a Wittig reagent ($CH_2$=P(Ph)$_3$) to yield vinyl-heterocycle 98. Olefin epoxidation with m-chloroperoxybenzoic acid affords epoxide 99. Epoxide 99 is opened with a Grignard reagent 100 prepared from the corresponding biphenylbromide. The resulting alcohol 101 is oxidized (e.g., Swern oxidation) to afford ketone 102. The ketone is reacted with the desired Wittig reagent (e.g., Pr-P(Ph)$_3$) to give an intermediate olefin which is reduced with hydrogen in the presence of a catalyst (e.g., platinum or palladium) to afford a compound of Formula 103.

Scheme IX

According to Scheme IX, compounds wherein —G—E— is —CH($R_5$)—$CH_2$— are prepared by converting a biphenyl aldehyde of the Formula 91 to a haloalkylated compound of the Formula 93A (X' is halogen). Compound 93A is converted into Wittig reagent 110 using triphenylphosphine and a suitable base. This Wittig reagent is reacted with heterocyclic aldehyde 97 to give a compound of the Formula 111. This olefin is reduced with hydrogen in the presence of a catalyst such as platinum or palladium to give a compound of the Formula 112.

Scheme X

According to Scheme X, compounds wherein —G—E— is —N($R_5$)—$CH_2$— are prepared by alkyalting amine 82 with $R_5$Cl in the presence of a base. The resulting amine 82a is reductively aminated with aldehyde 97 to give a compound of the Formula 114.

Scheme XI

According to Scheme XI, compounds wherein —G—E— is —NH—CH($R_5$)— are prepared by reacting a heterocyclic nitrile 115 with an alkyl Grignard reagent (e.g., propylmagnesium bromide) and then hydrolyzing the intermediate imine to give a ketone of the Formula 116. Reductive amination with a biphenylamine 82 yields a compound of the Formula 117.

Scheme XII

According to Scheme XII, compounds wherein —G—E— is —O—CH($R_5$)— are prepared by reacting a heterocyclic aldehyde with an organometallic reagent (e.g., $R_5$—M is propylmagnesium bromide) to produce a secondary alcohol of the Formula 120. The alcohol is converted to a leaving group (for example, mesylate) and then is coupled with the biphenyl alcohol in the presence of a base to afford a compound of the Formula 121.

Scheme XIII

According to Scheme XIII, compounds wherein —G—E— is —S—CH($R_5$)— are prepared by converting a secondary alcohol to a leaving group (e.g., X' is mesylate) and then displacing it with biphenyl thiol 85 in the presence of a base to afford a compound of the Formula 123.

Scheme XIV

According to Scheme XIV, compounds wherein —G—E— is —NH—N($R_5$)— are prepared by converting a biphenylamine 82 into a urea of the Formula 124. The urea is reacted with bromine in the presence of a base to yield hydrazine 125. Alkylation with an alkyl bromide (e.g., $R_5$X' is propyl bromide), followed by displacement of a chloro heterocycle with the secondary amine 125, affords a compound of the Formula 126.

Scheme XV

According to Scheme XV, compounds wherein —G—E— is —N($R_5$)—NH— are prepared by first converting amine 82a to urea 130. Urea 130 is converted to hydrazine 131 by treatment with bromine in base. Hydrazine 131 is reacted with chloro-heterocycle D-Cl to afford a compound of the Formula 132.

SCHEME I
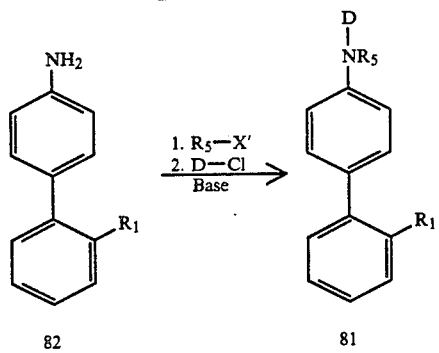
SCHEME IVB
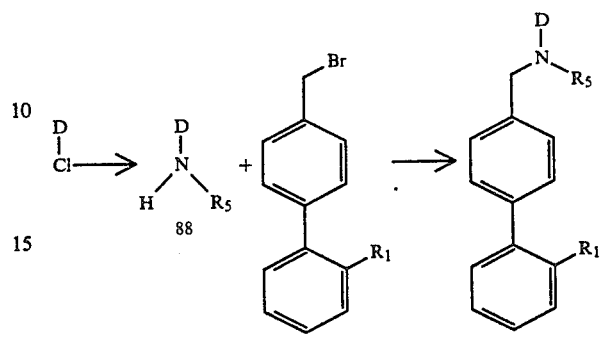
SCHEME II
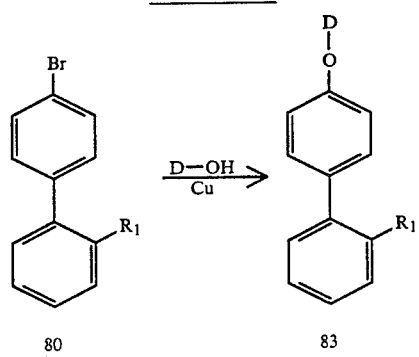
SCHEME V
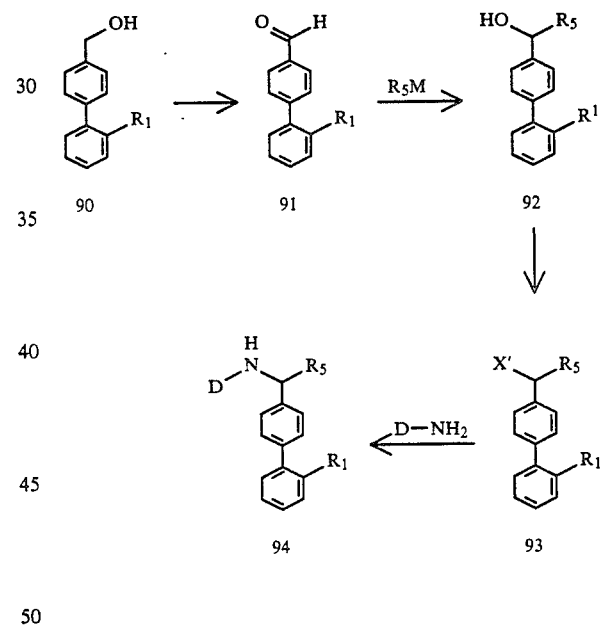
SCHEME III
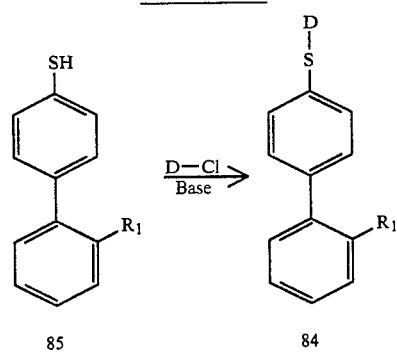
SCHEME IVA
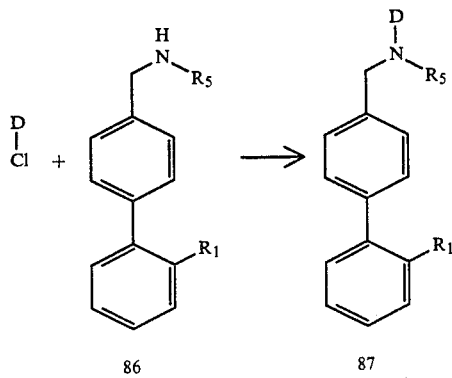
SCHEME VIA
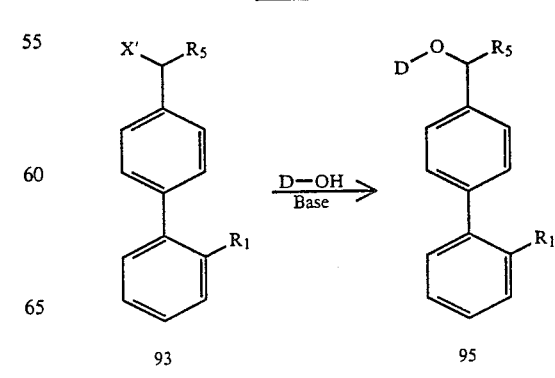

SCHEME VIB

SCHEME VII

SCHEME VIII

SCHEME IX
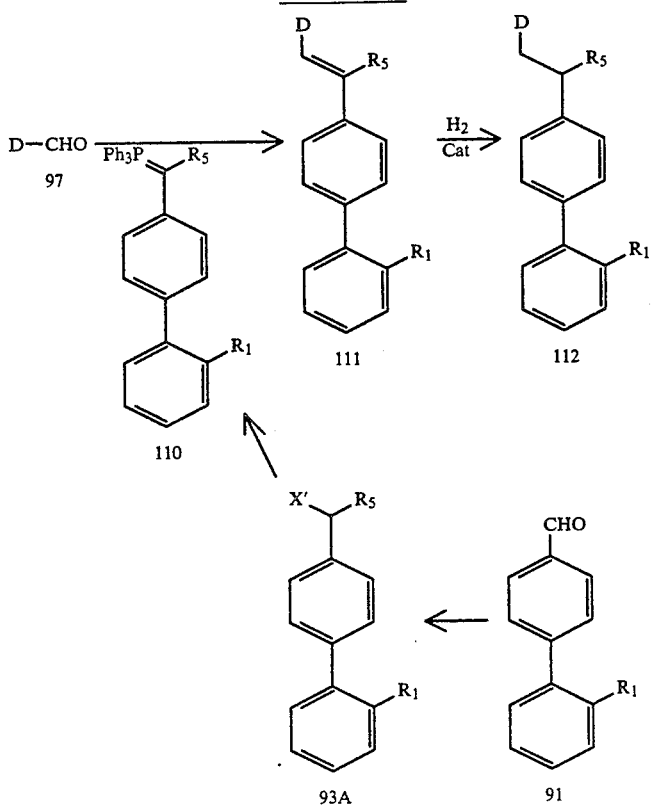
SCHEME X
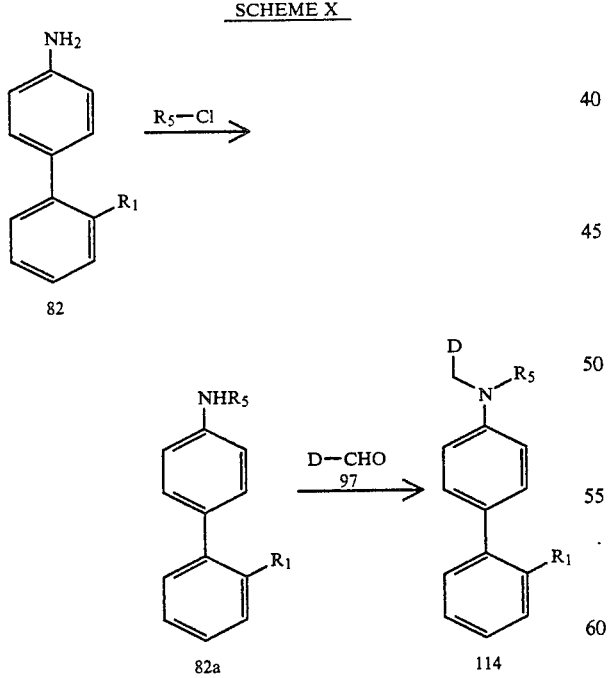
-continued
SCHEME XI
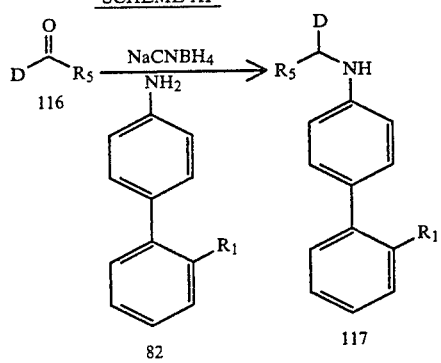
SCHEME XI
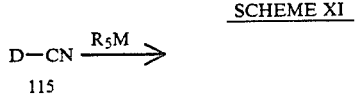
SCHEME XII
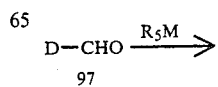

SCHEME XII -continued
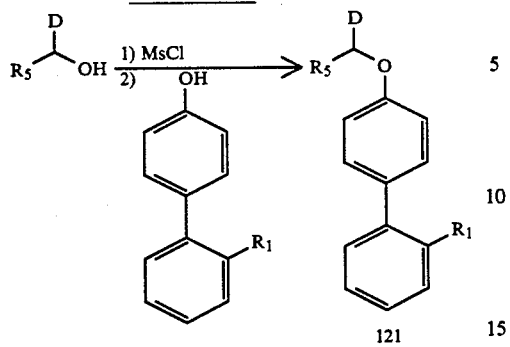
SCHEME XIII
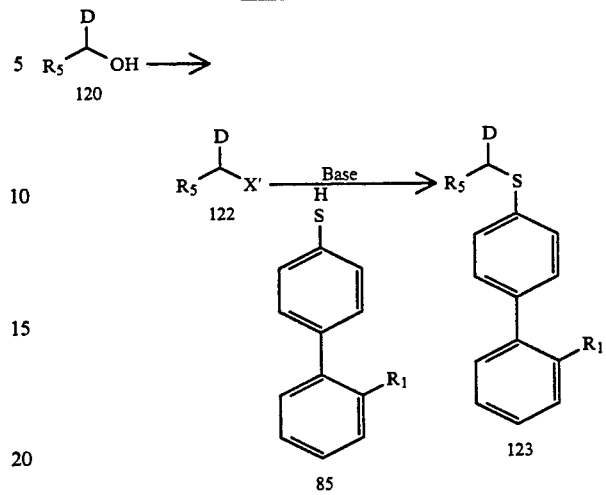
SCHEME XIV
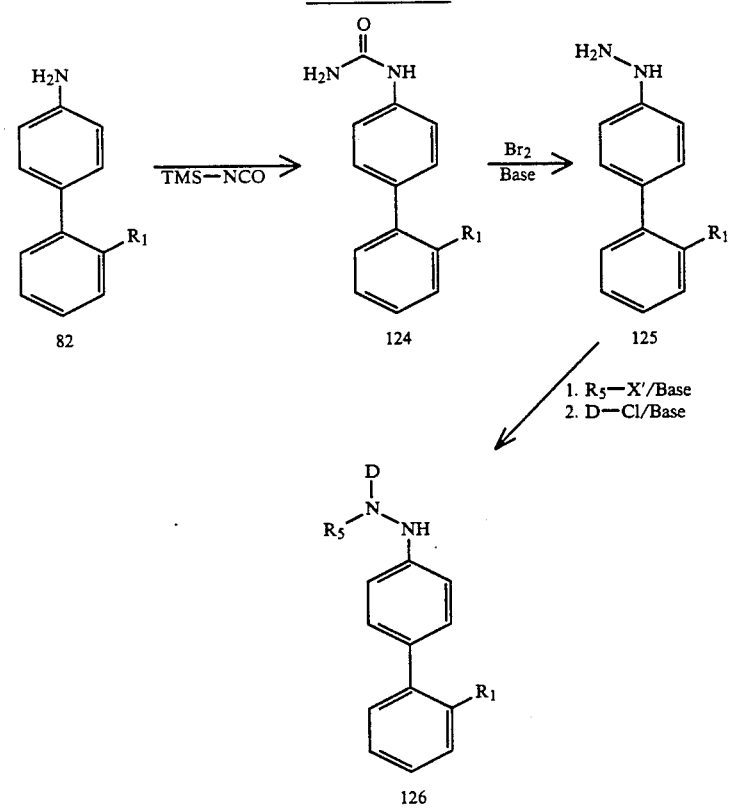

SCHEME XV

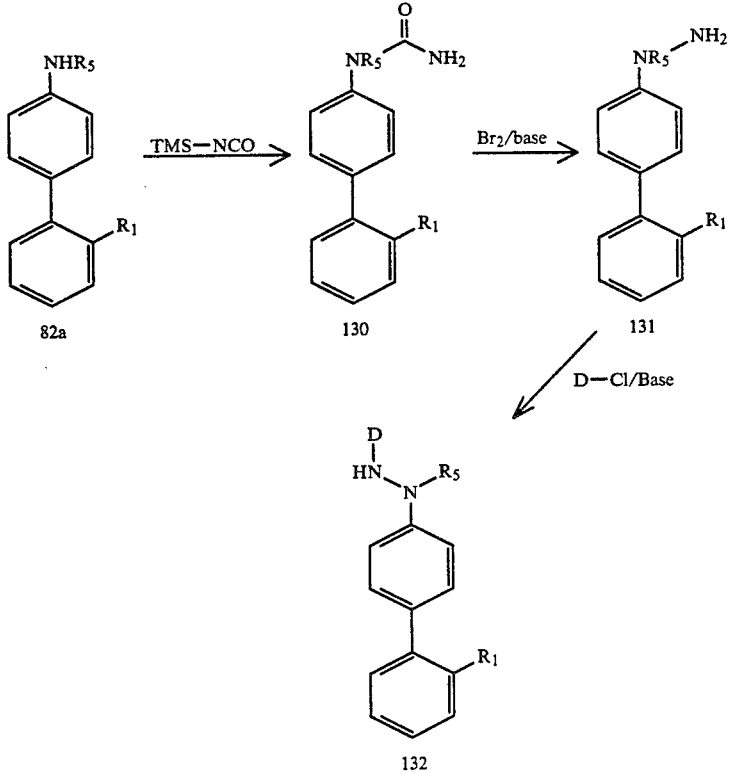

Schemes XVI–XXXII illustrate methods of preparing compounds of the invention comprising various heterocyclic groups D.

Scheme XVI

Scheme XVI discloses the preparation of a compound of the invention comprising a substituted thiophene (in particular, 4-{N-allyl-N-[(2'-[1H-tetrazol-5-yl]biphenyl-4-yl)methyl]amino}-2-methyl-thiophene-3-carboxylic acid). A compound of the Formula 200, prepared as described by Benary and Baravian, Chem. Ber. 48, 593 (1915), is reacted with potassium hydrogen sulfide, followed by ammonium acetate, to give a compound of the Formula 201. This amino-thiophene is reacted first with sodium bis(trimethylsilyl)amide, followed by allyl bromide, to give the allylamino compound 202. Compound 202 is reacted with N-triphenyl-methyl-5-[2-(4'-bromomethyl-biphenyl)]tetrazole 203, prepared as described by P. E. Aldrich, et al., in European Patent Application Number 291969, using lithium hexamethylsidisiliazide as the base. The resulting compound of the Formula 204 is deprotected using formic acid and hydrolyzed using sodium hydroxide to give a compound of the Formula 205.

Scheme XVII

Scheme XVII discloses the synthesis of a compound of the invention comprising a substituted 1,2,5-oxadiazole-N-oxide (in particular, 4-methyl-3-{N-propyl-N-[(2'-[1H-tetrazol-5-yl]biphenyl-4-yl)methyl-]amino}-1,2,5-oxadiazole-5-N-oxide). Using the method of Andrianov and Eremeev, Zh. Org. Khim. 20, 150 (1984), the chloro compound 206 is reacted with amine 207, prepared as described in Example 21A, to give a compound of the Formula 208. Oxidative cyclization using potassium ferricyanide affords a compound of the Formula 209. Formic acid deprotection affords a compound of the Formula 210.

Scheme XVIII

Scheme XVIII discloses the synthesis of a compound of the invention comprising a substituted 1,3,4-oxadiazole (in particular, 2-{N-propyl-N-[(2'-[1H-tetrazol-5-yl]biphenyl-4-yl)methyl]amino}-1,3,4-oxadiazole-5-carboxylic acid). The amine 207, prepared as described in Example 21 A, is reacted with phosgene, followed by hydrazine, to give a semicarbazide of the Formula 212. Reaction of 212 with ethyl glycolate affords intermediate 213 which can be brominated and cyclized by the procedure of Werber et al., J. Het. Chem. 14, 1385 (1977), to afford a compound of the Formula 215. Formic acid deprotection, followed by sodium hydroxide hydrolysis, affords a compound of the Formula 216.

Scheme XIX

Scheme XIX discloses the synthesis of a compound of the invention comprising a substituted (in particular, a compound of the invention comprising a substituted 1,2,4-oxadiazole (in particular, 3-{N-propyl-N-[(2'-[1H-tetrazol-5-yl]biphenyl-4-yl)methyl]amino}-1,2,4-oxadiazole-5-carboxylic acid. Dibromoformaldoxime and ethyl cyanoformate react according to the procedure of Humphrey and Wright, J. Het. Chem. 26, 23 (1989) to give a bromo ester of the Formula 220. Compound 220 is reacted with compound 207 in the presence of triethylamine to give a compound of the Formula 221. Normal deprotection using formic acid and sodium hydroxide hydrolysis affords a compound of the Formula 222.

Scheme XX

Scheme XX discloses the synthesis of a compound of the invention comprising a substituted 1,2,4-triazole (in particular, 5-{N-propyl-N-[(2'-[1H-tetrazol-5-yl]biphenyl-4-yl)methyl]amino}-1,2,4-triazole-3-carboxylic acid). Trimethoxyacetonitrile, prepared by the procedure of Kantlehner et al., Synthesis, 358 (1984), is reacted with hydroxylamine to give a compound of the Formula 223. Compound 223 is reacted with trichloroacetic anhydride, according to the method of Eloy and Lenaers, Helvetica Chim. Acta. 49, 1430 (1966) or LaMattina and Mularsk, J. Org. Chem. 49, 4800 (1984), to give a compound of the Formula 224. The trichloromethyl group can be displaced by amine 207 to give a compound of the Formula 225. Formic acid treatment removes the triphenylmethyl protecting group and converts the trimethoxy group to a carboxylic acid to give a compound of the Formula 226.

Scheme XXI

Scheme XXI discloses the synthesis of a compound of the invention comprising a substituted 1,2,4-thiadiazole (in particular, 3-{N-propyl-N-[(2'-[1H-tetrazol-5-yl]biphenyl-4-yl)methyl]amino}-1,2,4-thiadiazole-5-carboxylic acid). A compound of the Formula 230, prepared by the method of Phillips and Ratts, J. Org. Chem. 36, 3145 (1971), is reacted with propyl guanidine to give ester 231. The ester can be alkylated with bromide 203 to give tertiary amine 232. Formic acid deprotection followed by sodium hydroxide hydrolysis affords a compound of the Formula 233.

Scheme XXII

Scheme XXII discloses the synthesis of a compound of the invention comprising a substituted 1,2,4-thiadiazole (in particular, 5-{N-propyl-N-[(2'-[1H-tetrazol-5-yl]biphenyl-4-yl)methyl]amino}-1,2,4-thiadiazole-3-carboxylic acid). Carbethoxy formamidine 234, prepared as described in J. Org. Chem. 27, 3608 (1962), is reacted with perchloro methanethiol to give a compound of the Formula 235. The chloro compound is reacted with secondary amine 207 to give tertiary amine 236. Formic acid deprotection followed by sodium hydroxide hydrolysis gives a compound of the Formula 237.

Scheme XXIII

Scheme XXIII discloses the synthesis of a compound of the invention comprising a substituted 1,2,5-thiadiazole (in particular, 3-{N-propyl-N-[(2'-[1H-tetrazol-5-yl]biphenyl-4-yl)methyl]amino}-1,2,5-thiadiazole-4-carboxylic acid). The known amino thiadiazole of the Formula 240, prepared as described by Meyer and Skibo, J. Med. Chem. 22, 944 (1979), is alkylated with allyl bromide to give an allylamino compound of the Formula 241. Catalytic hydrogenation affords the propylamino compound 242, which is alkylated with bromo compound 203 to give the tertiary amine 243. Formic acid deprotection followed by sodium hydroxide hydrolysis affords a compound of the Formula 244.

Scheme XXIV

Scheme XXIV discloses the synthesis of a compound of the invention comprising a substituted 1,3,4-thiadiazole (in particular, 5-trifluoromethanesulfonamido-2-{N-propyl-N-[(2'-[1H-tetrazol-5-yl]biphenyl-4-yl)methyl]amino}-1,3,4-thiadiazole). A nitro bromo thiadiazole of the Formula 250, prepared by the method of Tomcufcik, U.S. Pat. No. 3,497,597, is reacted with amine 207 and triethylamine in tetrahydrofuran to give tertiary amine 251. Catalytic hydrogenation reduces the nitro group to an amine, which is then reacted with trifluoromethanesulfonic anhydride to give the trifluoromethanesulfonamido compound 252. Formic acid deprotection affords a compound of the Formula 253.

Scheme XXV

Scheme XXV discloses the synthesis of a compound of the invention comprising a substituted isothiazole (in particular, 3-{1-(2'-[1H-tetrazol-5-yl]biphenyl-4-yl)pentyl-2-yl}-isothiazole-4-carboxylic acid). Ethyl pentanoate is deprotonated using lithium hexamethyldisilazide in tetrahydrofuran and then alkylated with N-triphenylmethyl-5-[2-(4'-bromomethyl-biphenyl)]tetrazole 203, prepared as described by P. E. Aldrich, et al., in European Patent Application Number 291969, to give a compound of the Formula 260. The carboxylic acid 260 is homologated according to the method of Jovin et al., J. Chem. Soc. Perkin Trans. I, 1177 (1987) by activating with isopropenyl chloroformate at 0° C. in dichloromethane in the presence of Meldrum's acid and dimethylaminopyridine and stirring at 0° C. The crude product is refluxed in methanol for 6 hrs to give the corresponding β-oxoester 261. The enamino ester 262, prepared by reaction with ammonium chloride in ethanol, is converted to the thiazole 264 via a Vilsmeier salt according to the procedure of Muraoka, et al., J. Chem. Soc. Perkin Trans. I, 1241 (1989) by treating compound 262 with phosphorus oxychloride to give thioformate 263. Addition of m-chloroperoxybenzoic acid to an ethanolic solution of the thioformate provides the fully protected isothiazole 264. Detritylation and saponification according to standard procedures provides a compound of the Formula 265.

Scheme XXVI

Scheme XXVI discloses the synthesis of a compound of the invention comprising a substituted 1,2,3-triazine (in particular, 2-methyl-4-{N-propyl-N-[(2'-[1H-tetrazol-5-yl]biphenyl-4-yl)methyl]amino}-1,2,3-triazine-5-carboxylic acid). Amino ester 270, prepared as described by Albert and Taguchi, J. Chem. Soc. Perkin I, 1629 (1973), is alkylated with allyl bromide in the presence of lithium hexamethyldisilazide and the allyl side chain is catalytically hydrogenated to give the propylamino compound 271. Treatment of 271 with bromo-biphenyl compound 203 in the presence of lithium hexamethyldisilazide gives a compound of the Formula 273. Formic acid deprotection followed by sodium hydroxide hydrolysis affords a compound of the Formula 274.

Scheme XXVII

Scheme XXVII discloses the synthesis of a compound of the invention comprising a substituted 1,2,4-triazole (in particular, 4-methyl-5-{N-propyl-N-[(2'-[1H-tetrazol-5-yl]biphenyl-4-yl)methyl]amino}-4H-1,2,4-triazole-3-carboxylic acid). Following the procedure described in U.S. Pat. No. 4,481,119, N-methyl-N'-aminoguanidine and oxalic acid are reacted, followed by methanol treatment, to afford a compound of the Formula 280. Alkylation of 280 with allyl bromide, followed by catalytic hydrogenation, affords triazole 281. Alkylation of 281 with N-triphenylmethyl-5-[2-(4'- bromomethyl-biphenyl)]tetrazole 203, prepared as described by P. E. Aldrich, et al., in European Patent Application Number 291969, affords a compound of the Formula 282. Formic acid deprotection followed by sodium hydroxide hydrolysis affords a compound of the Formula 283.

Scheme XXVIII

Scheme XXVIII discloses the synthesis of a compound of the invention comprising a substituted pyrrolidine (in particular, 3-{N-propyl-N-[(2'-[1H-tetrazol-5-yl]biphenyl-4-yl)methyl]amino}pyrrolidine-5-carboxylic acid). N-tert-butyloxycarbonyl-4-hydroxyproline benzyl ester is converted to a mesylate 291 by reaction with mesyl chloride and triethylamine. The mesylate is displaced with N-triphenylmethyl-5-[2-(4'-propylaminomethylbiphenyl)]tetrazole, prepared as described in Example 21A, in the presence of triethylamine to give a compound of the Formula 292. Treatment with hydrochloric acid removes the protecting groups and sodium hydroxide hydrolysis affords a compound of the Formula 293.

Scheme XXIX

Scheme XXIX illustrates the general procedure for preparing compounds of the invention wherein D is a 4-substituted thiazole or 4-substituted oxazole. Thiourea, to prepare thiazoles, or urea, to prepare oxazoles, is reacted with the appropriate $\alpha$-chloro-$\beta$-keto ester according to the procedure of Dann (Chem. Ber., 76: 419 (1943)) to give 2-aminothiazole or oxazole 300. Treatment of compound 300 with tert-butyl nitrite and cupric chloride affords the 2-chloro thiazoles or oxazoles 301 in good yield. Coupling of the 2-chloro thiazole or oxazole with the appropriate protected-biphenyltetrazole amine gives compounds of structure 302. Deprotection with tosic acid gives compound 303. Saponification gives the desired BPT-thiazole or oxazole carboxylic acids 304.

Scheme XXX

Scheme XXX illustrates the general procedure for preparing compounds of the invention wherein D is a substituted 1,2,3-triazole. Benzyl bromide is reacted with sodium azide to give benzyl azide. The azide is cyclized with methyl cyanoacetate in the presence of sodium ethoxide in ethanol to give the triazolo compound 310. Alkyl p-toluenesulfonate in dimethyl sulfoxide gives the triazolium tosylate salt 311 which is catalytically hydrogenated to give the N-alkyl amino compound 312. The amino compound is alkylated with the appropriate alkyl halide $R_5X$ (X=halo) to give the N-alkylated compound 313. This compound is then reacted with 4'-bromomethyl-2-tetrazol-5-yl-biphenyl to give the biphenyl compound 314. Deprotection of the tetrazolyl group (for example, with tosic acid) gives compound 315. The ester group is hydrolyzed (for example, with aqueous sodium hydroxide) to give the carboxylic acid compound 316.

Scheme XXXI

Scheme XXXI illustrates the procedure for preparing compounds of the invention wherein D is a 1,2,5-thiadiazole. Diaminopyrimidinone is reacted with hexamethyldisilazane to give the tri-silylated compound 320, which is chlorinated with thionyl chloride to give the chloro compound 321. Refluxing the chloro compound in methanol gives the thiadiazole methyl ester 322. Treatment of 322 with copper(II)bromide and tert-butylnitrite in acetonitrile gives the bromo compound 323. Using the procedures described in Scheme XXIX, the bromo compound is reacted with the protected biphenyltetrazole alkyl amine to give 324. The protecting group is removed with formic acid to give 325 and then the ester is hydrolyzed to give the carboxylic acid 326.

Scheme XXXII

Scheme XXXII illustrates procedures for preparing compounds of the invention wherein D is a substituted imidazole. Compound 330, prepared as described in EP 31708, is reacted with the biphenyl secondary amine by the procedures described in Scheme XXIX to give teriary amine 331. Deprotection of the imidazole (for example, with tosic acid in THF), followed by ester hydrolysis (for example, with aqueous sodium hydroxide), affords the desired product 332.

Compound 340, prepared using the procedures described by Jones in J. Amer. Chem. Soc., 112: 8174 (1990), and then protected as the N-trityl compound, is reacted with the biphenyl secondary amine to give compound 341. Deprotection of the imidazole (for example, with tosic acid in THF), followed by ester hydrolysis (for example, with aqueous sodium hydroxide), affords the desired dicarboxylic acid 342.

Another series of imidazoles is available through intermediate 350. For example, compound 350 wherein $R_3$ is methyl is prepared by the procedure described in J. Chem. Soc., 123: 498 (1923). The bromo compound is nitrogen-protected (for example, with a trityl group) and then reacted with the biphenyl secondary amine by the procedures described in Scheme XXIX to give tertiary amine 351. The usual deprotection and ester hydrolysis affords the desired compound 352.

SCHEME XVI

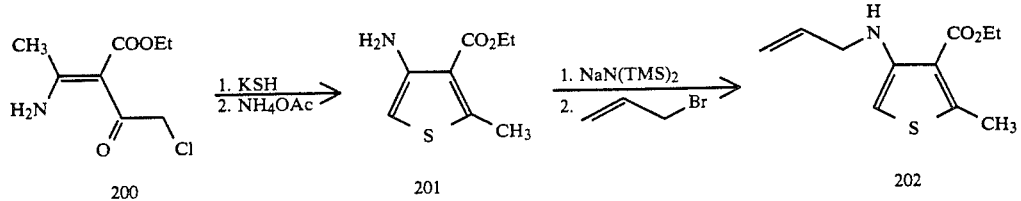

-continued
SCHEME XVI
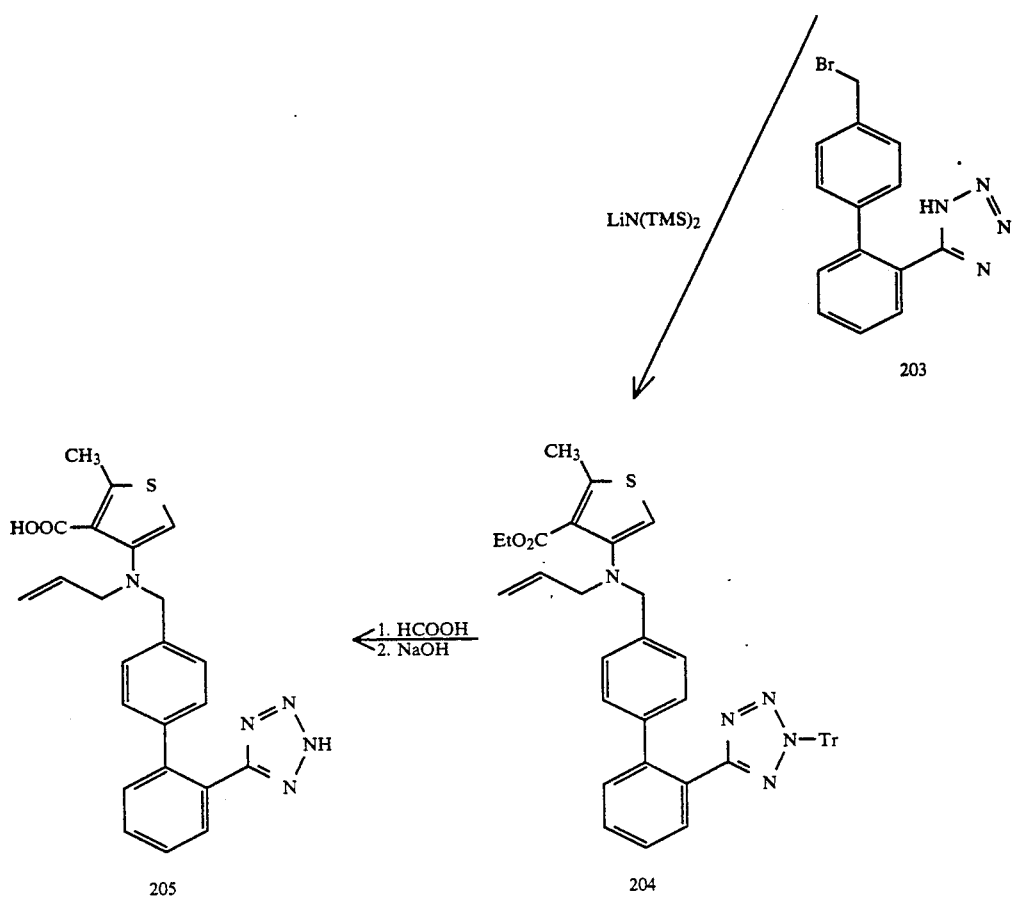
SCHEME XVII
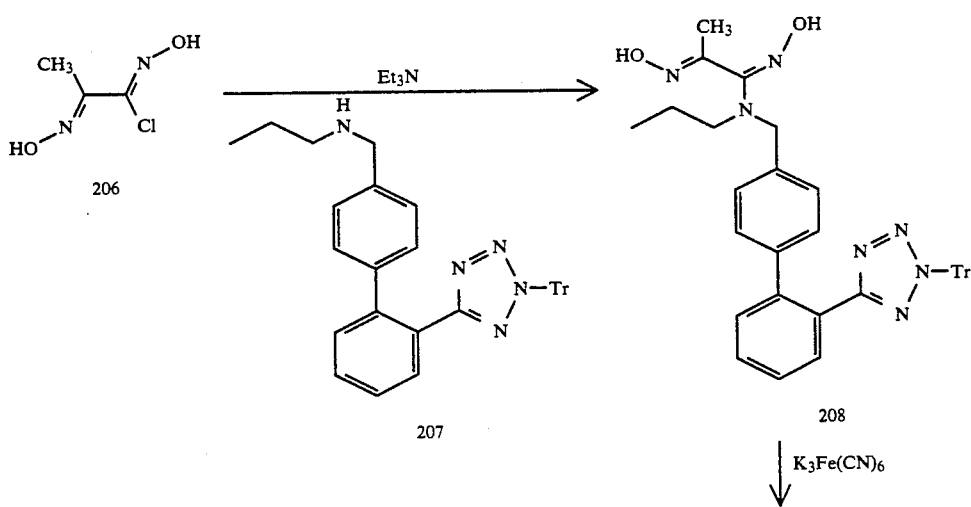

-continued
SCHEME XVII
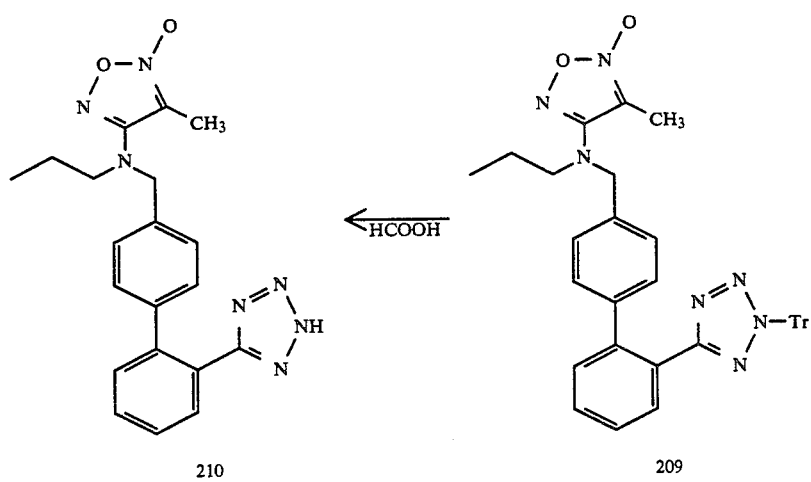
SCHEME XVIII
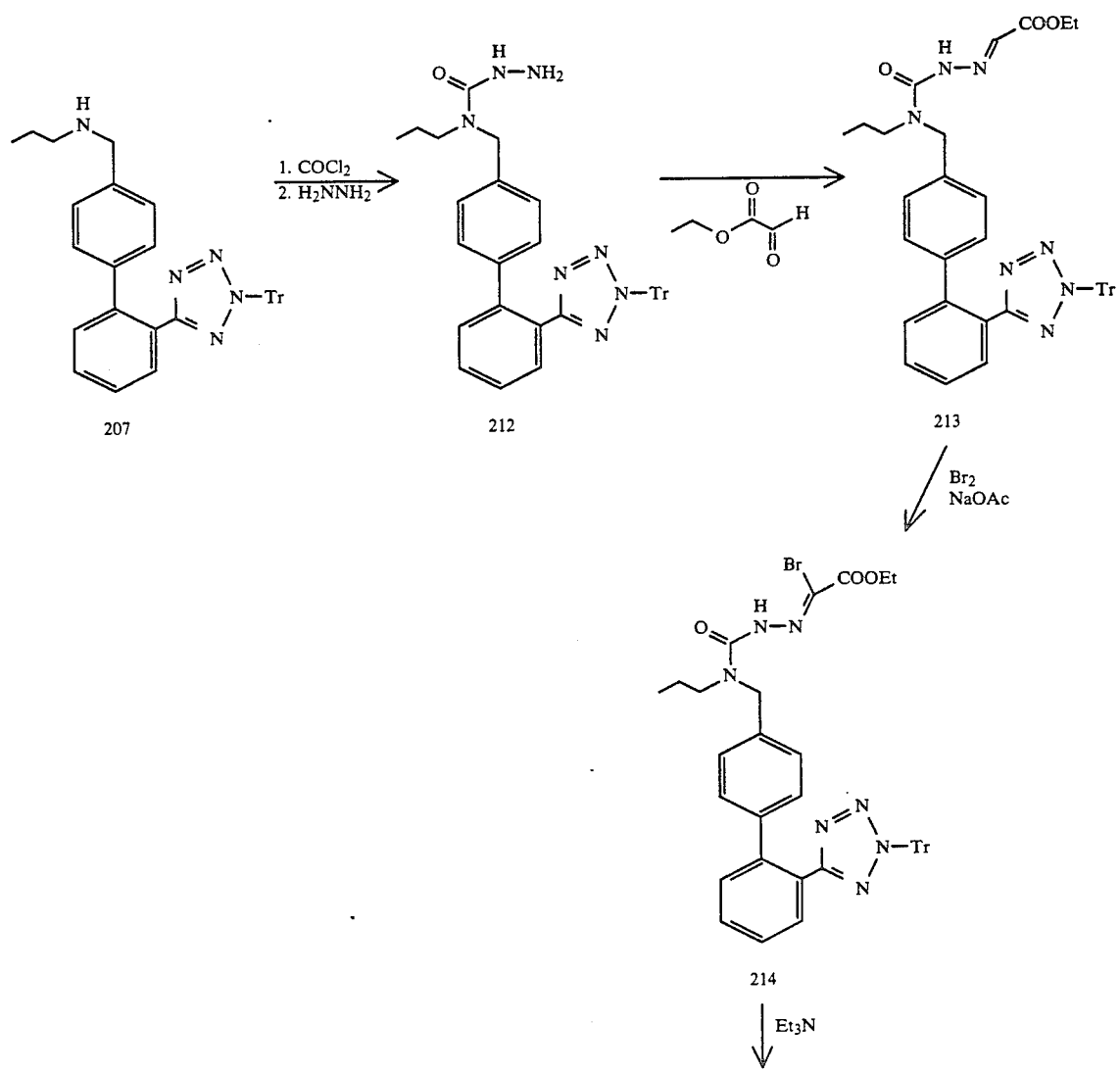

-continued
SCHEME XVIII
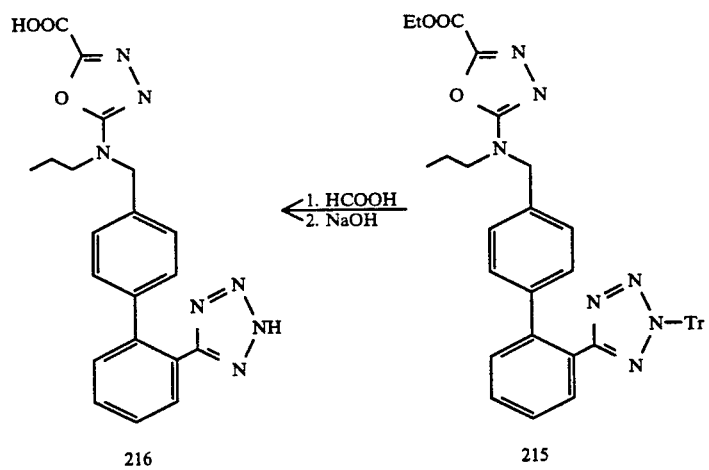
SCHEME XIX
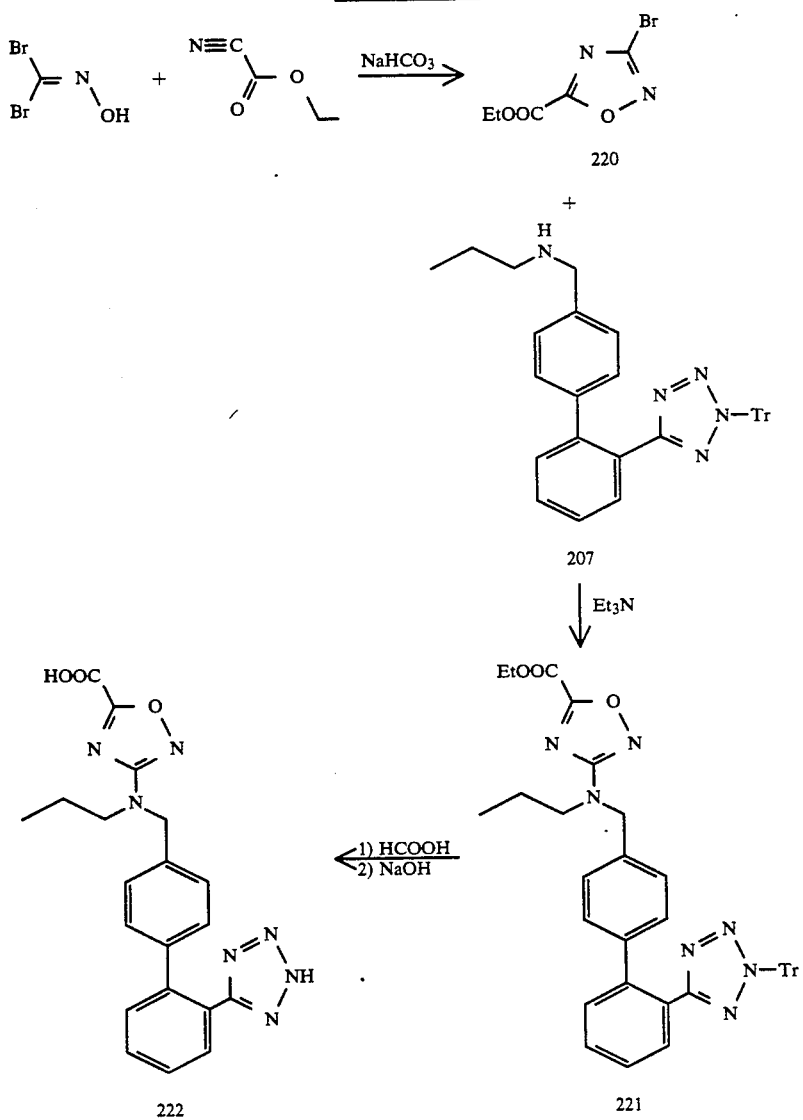

SCHEME XX
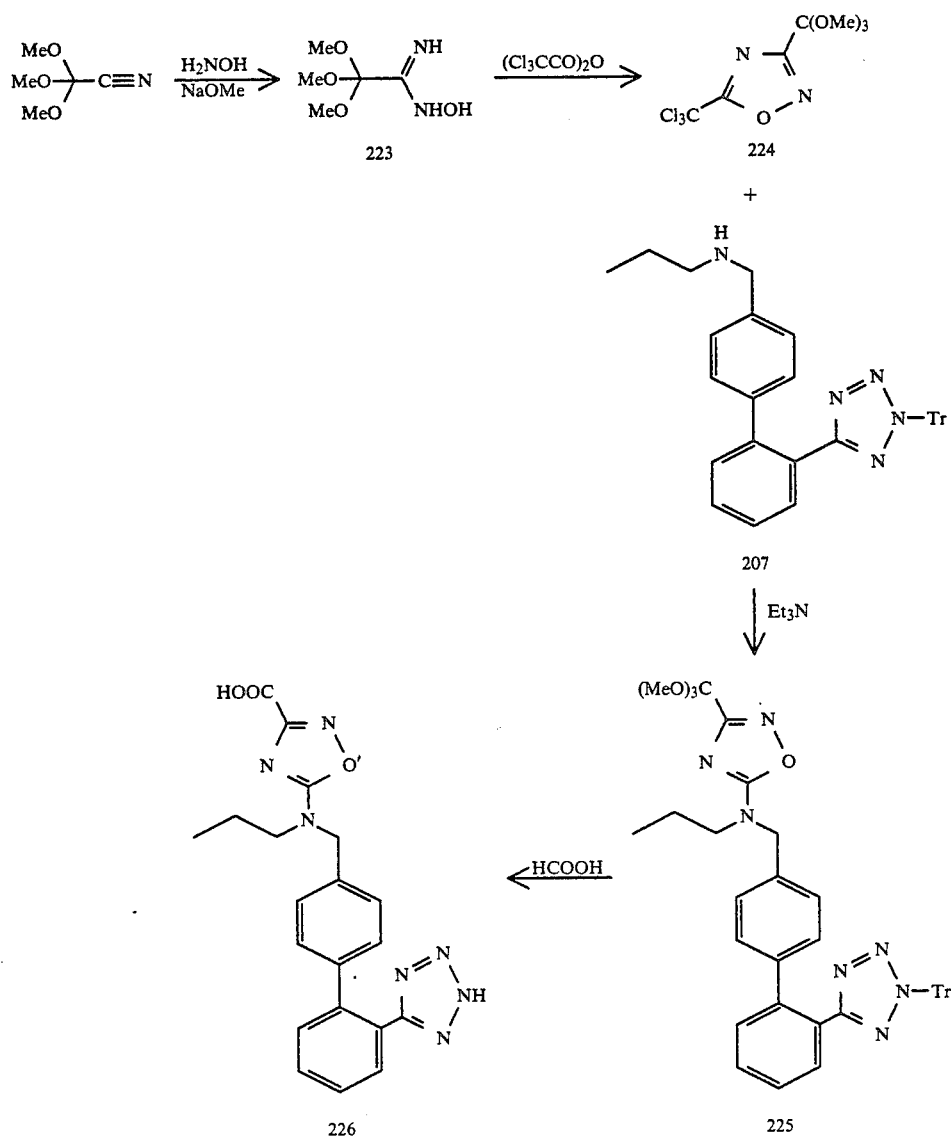
SCHEME XXI
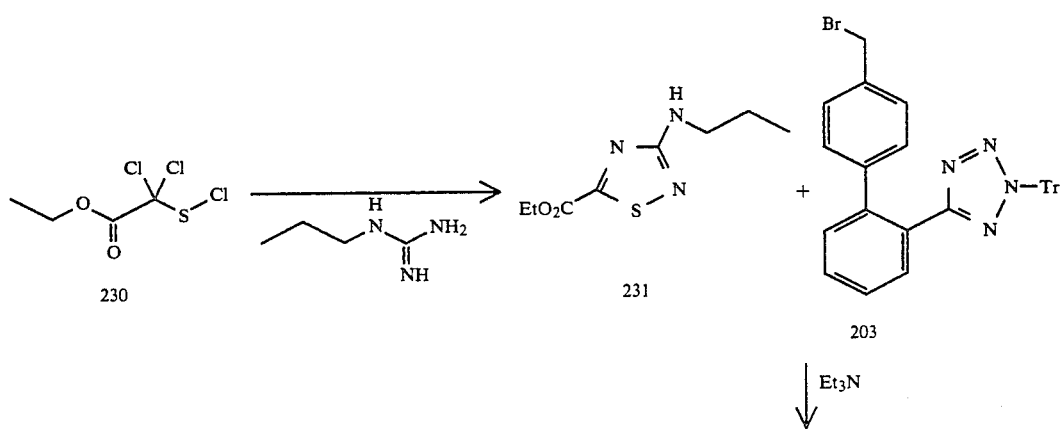

-continued
SCHEME XXI
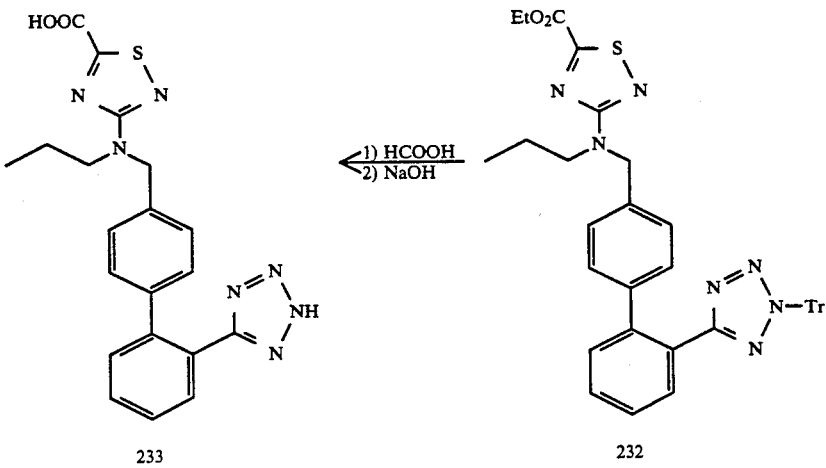
SCHEME XXII
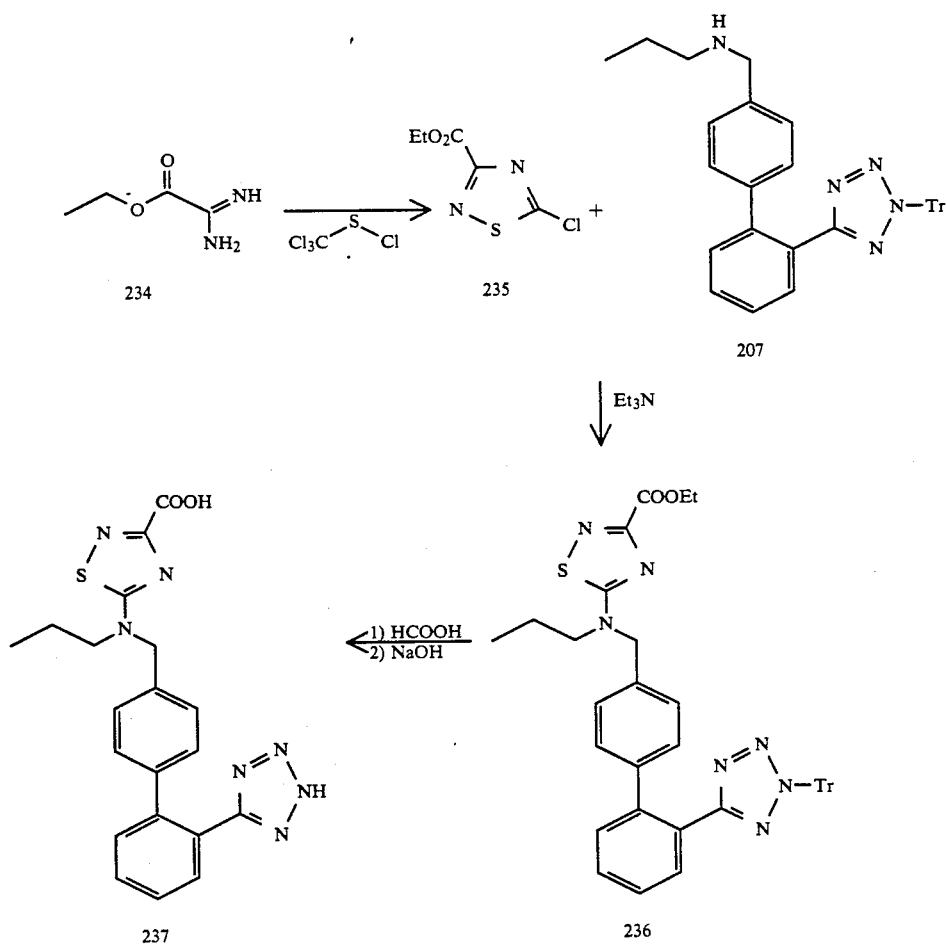

SCHEME XXIII
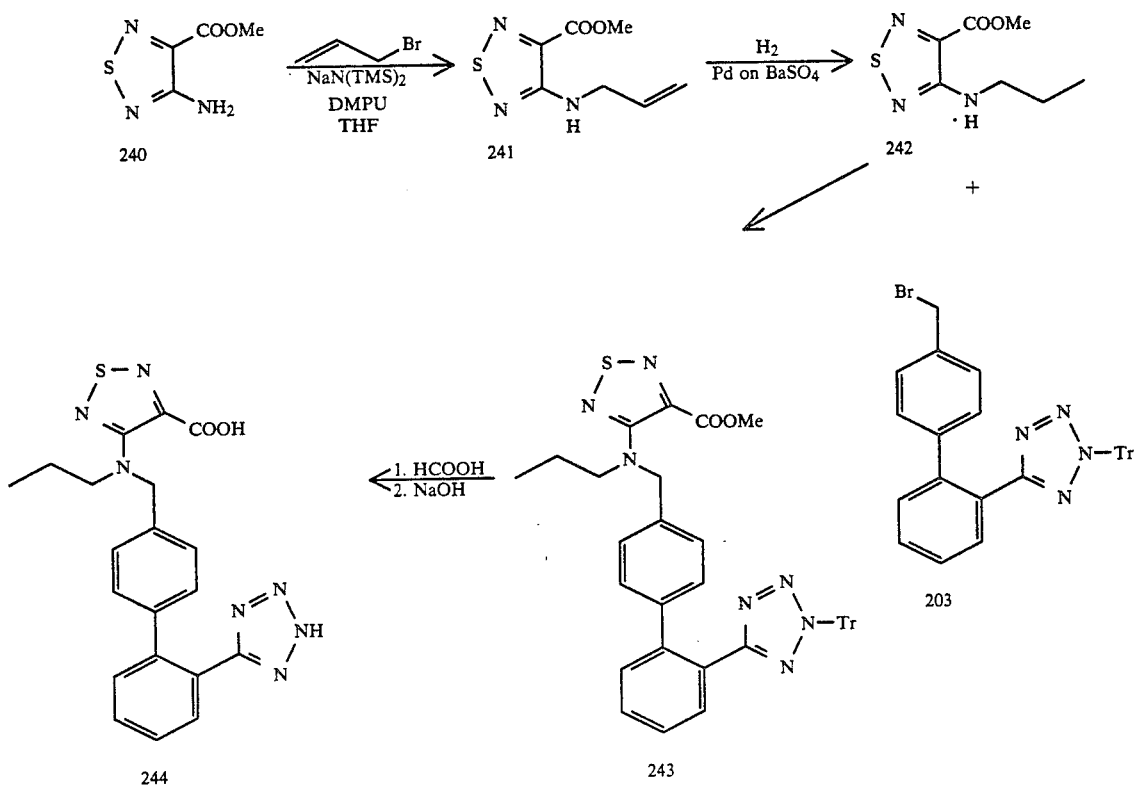
SCHEME XXIV
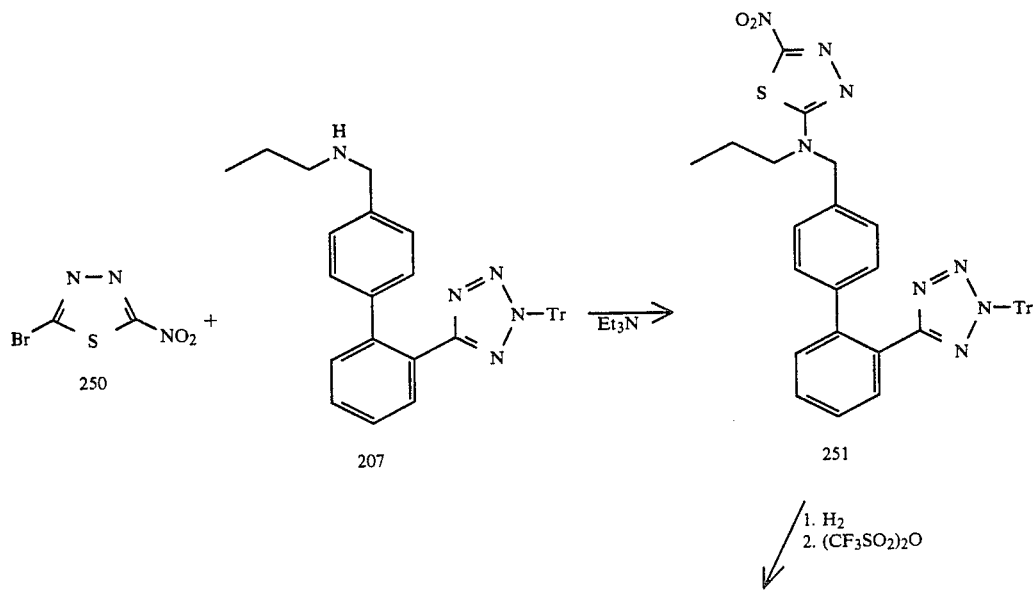

-continued
SCHEME XXIV
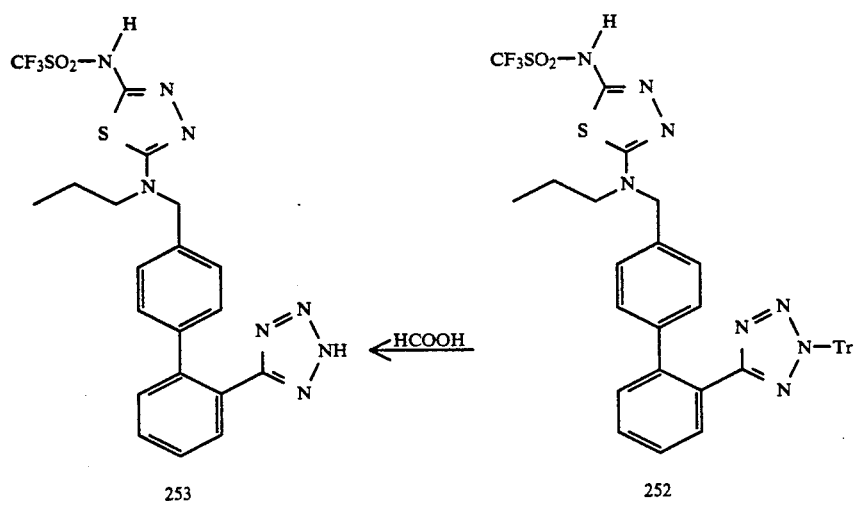
SCHEME XXV
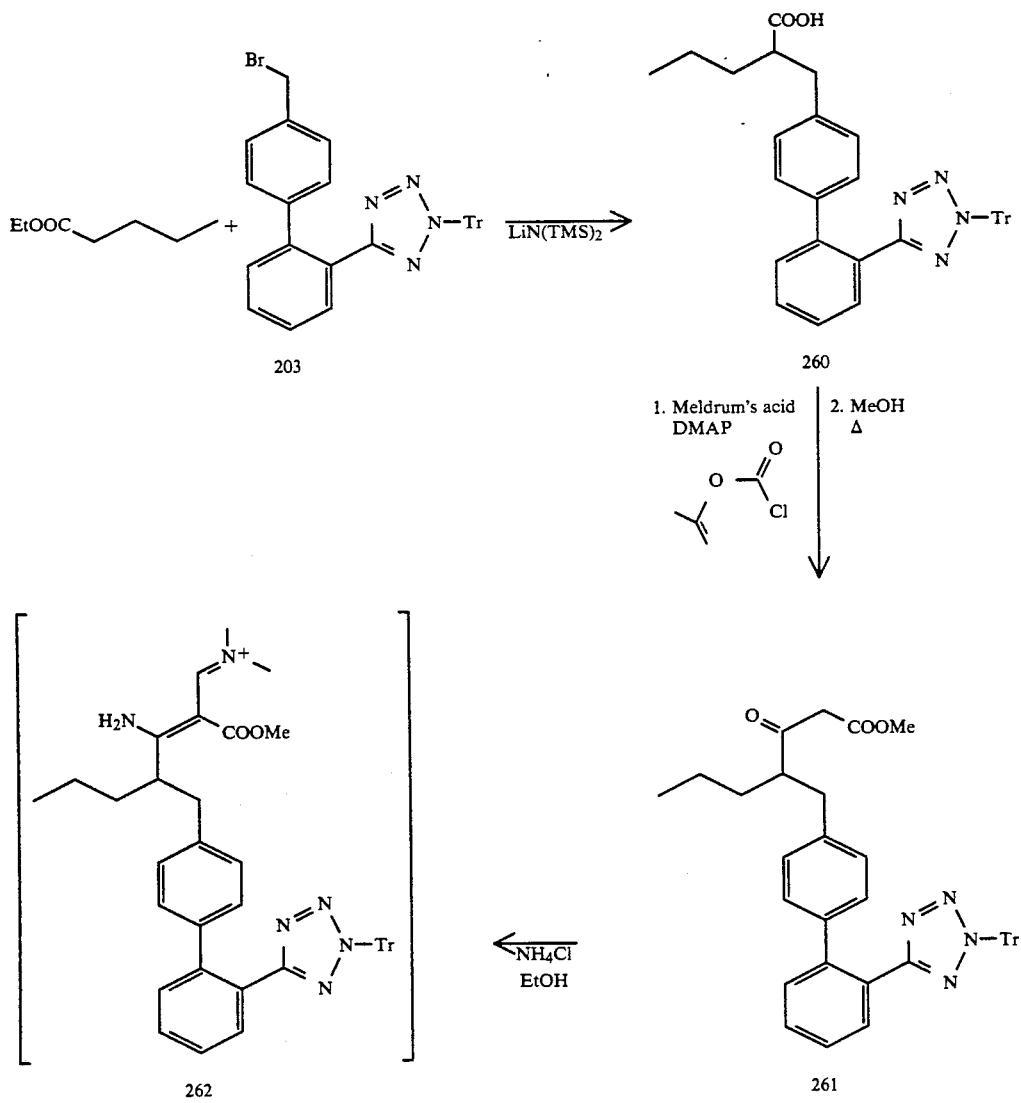

SCHEME XXV
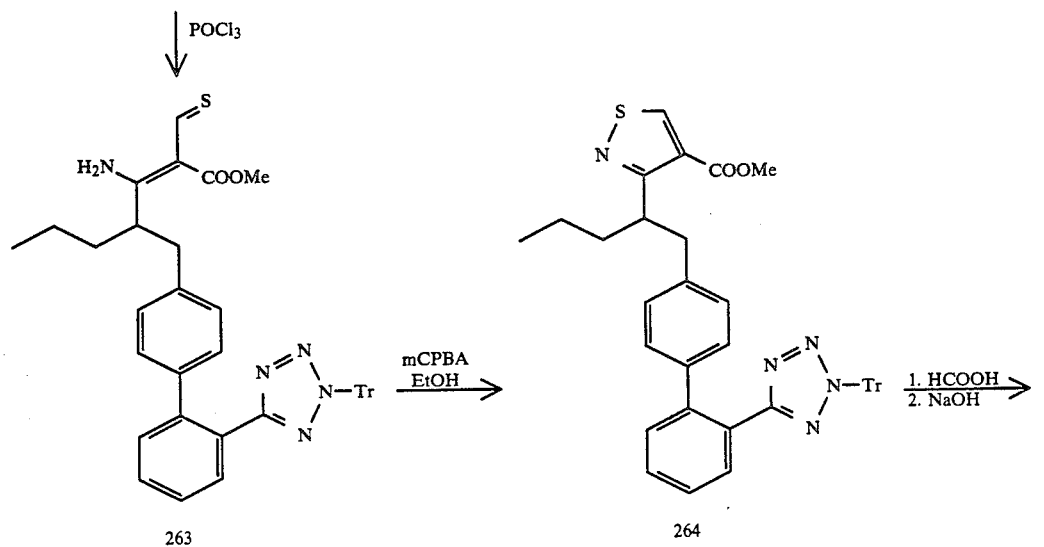
SCHEME XXVI
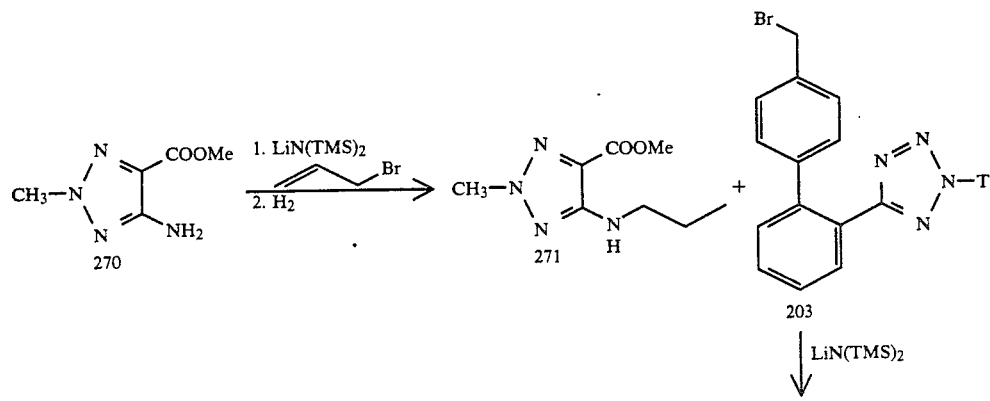

5,326,776
45
46
-continued
SCHEME XXVI
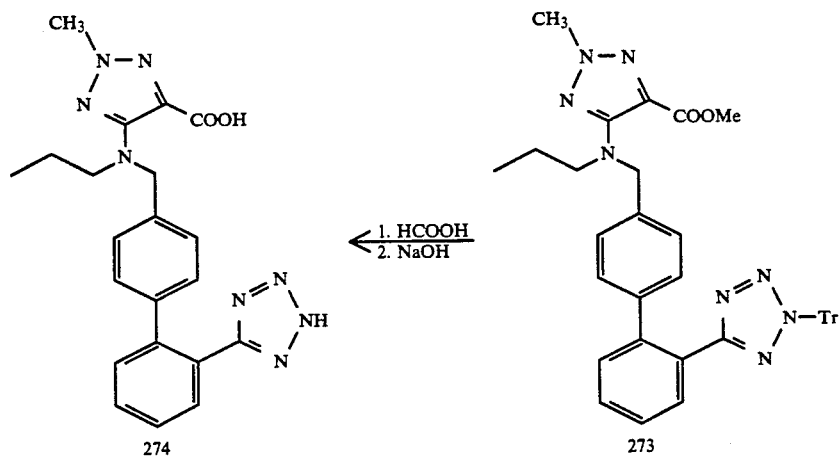
SCHEME XXVII
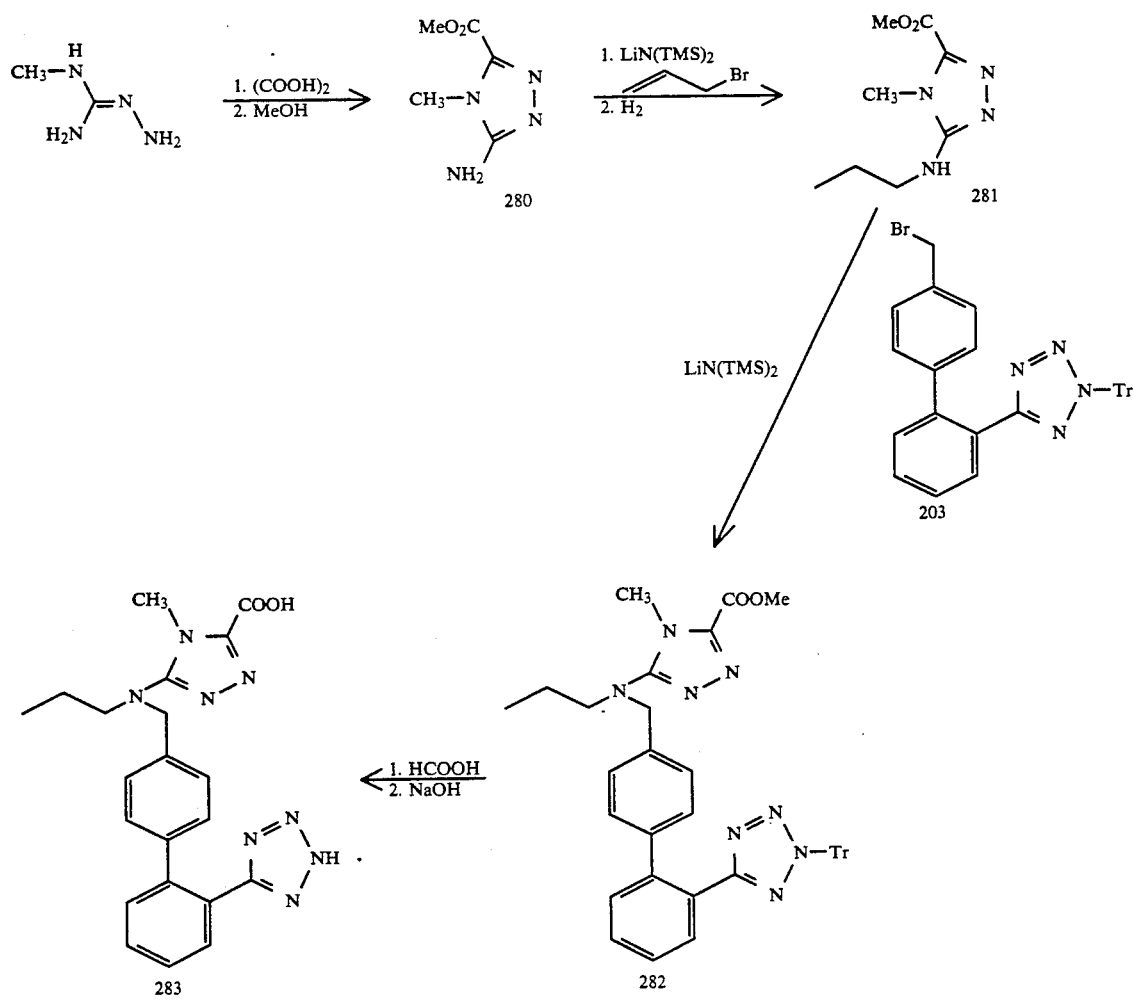

SCHEME XXVIII
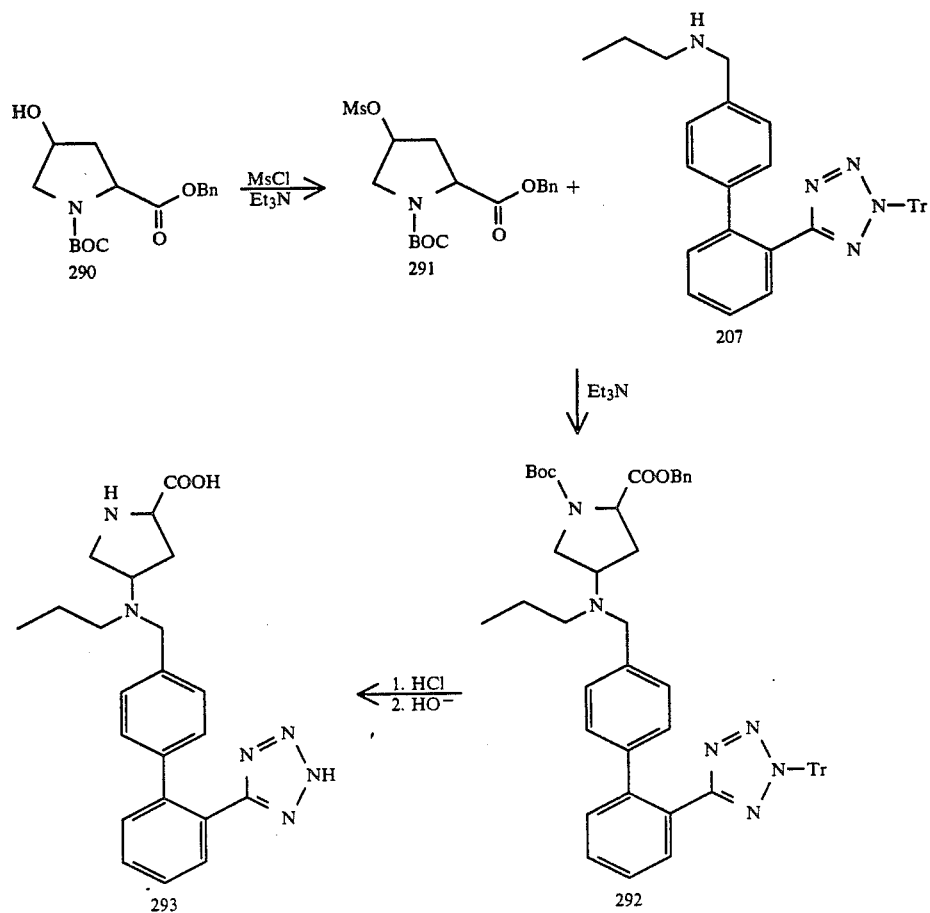
SCHEME XXIX
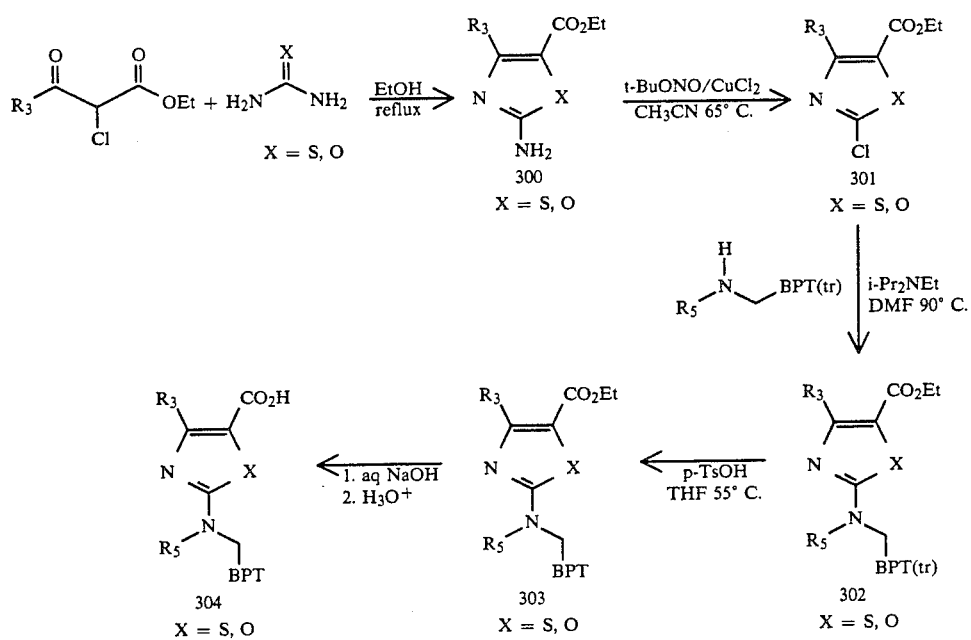

SCHEME XXIX
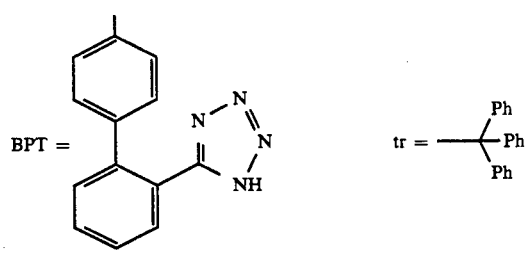
SCHEME XXX
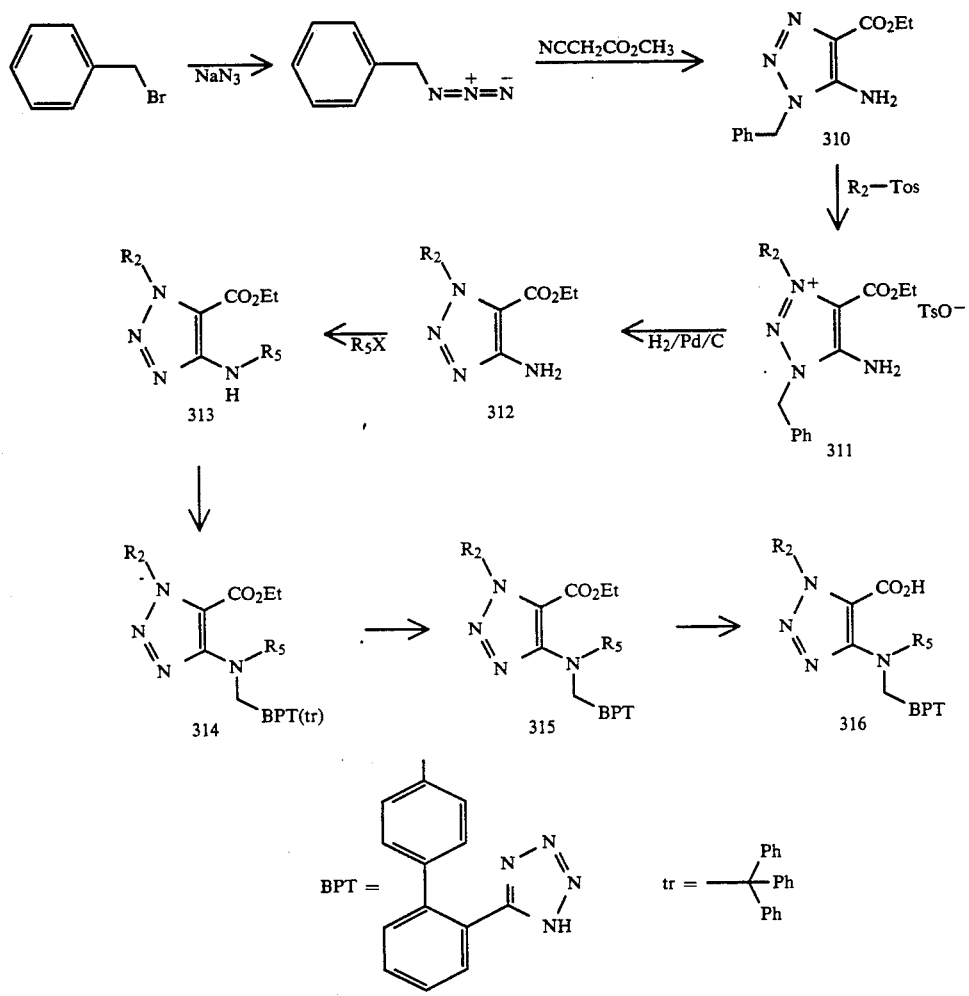
SCHEME XXXI
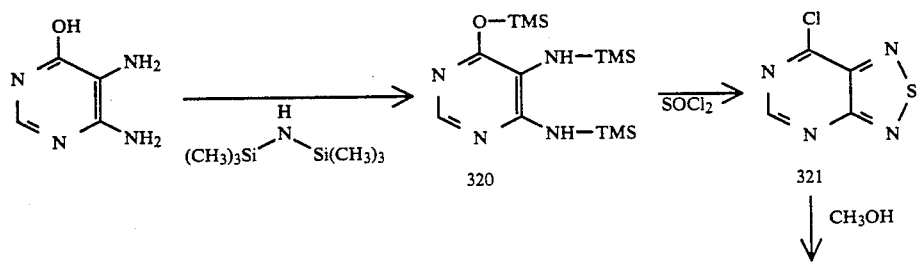

SCHEME XXXI
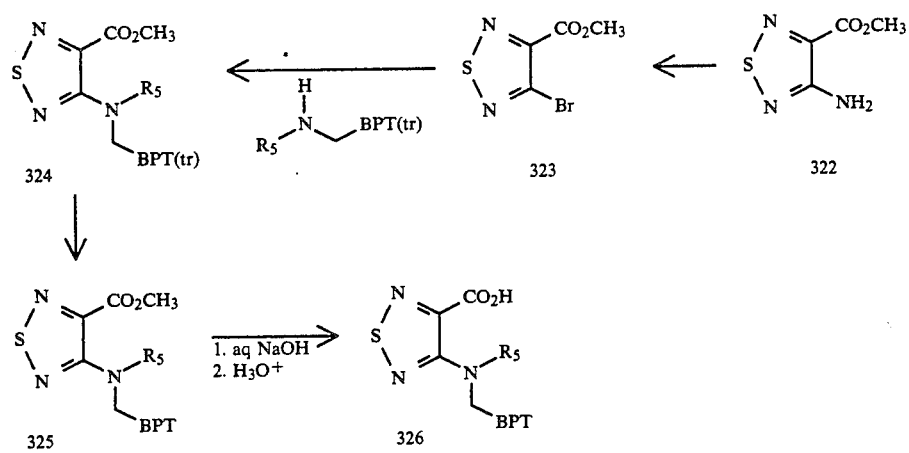
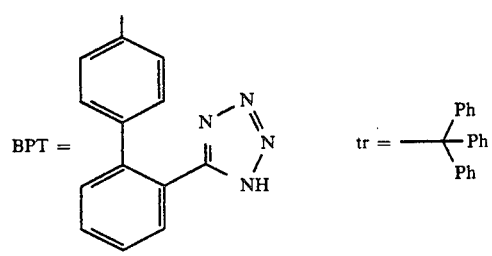
SCHEME XXXII
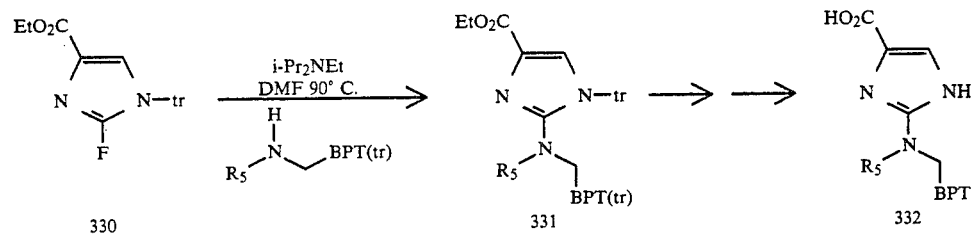
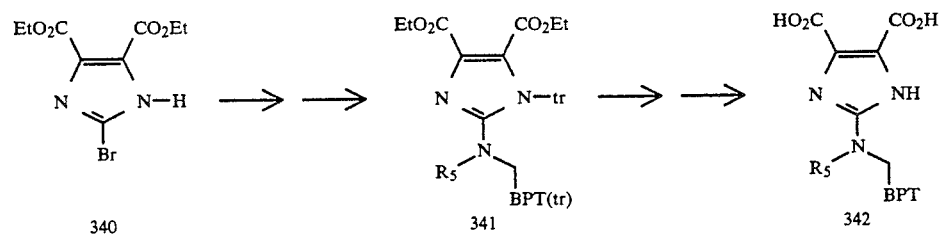
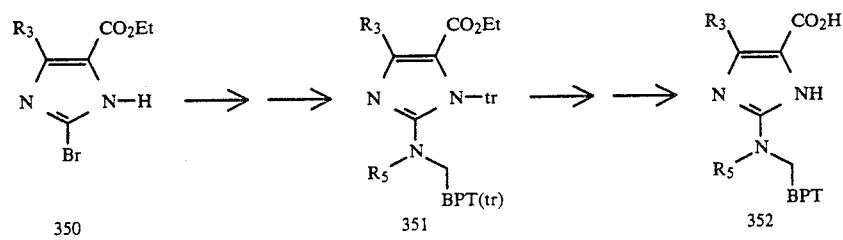

-continued
SCHEME XXXII

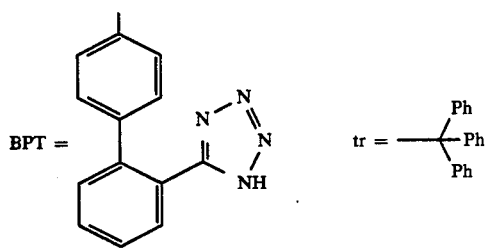

Intermediates useful for the preparation of the novel compounds of this invention include a compound of the formula (II):

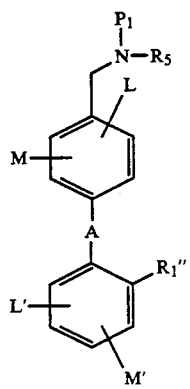

wherein
A, L, L', M, M' and R5 are defined as above;
P1 is hydrogen or an N-protecting group; and
R1'' is R1 as defined above, —NO2, —CN, a tetrazolyl group or an N-protected tetrazolyl group wherein the tetrazole is N-protected with a trityl group, a t-butyl group, a benzyl group, a benzyloxymethyl group or a methoxymethyl group.

Preferred intermediates of formula II are those wherein A is a bond; L, L', M and M' are hydrogen; and R1'' is a tetrazolyl group or an N-protected tetrazolyl group.

Other intermediates useful for the preparation of the novel compounds of this invention include a compound of the formula (III):

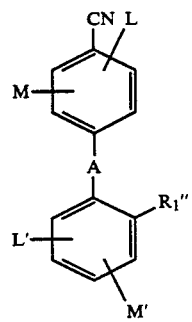

wherein
A, L, L', M and M' are defined as above; and
R1'' is R1 as defined above, —NO2, —CN, a tetrazolyl group or an N-protected tetrazolyl group wherein the tetrazole is N-protected with a trityl group, a t-butyl group, a benzyl group, a benzyloxymethyl group or a methoxymethyl group.

Preferred intermediates of formula III are those wherein A is a bond; L, L', M and M' are hydrogen; and R1'' is a tetrazolyl group or an N-protected tetrazolyl group.

Intermediates of the formula II wherein A is a covalent bond, L, L', M and M' are hydrogen and R1'' is a trazolyl group (i.e., compound 366) can be prepared as illustrated in Scheme XXXIII. Aldehyde 360 (X'' is halogen) can be reductively aminated to provide amine 361a. Protection of the amino group (for example, P1=trityl), followed by Grignard formation, provides compound 362. Reaction of 362 with oxazoline 363 provides, biphenyl 364. Reaction of biphenyl 364 with POCl3 provides nitrile 365. Nitrile 365 can then be elaborated to tetrazole 366 (for example, by reaction with sodium azide).

SCHEME XXXIII

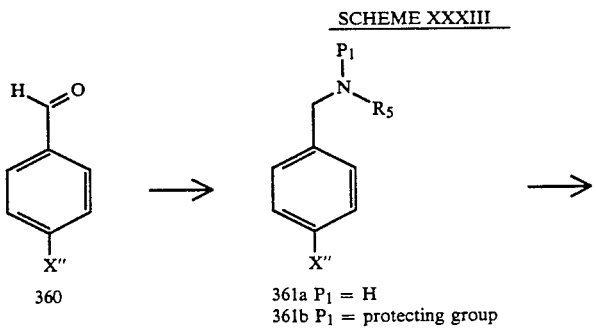

SCHEME XXXIII -continued

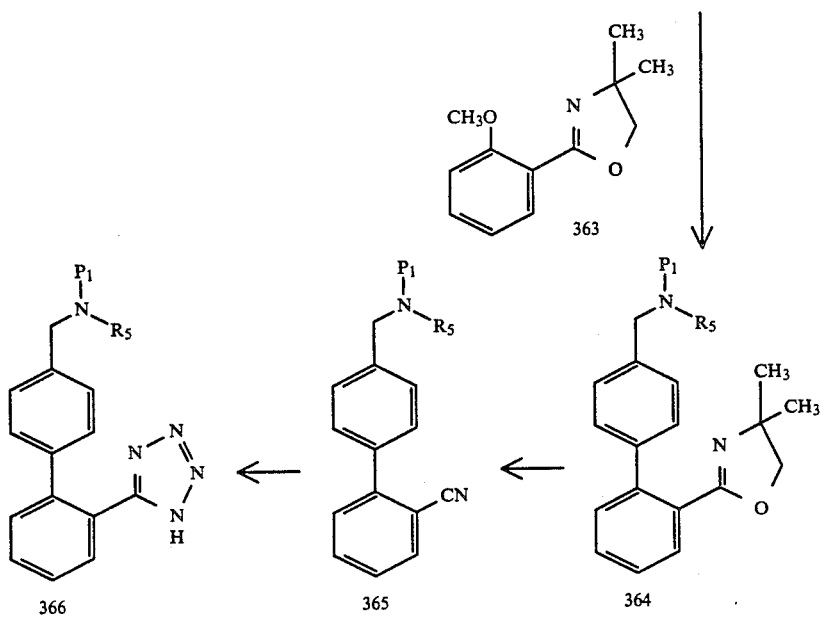

The foregoing may be better understood from the following examples, which are presented for the purpose of illustration and not intended to limit the scope of the inventive concept.

EXAMPLE 1

Ethyl 4-{N-butyl-N-[(2'-[1H-tetrazol-5-yl]biphenyl-4-yl)methyl]amino}-1-methyl-2-(methylthio)imidazole-5-carboxylate

Example 1A

Ethyl 4-butylamino-1-methyl-2-(methylthio)imidazole-5-carboxylate

To ethyl 4-amino-1-methyl-2-(methylthio)imidazole-5-carboxylate (3.014 g, 14.00 mmol), prepared by the method of Gompper et al., Tetrahedron Lett. 1885 (1966), in dimethylformamide (50 mL) at 0° C. was added a solution of 1.0M sodium bis(trimethylsilyl)amide in tetrahydrofuran (14.0 mL, 14.0 mmol). After 1 hour, 1-iodobutane (1.75 mL, 15.4 mmol) was added and the reaction was stirred at ambient temperature for 18 hours. The mixture was diluted with ethyl acetate, washed with water and brine, dried over sodium sulfate and evaporated under reduced pressure. Chromatography of the residue on silica gel eluting with 5% ethyl acetate in hexane afforded 2.706 g (71%) of the desired product as an oil. TLC (10% ethyl acetate/90% hexane) $R_f=0.24$. $^1$H NMR (CDCl$_3$, 300 MHz) d 0.94 (t, 3H), 1.34 (t, 3H), 1.35–1.65 (m, 4H), 2.62 (s, 3H), 3.38–3.49 (m, 2H), 3.66 (s, 3H), 4.28 (q, 2H), 5.58 (br s, 1H). MS (DCl/NH$_3$) m/e 272 (M+H)$^+$.

Example 1B

Ethyl 4-{N-butyl-N-[(2'-[N-triphenylmethyl-1H-tetrazol-5-yl]biphenyl-4-yl)methyl]amino}-1-methyl-2-(methylthio)imidazole-5-carboxylate To the compound resulting from Example 1A (392 mg, 1.44 mmol) in dimethylformamide (6 mL) at 0° C. was added a solution of 1.0M sodium bis(trimethylsilyl)amide in tetrahydrofuran (0.90 mL, 0.90 mmol). After 30 minutes, N-triphenylmethyl-5-[2-(4'-bromomethylbiphenyl)]tetrazole (960 mg, 1.4 mmol, 83% pure), prepared by the method of Aldrich, P. E. et al., European Patent Application 291969, was added, and the reaction was stirred at ambient temperature for 20 hours. The mixture was diluted with ethyl acetate, washed with water and brine, dried over sodium sulfate and evaporated under reduced pressure. Chromatography of the residue on silica gel eluting with 7–9% ethyl acetate in hexane afforded 172 mg (16%) of the desired product as a foam. TLC (10% ethyl acetate/90% hexane) $R_f=0.28$. $^1$H NMR (CDCl$_3$, 300 MHz) d 0.83 (t, 3H), 1.25 (t, 3H), 1.12–1.27 (m, 2H), 1.42–1.55 (m, 2H), 2.57 (s, 3H), 3.23 (t, 2H), 3.70 (s, 3H), 4.22 (q, 2H), 4.50 (s, 2H), 6.85–7.55 (m, 22H), 7.87 (dd, 1H). MS (DCl/NH3)m/e 748 (M+H)$^+$.

Example 1C

Ethyl 4-{N-butyl-N-[(2'-[1H-tetrazol-5-yl]biphenyl-4-yl)methyl]amino}-1-methyl-2-(methylthio)imidazole-5-carboxylate The compound resulting from Example 1B (162.8 mg, 0.218 mmol) in 15:15:1 (v/v/v) acetic acid/tetrahydrofuran/water (4 mL) was heated at reflux for 90 minutes. The solvent was evaporated under reduced pressure, and toluene was added and evaporated. Chromatography of the residue on silica gel eluting with 2–4% methanol in chloroform afforded 72.3 mg (66%) of the desired product as a foam. TLC (10% methanol/90% chloroform) $R_f=0.50$. $^1$H NMR (CDCl$_3$, 300 MHz) d 0.89 (t, 3H), 1.32 (t, 3H), 1.22–1.38 (m, 2H), 1.51–1.63 (m, 2H), 2.49 (s, 3H), 3.32 (t, 2H), 3.70 (s, 3H), 4.25 (q, 2H), 4.59 (s, 2H), 7.17 (d, 2H), 7.39 (d, 2H), 7.42 (dd, 1H), 7.51–7.63 (m, 2H), 8.26 (dd, 1H). MS (DCl/NH3) m/e 506 (M+H)$^+$. Anal calcd for $C_{26}H_{31}N_7O_2S \cdot 0.25\ H_2O$: C, 61.22; H, 6.22; N, 19.22. Found: C, 61.06; H, 5.95; N, 18.95.

EXAMPLE 2

Ethyl 5-{N-butyl-N-[(2'-[1H-tetrazol-5-yl]biphenyl-4-yl)methyl]amino}thiazole-4-carboxylate

Example 2A

Ethyl 5-{N-butyl-N-[(2'-[N-triphenylmethyl-1H-tetrazol-5-yl]biphenyl-4-yl)methyl]amino}thiazole-4-carboxylate (A) and 5-Butylimino-4,5-dihydro-4-ethoxycarbonyl-4-[(2'-[N-triphenylmethyl-1H-tetrazol-5-yl]biphenyl-4-yl)methyl]thiazole (B)

To ethyl 5-(butylamino)thiazole-4-carboxylate (651.2 mg, 2.852 mmol), prepared according to the method of Suzuki et al., Synthesis 834 (1982), in tetrahydrofuran (10 mL) at 0° C. was added 1,3-dimethyl-3,4,5,6-tetrahydro-2(1H)-pyrimidinone (1.70 mL, 14.1 mmol) followed by a solution of 1.0M lithium bis(trimethylsilyl)amide in tetrahydrofuran (3.00 mL, 3.00 mmol). After 30 minutes, N-triphenylmethyl-5-[2-(4'-bromomethylbiphenyl)]tetrazole (2.00 mg, 2.98 mmol, 83% pure), prepared by the method of Aldrich, P. E. et al., European Patent Application 291969, was added and the reaction was stirred at ambient temperature for 20 hours. The mixture was evaporated under reduced pressure and the residue dissolved in ethyl acetate. This solution was washed with water and brine, dried over sodium sulfate and evaporated under reduced pressure. Chromatography of the residue on silica gel eluting with 15–25% ethyl acetate in hexane afforded 276 mg (14%) of the desired product (A) as a foam. TLC (20% ethyl acetate/80% hexane) $R_f$=0.14. $^1$H NMR (CDCl$_3$, 300 MHz) d 0.84 (t, 3H), 1.18–1.33 (m, 2H), 1.42 (t, 3H), 1.45–1.60 (m, 2H), 3.17 (t, 2H), 4.39 (s, 2H), 4.41 (q, 2H), 6.85–7.55 (bm, 22H), 7.91 (dd, 1H), 8.17 (s, 1H). MS (DCl/NH$_3$)m/e 705 (M+H)$^+$. Anal calcd for C$_{43}$H$_{40}$N$_6$O$_2$S: C, 73.27; H, 5.72; N, 11.92. Found: C, 73.46; H, 5.88; N, 12.08.

Also obtained from the column was 1.05 g (52%) of C-4 alkylated product (B). TLC (20% ethyl acetate/80% hexane) $R_f$0.19. $^1$H NMR (CDCl$_3$, 300 MHz) d 0.92 (t, 3H), 1.22 (t, 3H), 1.30–1.46 (M, 2H), 1.56–1.78 (m, 2H), 3.12 (dr, 1H), 3.33 (dt, 1H), 3.44 (d, 1H), 3.55 (d, 1H), 4.12–4.32 (m, 2H), 6.85–7.52 (br envelope, 22H), 7.83 (dd, 1H), 8.18 (s, 1H). MS (DCl/NH$_3$) m/e 705 (M+H)$^+$. Anal calcd for C$_{43}$H$_{40}$N$_6$O$_2$S: C, 73.27; H, 5.72; N, 11.92. Found: C, 73.15; H, 5.15; N, 12.02.

Example 2B

Ethyl 5-{N-butyl-N-[(2'-[1H-tetrazol-5-yl]biphenyl-4-yl)methyl]amino}thiazole-4-carboxylate The compound resulting from Example 2A (A) (244 mg, 0.346 mmol) in 15:15:1 (v/v/v) acetic acid/tetrahydrofuran/water (8 mL) was heated at reflux for 90 minutes. The solvent was evaporated under reduced pressure, and toluene was added and evaporated. Chromatography of the residue on silica gel eluting with 2–4% methanol in chloroform afforded.119 mg (74%) of the desired product as a foam. TLC (10% methanol/90% chloroform) $R_f$=0.30. $^1$H NMR (CDCl$_3$, 300 MHz) d 0.88 (t, 3H), 1.30 (t, 3H), 1.23–1.40 (m, 2H), 1.52–1.67 (m, 2H), 3.26 (t, 2H), 4.29 (q, 2H), 4.50 (s, 2H), 7.12 (d, 2H), 7.25 (d, 2H), 7.43 (dd, 1H), 7.51–7.65 (m, 2H), 8.11 (s, 1H), 8.13 (dd, 1H). MS (DCl/NH$_3$) m/e 463 (M+H)$^+$. Anal calcd for C$_{24}$H$_{26}$N$_6$O$_2$S: C, 62.32; H, 5.67; N, 18.17. Found: C, 62.31; H, 6.03; N, 18.44.

EXAMPLE 3

5-{N-Butyl-N-[(2'-[1H-tetrazol-5-yl]biphenyl-4-yl)methyl]amino}thiazole-4-carboxylic acid The compound resulting from Example 2B (94.7 mg, 0.205 mmol) in 1M aqueous potassium hydroxide solution (2 mL) was stirred for 22 hours at ambient temperature. The mixture was acidified with 2M hydrochloric acid and filtered. The resulting solid was dissolved in 10% methanol in chloroform, dried over sodium sulfate and evaporated with hexane chases to afford 80.1 mg (90%) of the desired product as a solid. TLC (25% acetic acid/25% ethyl acetate/25% n-butanol/25% water) $R_f$=0.65. $^1$H NMR (CDCl$_3$, 300 MHz) d 0.90 (t, 3H), 1.18–1.45 (m, 2H), 1.54–1.78 (m, 2H), 3.27 (t, 3H), 4.49 (s, 2H), 7.11 (d, 2H), 7.20 (d, 2H), 7.43 (d, 1H), 7.43–7.66 (m, 3H), 8.02 (d, 1H), 8.34 (s, 1H). MS (DCl/NH$_3$)m/e 435 (M+H)$^+$. Anal calcd for C$_{22}$H$_{22}$N$_6$O$_2$S.0.5 n-hexane: C, 62.87; H, 6.12; N, 17.60. Found: C, 63.17; H, 6.25; N, 17.29. Exact Mass Calcd for C$_{22}$H$_{23}$N$_6$O$_2$S, (M+H): 435.1603. Found: 435.1604.

EXAMPLE 4

Ethyl 4-{N-butyl-N-[(2'-[1H-tetrazol-5-yl]biphenyl-4-yl)methyl]amino}-1-methylimidazole-5-carboxylate

Example 4A

Ethyl 4-amino-1-methylimidazole-5-carboxylate

Ethyl 4-amino-1-methyl-2-(methylthio)imidazole-5-carboxylate (1.52 g, 7.11 mmol) and W-2 Raney nickel (3 g, 50% in water) in ethanol (25 mL) were heated at reflux for 12 hours. Additional Raney nickel (ca 1.5 g, 50% in water) was added and heating was continued for an additional 3 hours adding Raney nickel (ca 1.5 g, 50% in water) every hour. The reaction was filtered and the filtrate evaporated under reduced pressure. Chromatography of the residue on silica gel eluting with 1.5% methanol in chloroform afforded 0.72 g (60%) of the desired product as a solid. TLC (10% methanol/90% chloroform) $R_f$=0.47. $^1$H NMR (CDCl$_3$, 300 MHz) d 1.38 (t, 3H), 3.77 (s, 3H), 4.32 (q, 2H), 4.82 (br, 2H), 7.13 (s, 1H). MS (DCl/NH$_3$) m/e 170 (M+H)$^+$.

Example 4B

Ethyl 4-butylamino-1-methylimidazole-5-carboxylate

To the compound resulting from Example 4A (710 mg, 4.20 mmol) in dimethylformamide (15 mL) at 0° C. was added a solution of 1.0M sodium bis(trimethylsilyl)amide in tetrahydrofuran (4.40 mL, 4.40 mmol). After 30 minutes, 1-iodobutane (0.52 mL, 4.6 mmol) was added and the reaction was stirred at ambient temperature for 22 hours. The mixture was diluted with ethyl acetate, washed with water and brine, dried over sodium sulfate and evaporated under reduced pressure. Chromatography of the residue on silica gel eluting with 50% ethyl acetate in hexane afforded 269 mg (28%) of the desired product as an oil. TLC (50% ethyl acetate/50% hexane) $R_f$=0.17. $^1$H NMR (CDCl$_3$, 300 MHz) d 0.94 (t, 3H), 1.36 (t, 3H), 1.32–1.48 (m, 2H), 1.53–1.65 (m, 2H), 3.36–3.47 (m, 2H), 3.74 (s, 3H), 4.31 (q, 2H), 5.02 (br s, 1H), 7.14 (s, 1H). MS (DCl/NH$_3$) m/e 226 (M+H)$^+$.

Example 4C

Ethyl 4-{(N-butyl-N-[(2'-[N-triphenylmethyl-1H-tetrazol-5-yl]biphenyl-4-yl)methyl]amino}-1-methylimidazole-5-carboxylate To the compound resulting from Example 4B (266.3 mg, 1.18 mmol) in tetrahydrofuran (4 mL) at 0° C. was added 1,3-dimethyl-3,4,5,6-tetrahydro2(1H)-pyrimidinone (0.70 mL, 5.8 mmol) followed by a solution of 1.0M lithium bis(trimethylsilyl)amide in tetrahydrofuran (1.30 mL, 1.30 mmol). After 30 rain triphenylmethyl-5-[2-(4'-bromomethylbiphenyl)]tetrazole (0.85 mg, 1.2 mmol, 83% pure), prepared according to the procedure of Aldrich, P. E. et al., European Patent Application 291969, was added and the reaction was stirred at ambient temperature for 20 hours. The mixture was evaporated and dissolved in ethyl acetate which was washed with water and brine, dried over sodium sulfate and evaporated under reduced pressure. Chromatography of the residue on silica gel eluting with 33% ethyl acetate in hexane afforded 443.7 mg (53%) of the desired product as a foam. TLC (50% ethyl acetate/50% hexane) $R_f=0.29$. $^1$H NMR (CDCl$_3$, 300 MHz) d 0.82 (t, 3H), 1.12–1.25 (m, 2H), 1.29 (t, 3H), 1.42–1.54 (m, 2H), 3.23 (t, 2H), 3.78 (s, 3H), 4.27 (q, 2H), 4.47 (s, 2H), 7.53–6.87 (bin, 23H), 7.87 (dd, 1H). MS (DCl/NH$_3$) m/e 702 (M+H)$^+$.

Example 4D

Ethyl 4-{N-butyl-N-[(2'-[1H-tetrazol-5-yl]biphenyl-4-yl)methyl]amino}-1-methylimidazole-5-carboxylate The compound resulting from Example 4C (170.2 mg, 0.242 mmol) in 15:15:1 (v/v/v) acetic acid/tetrahydrofuran/water (4 mL) was heated at reflux for 90 minutes. The solvent was evaporated under reduced pressure, and toluene was added and evaporated. Recrystallization from ethanol/hexane afforded 80.3 mg (72%) of the desired product. m.p. 203°–204° C. TLC (10% methanol/90% chloroform) $R_f=0.39$. $^1$H NMR (DMSO-d$_6$, 300 MHz) d 0.79 (t, 3H), 1.21 (t, 3H), 1.11–1.23 (m, 2H), 1.37–1.49 (m, 2H), 3.18 (t, 2H), 3.70 (s, 3H), 4.16 (q, 2H), 4.48 (s, 2H), 7.00 (d, 2H), 7.22 (d, 2H), 7.50–7.70 (m, 5H). MS (DCl/NH$_3$) m/e 460 (M+H)$^+$. Anal calcd for C$_{25}$H$_{29}$N$_7$O$_2$.0.45 H$_2$O: C, 64.21;H, 6.44; N, 20.97. Found: C, 64.57; H, 6.24; N, 20.53.

EXAMPLE 5 tert-Butyl 4-{N-butyl-N-[(2'-[1H-tetrazol-5-yl]biphenyl-4-yl)methyl]amino}-1-(N-ethyl)imidazole-5-carboxylate

Example 5A tert-Butyl 2-(cyanoimino)thiazolidine-3-yl-acetate 2-(Cyanoimino)thiazolidine (6.35 g, 49.9 mmol), prepared by the procedure of Neidlein and Reuter, Arch. Pharm. (Weinheim, Ger.) 305, 731 (1972), was added to a suspension of sodium hydride (2.04 g, 51 mmol, prewashed with hexane)in dimethylformamide (100 mL) at ambient temperature, resulting in heat and gas evolution. After stirring the mixture 30 minutes, tert-butyl bromoacetate (10.0 g, 51.3 mmol) was added and the resulting mixture was stirred 2.5 hours at ambient temperature. After removing the solvent in vacuo, the residue was partitioned between saturated sodium bicarbonate and methylene chloride and the aqueous phase extracted with additional methylene chloride (2×). The combined organic extracts were dried over sodium sulfate, filtered and concentrated in vacuo. Subsequent recrystallization from methylene chloride/hexane (1:4) afforded 9.04 g (75%) of the title compound as a white crystalline solid. m.p. 143°–144° C. TLC (ethyl acetate) $R_f=0.44$. $^1$H NMR (CDCl$_3$, 300 MHz) d 1.48 (s, 9H), 1.48 (s, 9H), 3.43 (t, 2H), 3.98 (t, 2H), 4.08 (s, 2H). MS (DCl/NH$_3$) m/e 242 (M+H)$^+$. Anal calcd for C$_{10}$H$_{15}$N$_3$O$_2$S.0.25 H$_2$O: C, 48.86; H, 6.36; N, 17.09. Found: C, 48.71; H, 5.98; N, 16.93.

EXAMPLE 5B tert-Butyl (6-amino-2,3-dihydroimidazo[2,1-b]thiazole)-5-carboxylate To a solution of the compound resulting from Example 5A in tert-butanol at ambient temperature was added potassium tert-butoxide (2.6 g, 23 mmol). After stirring the mixture at reflux for 1.5 hours, the mixture was concentrated in vacuo, quenched with saturated sodium bicarbonate (25 mL), diluted with water and extracted with methylene chloride (2×). The combined organic extracts were then dried over sodium sulfate, filtered and evaporated under reduced pressure to give 8.2 g of a reddish-brown solid. Subsequent recrystallization from ethyl acetate/hexane (2:3) afforded 5.92 g (66%) of the title compound as a tan crystalline solid. m.p. 151°–152° C. TLC (50% ethyl acetate/50% hexane) $R_f=0.19$. $^1$H NMR (CDCl$_3$, 300 MHz) d 1.56 (s, 9H), 3.75 (t, 2H), 4.22–4.38 (br, 2H). MS (DCl/NH$_3$) m/e 242 (M+H)$^+$. Anal calcd for C$_{10}$H$_{15}$N$_3$O$_2$S: C, 49.77; H, 6.27; N, 17.41. Found: C, 49.51; H, 6.11; N, 17.29.

Example 5C tert-Butyl 6-butylamino-2,3-dihydroimidazo[2,1-b]thiazole-5-carboxylate A solution of 1.0M sodium bis(trimethylsilyl)amide in tetrahydrofuran (25 mL, 25 mmol) was added to a solution of the compound resulting from Example 5B (5.9 g, 24 mmol) in N,N-dimethylformamide at 0° C. After 1 hour, 1-iodobutane (2.9 mL, 25 mmol) was added and the reaction was stirred at ambient temperature for 18 hours. The mixture was concentrated in vacuo and the residue was diluted with ethyl acetate. This solution was washed with water (2×) and brine, dried over sodium sulfate, filtered and concentrated under reduced pressure to afford 7.64 g of an oil. Chromatography on silica gel eluting with 20% ethyl acetate in hexane afforded 4.4 g (62%) of the title compound as an oil which slowly crystallized upon standing. TLC (50% ethyl acetate/50% hexane) $R_f=0.47$. $^1$H NMR (CDCl$_3$, 300 MHz) d 0.93 (t, 3H), 1.32–1.48 (m, 2H), 1.55 (s, 9H), 1.50–1.67 (m, 2H), 3.33–3.44 (m, 2H), 3.73 (t, 2H), 4.20–4.35 (m, 2H). MS (DCl/NH$_3$) m/e 298 (M+H)$^+$. Anal calcd for C$_{14}$H$_{23}$N$_3$O$_2$S: C, 56.54; H, 7.79; N, 14.13. Found: C, 56.35; H, 7.58; N, 13.93.

Example 5D tert-Butyl 4-butylamino-1-(N-ethyl)imidazole-5-carboxylate

The compound resulting from Example 5C (669 mg, 2.25 mmol) and W-2 Raney nickel (6 mL, 50% slurry in water)in ethanol (10 mL) were agitated in an ultrasonic cleaning bath at 50° C. for 1.5 hours. Sonication was continued for an additional 3 hours at 55° C. adding additional Raney nickel (ca 2 mL, 50% in water) every hour. Filtration followed by concentration of the filtrate under reduced pressure afforded 590 mg (98%) of an opaque oil which was carried on without further purification. TLC (ethyl acetate) $R_f=0.42$. $^1$H NMR (DMSO-$d_6$, 300 MHz) d 0.39 (t, 3H), 1.25 (t, 3H), 1.51 (s, 9H), 3.22-3.33 (m, 2H), 4.06 (q, 2H), 5.04-5.15 (br, 1H), 7.47 (s, 1H). MS (DCI/NH$_3$)m/e 268 (M+H)$^+$.

Example 5E tert-Butyl 4-{N-butyl-N-[(2'-[N-triphenylmethyl-1H-tetrazol-5-yl]biphenyl-4-yl)methyl]amino}-1-(N-ethyl)imidazole-5-carboxylate To the compound resulting from Example 5D (580 mg, 2.17 mmol) in tetrahydrofuran (5 mL) at 0° C. was added 1,3-dimethyl-3,4,5,6-tetrahydro2(1H)-pyrimidinone (1.4 mL, 12 mmol) followed by a solution of 1.0M lithium bis(trimethylsilyl)amide in tetrahydrofuran (2.2 mL, 2.2 mmol). After 30 minutes, triphenylmethyl-5-[2-(4'-bromomethylbiphenyl)]tetrazole (1.5 g, 2.2 mmol, 83% pure), prepared by the method described by Aldrich, P. E. et al. European Patent Application 291969, was added and the reaction was stirred at ambient temperature for 19 hours. The mixture was concentrated under reduced pressure, partitioned between saturated aq. NaHCO$_3$ and ethyl acetate and extracted with additional ethyl acetate (2×). The combined organic extracts were washed with water and brine, dried over sodium sulfate and evaporated under reduced pressure. Chromatography of the residue on silica gel eluting with 25% ethyl acetate in hexane afforded 883 mg (55%) of the desired product as a foam. TLC (25% ethyl acetate/75% chloroform) $R_f=0.57$. $^1$H NMR (CDCl$_3$, 300 MHz) d 0.82 (t, 3H), 1.39 (t, 3H), 1.57 (s, 9H), 3.22 (t, 2H), 4.29 (q, 2H), 4.47 (s, 2H), 6.87-7.53 (br envelope, 23H), 7.87 (dd, 1H). MS (DCl/NH$_3$)m/e 744 (M+H)$^+$.

Example 5F tert-Butyl 4-{N-butyl-N-[(2-[1H-tetrazol-S-yl]biphenyl-4-yl)methyl]amino}-1-(N-ethyl)imidazole-5-carboxylate The compound resulting from Example 5E (290 mg, 0.39 mmol) in 15:15:1 (v/v/v) acetic acid/tetrahydrofuran/water (25 mL) was heated at reflux for 8 hours. The solvent was concentrated under reduced pressure, and toluene was added and evaporated. Chromatography on silica gel eluting with 2% methanol in chloroform afforded 155 mg (79%) of the desired product: m.p. 190°-191° C. TLC (15% methanol/85% chloroform) $R_f=0.52$. $^1$H NMR (CDCl$_3$, 300 MHz) d 0.87 (t, 3H), 1.36-1.19 (m, 2H), 1.42 (t, 3H), 1.60 (s, 9H), 3.24 (t, 2H), 4.27 (q, 2H), 4.35 (s, 2H), 7.03 (d, 2H), 7.11 (d, 2H), 7.41-7.63 (m, 4H), 8.02 (dd, 1H). MS (DCl/NH$_3$)m/e 502 (M+H)$^+$. Anal calcd for C$_{28}$H$_{35}$N$_7$O$_2$.0.55 H$_2$O: C, 65.74; H, 7.11; N, 19.17. Found: C, 66.07; H, 6.73; N, 18.77.

EXAMPLE 6

4-{N-Butyl-N-[(2'-[1H-tetrazol-5-yl]biphenyl-4-yl)methyl]amino}-1-(N-ethyl)imidazole To a solution of the compound resulting from Example 5F (40 mg, 0.090 mmol) in methylene chloride (1 mL) at ambient temperature was added trifluoroacetic acid (1 mL), and the resulting solution was allowed to stir 3 hours at ambient temperature. After removing the solvent in vacuo, the residue was diluted with brine, adjusted to pH to 3-4 by the dropwise addition of saturated aqueous sodium bicarbonate and extracted several times with methylene chloride. The combined organic extracts were then dried over sodium sulfate, filtered and evaporated under reduced pressure to give 42 mg of a foam. Chromatography on silica gel, eluting first with 3% methanol in chloroform followed by 7% methanol in chloroform, afforded 25 mg (69%) of the title compound as a foam. TLC (15% methanol/85% chloroform) $R_f=0.24$. $^1$H NMR (CDCl$_3$, 300 MHz) d 0.93 (t, 3H), 1.20-1.45 (m, 2H), 1.52 (t, 3H), 1.55-1.70 (m, 2H), 3.23 (t, 2H), 4.02 (q, 2H), 4.41 (s, 2H), 6.14 (s, 1H), 6.95-7.13 (2d, 4H), 7.38-7.64 (m, 4H), 7.71 (s, 1H), 7.92 (dd, 1H). Exact mass (C$_{23}$H$_{28}$N$_7$, M+H) Calcd: 402.2406. Found: 402.2405.

EXAMPLE 7

Ethyl 5-{N-butyl-N-[(2'-[1H-tetrazol-5-yl]biphenyl-4-yl)methyl]amino}-1-methylimidazole-4-carboxylate Example 7A Ethyl 5-amino-1-methylimidazole-4-carboxylate A solution of ethyl 5-amino-2-mercapto-1-methylimidazole-4-carboxylate (1.0 g, 5.0 mmol), prepared by the method of Cook, Downer, and Heilbron, J. Chem. Soc. 2028.(1948), and W-2 Raney nickel (2 mL, 50% slurry in water)in ethanol (20 mL) were agitated in an ultrasonic cleaning bath at 50° C. for 1 hour. Sonication was continued for an additional 2 hours at 55° C. adding additional Raney nickel (ca 2 mL, 50% in water) every hour. Filtration followed by evaporation under reduced pressure afforded 0.81 g (96%) of the title compound as a tan crystalline solid which was used without further purification. m.p. 193°-194° C. TLC (10% methanol/90% ethyl acetate) $R_f=0.19$. $^1$H NMR (CDCl$_3$, 300 MHz) d 1.39 (t, 3H), 3.46 (s, 3H), 4.34 (q, 2H), 4.75-4.95 (br, 2H), 7.01 (s, 1H). MS (DCl/NH$_3$) m/e 170 (M+H)$^+$. Anal calcd for C$_7$H$_{11}$N$_3$O$_2$.0.20 H$_2$O: C, 48.66; H, 6.65; N, 24.32. Found: C, 48.98; H, 6.54; N, 24.12.

Example 7B

Ethyl 5-butylamino-1-methylimidazole-4-carboxylate

To the compound resulting from Example 7A (690 mg, 4.08 mmol) in dimethylformamide (8 mL) at 0° C. was added a solution of 1.0M sodium bis(trimethylsilyl)amide in tetrahydrofuran (4.1 mL, 4.1 mmol). After 1 hour, 1-iodobutane (1.75 mL, 15.4 mmol) was added, and the reaction was stirred at ambient temperature for 20 hours. The mixture was diluted with saturated aqueous sodium bicarbonate and extracted with ethyl acetate (6×). The combined organic extracts were washed with water (2×) and brine, dried over sodium sulfate, filtered and evaporated to give 774 mg of an oil which was used without further purification. TLC (10% methanol/90% ethyl acetate) $R_f=0.21$. $^1$H NMR (CDCl$_3$, 300 MHz) d 0.93 (t, 3H), 1.39 (t, 3H), 3.15 (q, 2H), 3.56 (s, 3H), 4.34 (q, 2H), 5.38-5.53 (br, 1H), 7.05 (s, 1H). MS (DCl/NH$_3$) m/e 226 (M+H)$^+$.

Example 7C

Ethyl 5-{N-butyl-N-[(2'-[N-triphenylmethyl-1H-tetrazol-5-yl]biphenyl-4-yl)methyl]amino}-1-methylimidazole-4-carboxylate To the compound resulting from Example 7B (674 mg, 2.99 mmol) in tetrahydrofuran (6 mL) at 0° C. was added 1,3-dimethyl-3,4,5,6-tetrahydro 2(1H)-pyrimidinone (1.9 mL, 16 mmol) followed by a solution of 1.0M lithium bis(trimethylsilyl)amide in tetrahydrofuran (3.0 mL, 3.0 mmol). After 1 hour N-triphenylmethyl-5-[2-(4'-bromomethylbiphenyl)]tetrazole (2.03 g, 2.99 mmol, 83% pure), prepared by the procedure of Aldrich, P. E. et al. European Patent Application 291969, was added and the reaction was stirred at ambient temperature for 18 hours. The mixture was evaporated under reduced pressure, taken up in saturated aqueous sodium bicarbonate and extracted with ethyl acetate (3×). The combined organic extracts were washed with water and brine, dried over sodium sulfate and concentrated under reduced pressure. Chromatography of the residue on silica gel eluting with 50% ethyl acetate in hexane followed by 75% ethyl acetate in hexane afforded 1.12 g (53%), of the title compound as a foam. TLC (ethyl acetate) $R_f=0.35$. $^1$H NMR (CDCl$_3$, 300 MHz) d 0.83 (t, 3H), 1.45 (t, 3H), 3.10 (s, 3H), 3.13 (t, 3H), 4.16 (s, 2H), 4.42 (q, 2H), 6.90–7.55 (br envelope, 23H), 7.86 (dd, 1H). MS (DCl/NH$_3$) m/e 702 (M+H)$^+$.

Example 7D

Ethyl 5-{N-butyl-N-[(2'-[1H-tetrazol-5-yl]biphenyl-4-yl)methyl]amino}-1-methylimidazole-4-carboxylate The compound resulting from Example 7C (465 mg, 0.66 mmol) in (v/v/v) 15:15:1 acetic acid/tetrahydrofuran/water (15 mL) was heated at reflux for 2 hours. The solvent was evaporated under reduced pressure, and toluene was added and evaporated. Chromatography of the residue on silica gel eluting with 2–10% methanol in chloroform (by gradients of 2%) and then with 15% methanol in chloroform afforded 298 mg (98%) of the title compound as a pale-yellow solid. TLC (15% methanol/85% chloroform) $R_f=0.60$; $^1$H NMR (CDCl$_3$, 300 MHz) d 0.89 (t, 3H), 1.36 (t, 3H), 3.04–3.25 (m, 5H), 4.13 (s, 2H), 4.32–4.50 (m, 2H), 6.70–6.95 (m, 4H), 7.21–7.67 (br envelope, 6H). MS (DCl/NH$_3$) m/e 460 (M+H)$^+$. Exact mass (C$_{25}$H$_{30}$N$_7$O$_2$, M+H)Calcd: 460.2461. Found: 460.2460.

EXAMPLE 8

5-{N-Butyl-N-[(2'-[1H-tetrazol-5-yl]biphenyl-4-yl)methyl]amino}-1-methylimidazole-4-carboxylic acid The compound resulting from Example 7 (150 mg, 0.33 mmol) in 1M aqueous potassium hydroxide solution (5 mL) was stirred for 48 hours at ambient temperature. The mixture was acidified to pH 3–4 with 2M hydrochloric acid and extracted with chloroform (5×). The combined organic extracts were dried over sodium sulfate, filtered and evaporated under reduced pressure to afford 150 mg of a pale-yellow foam solid which was triturated with ether to afford 130 mg (91%) of the title compound as a pale-yellow powder. TLC (25% acetic acid/25% ethyl acetate/25% n-butanol/25% water) $R_f=0.72$. $^1$H NMR (DMSO-d$_6$, 300 MHz) d 0.80 (t, 3H), 1.13–1.37 (m, 4H), 3.07 (t, 3H), 3.25 (s, 3H), 4.20 (s, 2H), 7.00 (d, 2H), 7.13 (d, 2H), 7.48–7.76 (m, 5H). MS (DCl/NH$_3$) m/e 432 (M+H)$^+$. Anal calcd for C$_{23}$H$_{25}$N$_7$O$_2$.1.25 H$_2$O: C, 60.85; H, 6.10; N, 21.60. Found: C, 60.78; H, 5.71; N, 20.16.

EXAMPLE 9

Ethyl 5-{N-butyl-N-[(2'-[1H-tetrazol-5-yl]biphenyl-4-yl)methyl]amino}-1,2,3-thiadiazole-4-carboxylate

EXAMPLE 9A

Ethyl 5-{N-butyl-N-[(2'-[N-triphenylmethyl-1H-tetrazol-5-yl]biphenyl-4-yl)methyl]amino}-1,2,3-thiadiazole-4-carboxylate A solution of ethyl 5-chloro-1.2.3-thiadiazole-4-carboxylate (500 mg, 2.60 mmol), prepared by the method of Demaree et al. Can. J. Chem. 55, 243 (1977), N-triphenylmethyl-5-[2-[4'-(butylamino)methylbiphenyl]-]tetrazole (1.60 g, 2.91 mmol), the compound resulting from Example 11A, and triethylamine (1.10 mL, 7.89 mmol) in isopropanol (8 mL) was heated at 115° C. in a sealed tube for 3 hours. The mixture was cooled, concentrated in vacuo, diluted with 1M sodium hydroxide and extracted with ethyl acetate (2×). The combined organic extracts were then washed with brine (1×), dried over sodium sulfate, filtered and evaporated under reduced pressure to give 2.0 g of a foam. Chromatography of the residue on silica eluting with 15% ethyl acetate in hexane afforded 1.26 g (69%) of the title compound as a ta foam. TLC (50% ethyl acetate/50% hexane) $R_f=0.56$. $^1$H NMR (CDCl$_3$, 300 MHz) d 0.88 (t, 3H), 1.39 (t, 3H), 3.35 (t, 2H), 4.41 (q, 2H), 4.63 (s, 2H), 6.85–6.96 (m, 6H), 6.94 (d, 2H), 7.10 (d, 2H), 7.17–7.41 (m, 10H), 7.41–7.56 (m, 2H), 7.94 (dd, 1H). MS (DCl/NH$_3$) m/e 706 (M+H)$^+$.

Example 9B

Ethyl 5-{N-butyl-N-[(2'-[1H-tetrazol-5-yl]biphenyl-4-yl)methyl]amino}-1,2,3-thiadiazole-4-carboxylate The compound resulting from Example 9A (1.16 g, 1.64 mmol) in 15:15:1 (v/v/v) acetic acid/tetrahydrofuran/water (40 mL) was heated at reflux for 2 hours. The solvent was evaporated under reduced pressure, and toluene was added and evaporated. Chromatography of the residue on silica gel eluting first with 50% ethyl acetate in hexane and then with 3% methanol in chloroform followed by 5% methanol in chloroform afforded 687 mg (90%) of the title compound as a foam. TLC (15% methanol/85% chloroform) $R_f=0.42$. $^1$H NMR (CDCl$_3$, 300 MHz) d 0.94 (t, 3H), 1.36 (t, 3H), 1.62–1.77 (m, 2H), 3.50 (t, 2H), 4.35 (q, 2H), 4.84 (s, 2H), 7.13–7.30 (m, 4H), 7.41 (dd, 1H), 7.50–7.66 (m, 2H), 8.13 (dd, 1H). MS (DCl/NH$_3$) m/e 464 (M+H)$^+$. Anal calcd for C$_{23}$H$_{25}$N$_7$O$_2$S.1.0 H$_2$O: C, 57.36; H, 5.65; N, 20.36. Found: C, 57.75; H, 5.26; N, 19.98.

EXAMPLE 10

5-[N-Butyl-N-[[2'-(1H-tetrazol-5-yl)biphenyl-4-yl]methyl]amino]-1,2,3-thiadiazole-4-carboxylic acid The compound resulting from Example 9 in 1M aqueous potassium hydroxide solution (5 mL) was stirred for 24 hours at ambient temperature. The mixture was acidified to pH 3–4 with 2M hydrocloric acid and extracted with chloroform (5×). The combined organic extracts were then dried over sodium sulfate, filtered and evaporated under reduced pressure to afford 150 mg (100%) of the title compound as a foam. TLC (10% methanol/1% acetic acid/84% chloroform) $R_f=0.24$. $^1$H NMR (CDCl$_3$, 300 MHz) d 0.94 (t, 3H), 1.20–1.43 (m, 2H), 1.67–1.90 (br, 2H), 3.35–3.60 (br, 2H), 4.82–5.12 (br, 2H), 6.80–7.29 (br, 4H), 7.41 (dd, 1H), 7.47–7.65 (m, 2H), 7.84–8.06 (br, 1H). MS (DCl/NH$_3$) m/e 436 (M+H)$^+$. Anal calcd for C$_{21}$H$_{21}$N$_7$O$_2$S: C, 57.92; H, 4.86; N, 22.51. Found: C, 58.13; H, 5.14; N, 21.42.

EXAMPLE 11

Ethyl 2-{N-Butyl-N-[(2'-[1H-tetrazol-5-yl]biphenyl-4-yl)methyl]amino}-1,3,4-thiadiazole-5-carboxylate

Example 11A

N-Triphenylmethyl-5-[2-(4'-butylaminomethyl-biphenyl)]tetrazole

To N-Triphenylmethyl-5-[2-(4'-bromomethyl-biphenyl)]tetrazole (6.00 g, 10.7 mmol), prepared as described by P. E. Aldrich et al in European Patent Application Number 291969, published Nov. 23, 1988, dissolved in tetrahydrofuran (55 mL) was added n-butylamine (40 mL). The reaction mixture was stirred at room temperature for 2 hours and then concentrated in vacuo. The residue obtained was dissolved in chloroform, washed with dilute potassium hydroxide solution, dried over potassium carbonate and concentrated under reduced pressure to afford the title compound.

Example 11B

Ethyl 2-{N-Butyl-N-[(2'-[N-triphenylmethyl-1H-tetrazol-5-yl]biphenyl-4-yl)methyl]amino}-1,3,4-thiadiazole-5-carboxylate A solution of ethyl 2-chloro-1,3,4-thiadiazole-5-carboxylate (500 mg, 2.60 mmol), prepared by the method of Demaree et al. Can. J. Chem. 55, 243 (1977), the compound resulting from Example 11A (1.60 g, 2.91 mmol) and triethylamine (1.10 mL, 7.89 mmol) in isopropanol (8 mL) was heated at 115° C. in a sealed tube for 3 hours. The mixture was cooled, concentrated under reduced pressure, diluted with 1M sodium hydroxide and extracted with ethyl acetate (2×). The combined organic extracts were then washed with brine (1×), dried over sodium sulfate, filtered and evaporated under reduced pressure to give 1.9 g of a foam which contained a mixture of ethyl and isopropyl esters. Chromatography on silica eluting with 15% ethyl acetate in hexane followed by 20% ethyl acetate in hexane gave partial separation of the two esters affording 1.26 g (23%) of the pure ethyl ester title compound as a foam. TLC (50% ethyl acetate/50% hexane) $R_f=0.51$. $^1$H NMR (CDCl$_3$, 300 MHz) d 0.91 (t, 3H), 1.18–1.38 (m, 2H), 1.40 (t, 3H), 1.51–1.69 (m, 2H), 3.33 (t, 2H), 4.43 (q, 2H), 4.67 (s, 2H), 6.84–6.95 (m, 6H), 7.03 (d, 2H), 7.11 (d, 2H), 7.17–7.41 (m, 10H), 7.41–7.56 (m, 2H), 7.96 (dd, 1H). MS (DCl/NH$_3$)m/e 706 (M+H)$^+$.

Example 11C

Ethyl 2-{N-Butyl-N-[(2'-[1H-tetrazol-5-yl]biphenyl-4-yl)methyl]amino}-1,3,4-thiadiazole-5-carboxylate The compound resulting from Example 11B (374 mg, 0.53 mmol) in 15:15:1 (v/v/v) acetic acid/tetrahydrofuran/water (5 mL) was heated at reflux for 2 hours.

The solvent was evaporated under reduced pressure, and toluene was added and evaporated. Chromatography of the residue on silica gel eluting first with 40% ethyl acetate in hexane and then with 3% methanol in chloroform followed by 5% methanol in chloroform afforded 198 mg (81%) of the title compound as a foam. TLC (15% methanol/85% chloroform) $R_f=0.42$. $^1$H NMR (CDCl$_3$, 300 MHz) d 0.97 (t, 3H), 1.40 (t, 3H), 1.63–1.79 (m, 2H), 3.53 (t, 2H), 4.42 (q, 2H), 4.81 (s, 2H), 7.18 (d, 2H), 7.29 (d, 2H), 7.41 (dd, 1H), 7.48–7.64 (m, 2H), 8.09 (dd, 1H). MS (DCl/NH$_3$) m/e 464 (M+H)$^+$. Anal calcd for C$_{23}$H$_{25}$N$_7$O$_2$S.0.25 H$_2$O: C, 59.02; H, 5.49; N, 20.94. Found: C, 58.94; H, 5.30; N, 20.52.

EXAMPLE 12

2-{N-Butyl-N-[(2'-[1H-tetrazol-5-yl]biphenyl-4-yl)methyl]amino}-1,3,4-thiadiazole The compound resulting from Example 11 (101 mg, 0.22 mmol) in 1M aqueous potassium hydroxide solution (4 mL) was stirred for 24 hours at ambient temperature. The mixture was acidified to pH 3–4 with 2M hydrochloric acid and extracted with chloroform (5×). The combined organic extracts were then dried over sodium sulfate, filtered and concentrated in vacuo to afford 88 mg (100%) of the title compound as a foam. TLC (10% methanol/1% acetic acid/84% chloroform) $R_f=0.41$. $^1$H NMR (CDCl$_3$, 300 MHz) d 0.95 (t, 3H), 1.26–1.45 (m, 2H), 1.62–1.78 (m, 2H), 3.50 (t, 2H), 4.77 (s, 2H), 7.17 (d, 2H), 7.28 (d, 2H), 7.41 (dd, 1H), 7.48–7.64 (m, 2H), 8.08 (dd, 1H), 8.35 (s, 1H). MS (DCl/NH$_3$)m/e 392 (M+H)$^+$. Anal calcd for C$_{20}$H$_{21}$N$_7$S.0.5 H$_2$O: 59.98; H, 5.54; N, 24.48. Found: C, 60.23; H, 5.42; N, 23.75.

EXAMPLE 13

Ethyl 1-methyl-3-{N-propyl-N-[(2'-[1H-tetrazol-5-yl]biphenyl-4-yl)methyl]amino}pyrazole-4-carboxylate

Example 13A

Ethyl 3-allylamino-1-methylpyrazole-4-carboxylate

Ethyl 3-amino-1-methylpyrazole-4-carboxylate, prepared by the method of Schmidt et al., Helvetica Chim. Acta. 42 349 (1959), (12.5 g, 7.40 mmol) was dissolved in 80 mL of 1,3-dimethyl-3,4,5,6-tetrahydro2(1H)-pyrimidinone (DMPU) and cooled to −40° C. A 1M solution of sodium hexamethyldisilazide in tetrahydrofuran (80 mL, 8.0 mmol) was added dropwise. After 8 minutes at −35° C., the reaction was cooled to −40° C. and 13.16 g (10.8 mmol) of allyl bromide was added dropwise. The reaction mixture was allowed to warm to 10° C. over 90 minutes. Water was added and the mixture was extracted with ether. The combined organic extracts were washed with water (3×), dried over sodium sulfate and concentrated in vacuo to afford a mixture of mono- and di-allyl products plus 10% unreacted starting material. Separation by column chromatography on silica gel eluting with 30% ethyl acetate in hexane afforded 5.26 g (34%) of the title compound as a colorless oil.

Example 13B

Ethyl 3-propyl-1-methylpyrazole-4-carboxylate

The compound resulting from Example 13A was hydrogenated at 4 atmospheres of hydrogen in 100 mL of ethanol and 100 mL of ethyl acetate using 260 mg of platinum oxide catalyst to afford the title compound (5.02 g) as a colorless oil.

Example 13C

Ethyl 1-methyl-3-{N-propyl-N-[(2'-[N-triphenylmethyl-1H-tetrazol-5-yl]biphenyl-4-yl)methyl]amino}pyrazole-4-carboxylate The compound resulting from Example 13B (900 mg, 4.26 mmol) was dissolved in 2.5 mL of 1,3-dimethyl-3,4,5,6-tetrahydro-2(1H)-pyrimidinone (DMPU) and 1.5 mL of tetrahydrofuran at $-35°$ C. A solution of 4.27 mL of 1M solution of lithium hexamethyldisilazide in tetrahydrofuran (80 mL, 8.0 mmol) was added dropwise. The solution was stirred at $-35°$ C. for 10 minutes and then cooled to $-40°$ C. A solution of N-triphenylmethyl-5-[2-(4'-bromomethyl-biphenyl)]tetrazole (2.30 g, 4.13 mmol) in 6 mL of tetrahydrofuran was added dropwise. The solution was allowed to warm to ambient temperature over 90 minutes and then toluene was added. The mixture was washed three times with water, dried over sodium sulfate and concentrated under reduced pressure. The residue obtained was chromatographed on silica gel eluting with 10% ethyl acetate in toluene to afford 2.61 g of the title compound.

Example 13D

Ethyl 1-methyl-3-{N-propyl-N-[(2'-[1H-tetrazol-5-yl]biphenyl-4-yl)methyl]amino}pyrazole-4-carboxylate The compound resulting from Example 13C (2.61 g) was dissolved in 22 mL of methylene chloride and 33 mL of 88% formic acid. After 2 hours at ambient temperature, the solvents were removed in vacuo. 50% Formic acid was added and the mixture filtered to remove triphenylmethanol. The filtrate was concentrated in vacuo, water was added, and the mixture was concentrated again in vacuo. The residue was dissolved in chloroform, washed with water, dried over sodium sulfate and concentrated in vacuo to give the title compound (1.58 g). $^1$H NMR (CDCl$_3$, 300 MHz) d 0.85 (t, J=7Hz, 3H), 1.31 (t, J=7Hz, 3H), 1.57 (m, 2H), 3.25 (t, J=7Hz, 2H), 3.66 (s, 3H), 4.22 (q, J=7Hz, 2H), 4.48 (s, 2H), 7.07 (d, J=8Hz, 2H), 7.28 (d, J=8Hz, 2H), 7.43 (dd, J=8Hz, 2Hz, 1H), 7.50-7.60 (m, 2H), 7.75 (sa, 1H), 8.12 (dd, J=8Hz, 2Hz, 1H).

EXAMPLE 14

1-Methyl-3-{N-propyl-N-[(2'-[1H-tetrazol-5-yl]biphenyl-4-yl)methyl]amino}pyrazole-4-carboxylic acid The compound resulting from Example 13 (1.21 g, 2.72 mmol) was refluxed for 1 hour in 44 mL of ethanol and 10 mL of water containing 1.10 g of sodium hydroxide. The solution was cooled in an ice bath, neutralized with acetic acid and concentrated in vacuo. Water was added and the mixture was acidified with formic acid. The resulting solid was filtered, dissolved in chloroform, dired over sodium sulfate and concentrated in vacuo. The residue obatined was crystallized from ether to give 868 mg (76%) of the title compound. m.p. 101°-105° C. $^1$H NMR (DMSO-d$_6$, 300 MHz) d 0.72 (t, J=7Hz, 3H), 1.47 (m, 2H), 3.13 (t, J=7Hz, 2H), 3.67 (s, 3H), 4.50 (s, 2H), 7.01 (d, J=8Hz, 2H), 7.22 (d, J=8Hz, 2H), 7.50-7.70 (m, 4H), 8.01 (s, 1H), 11.75 (broad, 1H).

EXAMPLE 15

Ethyl 5-methyl-3-{N-propyl-N-[(2'-[1H-tetrazol-5-yl]biphenyl-4-yl)methyl]amino}isoxazole-4-carboxylate

Example 15A

Ethyl 5-methyl-3-propylaminoisoxazole-4-carboxylate

Ethyl 5-methylisoxazole-4-carboxylate is quaternized with propyl benzenesulfonate and the resulting quaternary salt is reacted with hydroxylamine to give the title compound according to the procedure of A. Alberola et al., Synthesis 203 (1988).

Example 15B

Ethyl 5-methyl-3-{N-propyl-N-[(2'-[1H-tetrazol-5-yl]biphenyl-4-yl)methyl]amino}isoxazole-4-carboxylate The compound resulting from Example 15A is reacted with N-triphenylmethyl-5-[2-(4'-bromomethyl-biphenyl)]tetrazole according to the procedure described in Example 13C to give the N-triphenylmethyl-protected adduct. This compound is deprotected with formic acid by the procedure described in Example 13D to give the title compound.

EXAMPLE 16

5-Methyl-3-{N-propyl-N-[(2'-[1H-tetrazol-5-yl]biphenyl-4-yl)methyl]amino}isoxazole-4-carboxylic acid The compound resulting from Example 15 is hydrolyzed by the procedure described in Example 14 to afford the title compound.

EXAMPLE 17

5-Butylimino-4,5-dihydro-4-ethoxycarbonyl-4-[[2'-(1H-tetrazol-5-yl)biphenyl-4-yl]methyl]thiazole 5-Butylimino-4,5-dihydro-4-ethoxycarbonyl-4-[[2'-(N-triphenylmethyl-1H-tetrazol-5-yl)biphenyl-4-yl]methyl]thiazole, the compound resulting from Example 2A (B), (170 mg, 0.241 mmol) in 15:15:1 (v/v/v) acetic acid/tetrahydrofuran/water (4 mL) was heated at reflux for 90 minutes. The solvent was evaporated under reduced pressure, and toluene was added and evaporated. Chromatography of the residue on silica gel eluting with 2-6% methanol in chloroform afforded 33.6 mg (30%) of the desired product as a yellow foam solid. TLC (10% methanol/90% chloroform) R$_f$=0.33. $^1$H NMR (CDCl$_3$, 300 MHz) d 0.88 (t, 3H), 1.23 (t, 3H), 1.10-1.65 (envelope, 4H), 3.61 (d, 1H), 3.75 (dt, 2H), 3.81 (d, 1H), 4.08-4.32 (m, 2H), 7.08 (d, 2H), 7.27 (d, 2H), 7.38 (dd, 1H), 7.50-7.63 (m, 2H), 7.75 (s, 1H), 8.20 (dd, 1H). MS (DCI/NH$_3$) m/e 463 (M+H)$^+$. Anal calcd for C$_{24}$H$_{26}$N$_6$O$_2$S.0.25 H$_2$O: C, 61.72; H, 5.72; N, 17.99. Found: C, 61.89; H, 5.32; N, 17.76.

EXAMPLE 18

5-Butylimino-4-carboxy-4,5-dihydro-4-[[2'-(1H-tetrazol-5-yl)biphenyl-4-yl]methyl]thiazole The compound resulting from Example 17 (52.2 mg, 0.113 mmol) in 1M aqueous potassium hydroxide solution (2 mL) was stirred for 2 hours at ambient temperature. The mixture was acidified with 2M hydrochloric acid and decanted. The resulting gummy solid was dissolved in chloroform, dried over sodium sulfate and evaporated with hexane chases to afford 42.2 mg (86%) of the desired product as a foam. TLC (25% acetic acid/25% ethyl acetate/25% n-butanol/25% water) R$_f$=0.70. MS (DCI/NH$_3$) m/e 435 (M+H)$^+$. Anal calcd for C$_{22}$H$_{22}$N$_6$O$_2$S.0.75 H$_2$O: C, 58.98; H, 5.29; N, 18.76. Found: C, 68.99; H, 5.61; N, 18.43.

EXAMPLE 19

Ethyl 5-[N-butyl-N-[[2'-(1H-tetrazol-5-yl)biphenyl-4-yl]methyl]amino]-1-methylpyrazole-4-carboxylate

Example 19A

Ethyl 5-butylamino-1-methylpyrazole-4-carboxylate

To ethyl 5-amino-1-methylpyrazole-4-carboxylate (3.4476 g, 20.38 mmol) in dimethylformamide (60 mL) at 0° C. was added a solution of 1.0M sodium bis(trimethylsilyl)amide in tetrahydrofuran (20.5 mL, 20.5 mmol). After 1 hour, 1-iodobutane (2.50 mL, 22.0 mmol) was added and the reaction was stirred at ambient temperature for 20 hours. The mixture was diluted with saturated aqueous sodium bicarbonate and extracted with ethyl acetate (6×). The combined organic extracts were then washed with water (2×) and brine, dried over sodium sulfate, filtered and evaporated under reduced pressure. Chromatography of the residue on silica gel eluting with 20% ethyl acetate in hexane afforded 3.8754 g (84%) of the desired product as a oil. TLC (20% ethyl acetate/80% hexane) R$_f$=0.12. $^1$H NMR (CDCl$_3$, 300 MHz) d 0.94 (t, 3H), 1.33 (t, 3H), 1.35–1.50 (m, 2H), 1.53–1.65 (m, 2H), 3.25 (t, 2H), 3.77 (s, 3H), 4.25 (q, 2H), 5.60–5.80 (br, 1H), 7.62 (s, 1H). MS (DCI/NH$_3$)m/e 226 (M+H)$^+$.

Example 19B

Ethyl 5-{N-butyl-N-[(2'-[N-triphenylmethyl-1H-tetrazol-5-yl]biphenyl-4-yl)methyl]amino}-1-methylpyrazole-4-carboxylate To the compound resulting from Example 19A (657 mg, 2.92 mmol) in tetrahydrofuran (10 mL) at 0° C. was added 1,3-dimethyl-3,4,5,6-tetrahydro-2(1H)-pyrimidinone (1.75 mL, 14.5 mmol) followed by a solution of 1.0M lithium bis(trimethylsilyl)amide in tetrahydrofuran (3.1 mL, 3.1 mmol). After 30 minutes triphenylmethyl-5-[2-(4'-bromomethylbiphenyl)]tetrazole (2.05 g, 3.0 mmol, 83% pure), prepared by the procedure of Aldrich, P. E. et al., European Patent Application 291969, was added and the reaction was stirred at ambient temperature for 18 hours. The mixture was evaporated under reduced pressure, taken up in saturated aqueous sodium bicarbonate, and extracted with ethyl acetate. The combined organic extracts were washed with water and brine, dried over sodium sulfate, and evaporated. Chromatography of the residue on silica gel eluting with 12–20% ethyl acetate in hexane afforded 1.921 g (94%) of the title compound as a foam. TLC (20% ethyl acetate/80% hexane) R$_f$=0.13. $^1$H NMR (CDCl$_3$, 300 MHz) d 0.82 (t, 3H), 1.40 (t, 3H), 3.08 (t, 3H), 3.53 (s, 3H), 4.15 (s, 2H), 4.32 (q, 2H), 6.85–7.38 (br envelope, 19H), 7.38 (dd, 1H), 7.40–7.53 (m, 2H), 7.84 (s, 1H), 7.89 (dd, 1H). MS (DCI/NH$_3$)m/e 702 (M+H)$^+$.

Example 19C

Ethyl 5-{N-butyl-N-[(2'-[1H-tetrazol-5-yl]biphenyl-4-yl)methyl]amino}-1-methylpyrazole-4-carboxylate The compound resulting from Example 19B (508 mg, 0.724 mmol) in 15:15:1 (v/v/v) acetic acid/tetrahydrofuran/water (10 mL) was heated at reflux for 90 minutes. The solvent was evaporated under reduced pressure, and toluene was added and evaporated. Chromatography of the residue on silica gel eluting with 2–4% methanol in chloroform afforded 285 mg (86%) of the title compound as a white foam. TLC (10% methanol/90% chloroform) R$_f$=0.39. $^1$H NMR (CDCl$_3$, 300 MHz) d 0.89 (t, 3H), 1.28 (t, 3H), 1.25–1.45 (m, 4H), 3.15 (t, 3H), 3.64 (s, 3H), 4.13 (q, 2H), 4.22 (s, 2H), 7.10 (s, 4H), 7.43 (dd, 1H), 7.49–7.63 (m, 2H), 7.82 (s, 1H), 8.18 (dd, 1H). MS (DCI/NH$_3$) m/e 460 (M+H)$^+$. Anal calcd for C$_{25}$H$_{29}$N$_7$O$_2$.0.5 H$_2$O: C, 64.09; H, 6.45; N, 20.93. Found: C, 64.16; H, 6.26; N, 20.59.

EXAMPLE 20

5-{N-Butyl-N-[(2'-[1H-tetrazol-5-yl]biphenyl-4-yl)methyl]amino}-1-(methyl)pyrazole-4-carboxylic acid The compound resulting from Example 19 (104.3 mg, 0.227 mmol) in 1M aqueous potassium hydroxide solution (4 mL) and ethanol (0.4 mL) was stirred for 32 hours at ambient temperature. The mixture was concentrated under reduced pressure, acidified with 2M hydrochloric acid and filtered. The resulting solid was dissolved in chloroform, dried over sodium sulfate and evaporated in vacuo to afford 94.6 mg (97%) of the desired product as a solid. TLC (1% acetic acid/5% methanol/94% chloroform) R$_f$=0.26. $^1$H NMR (CDCl$_3$, 300 MHz) d 0.90 (t, 3H), 1.20–1.48 (m, 4H), 3.25 (t, 3H), 3.82 (s, 3H), 4.15 (s, 2H), 7.12 (d, 2H), 7.18 (d, 2H), 7.38 (dd, 1H), 7.51–7.62 (m, 2H), 7.88 (s, 1H), 8.40 (dd, 1H). MS (DCI/NH$_3$) m/e 432 (M+H)$^+$. Anal calcd for C$_{23}$H$_{25}$N$_7$O$_2$: C, 64.02; H, 5.84; N, 22.72. Found: c, 64.37; H, 5.84; N, 23.08.

EXAMPLE 21

4-{N-Propyl-N-[(2'-[1H-tetrazol-5-yl]biphenyl-4-yl)methyl]amino}thiazole-5-carboxylic acid

Example 21A

N-Triphenylmethyl-5-[2-(4'-propylaminomethylbiphenyl)]tetrazole

To N-triphenylmethyl-5-[2-(4'-bromomethylbiphenyl)]tetrazole, prepared as described by P. E. Aldrich, et al., in European Patent Application Number 291969, (2.8 g, 5 mmol) dissolved in tetrahydrofuran (50 mL) was added n-propylamine (2.5 mL). The reaction was stirred for 4 hours at ambient temperature and then concentrated in vacuo. The residue obtained was dissolved in ethyl acetate, washed with water and saturated sodium chloride, dried over sodium sulfate and concentrated under reduced pressure to afford the title compound.

Example 21B

4-{N-Propyl-N-[(2'-[1H-tetrazol-5-yl]biphenyl-4-yl)methyl]amino}thiazole-5-carboxylic acid Ethyl 2-mercaptoacetate is reacted with dimethyl N-cyanodithioimino-carbonate under the action of N-ethyldiisopropylamine in dimethylformamide to give ethyl 4-amino-2-methylthiothiazole-5-carboxylate, according to the method of Gompper, et al., Tet. Letters, 1885 (1966). Selective desulfurization is accomplished by the procedure of Baldwin and Ponticello, J. Med. Chem., 23(1), 65 (1980) by stirring at ambient temperature with zinc dust in 3N hydrochloric acid. The resultant ethyl 4-aminothiazole-5-carboxylate is nitrosated by the slow addition of sodium nitrite to a solution in 48% hydrobromic acid containing copper (I) bromide to give ethyl 4-bromothiazole-5-carboxylate. Heating an ethanolic solution of the bromide with the compound resulting from Example 21A and N-ethyldiisopropylamine in a sealed tube by the procedure described in Example 11B gives the fully protected product. This compound is deprotected by the procedure described in Example 11C and hydrolyzed by the procedure described in Example 12 to give the title compound.

EXAMPLE 22

Ethyl 5-methyl-3-{N-Propyl-N-[(2'-[1H-tetrazol-5-yl]biphenyl-4-yl)methyl]amino}isothiazole-4-carboxylate Ethyl 3-amino-5-methylisothiazole-4-carboxylate, prepared by the method of Hartke and Peshkar, Arch. Pharm.- Weinheim, 301(8), 611 (1968), is reacted with allyl bromide using the conditions described in Example 15A. This product is then hydrogenated using the procedure described in Example 15B to give ethyl 5-methyl-3-propylaminoisothiazole-4-carboxylate.

The above compound is reacted with N-triphenylmethyl-5-[2-(4'-bromomethyl-biphenyl)]tetrazole according to the procedure described in Example 15C to give ethyl 5-methyl-3-{N-Propyl-N-[(2'-[N-triphenylmethyl-1H-tetrazol-5-yl]biphenyl-4-yl)methyl]amino}isothiazole-4-carboxylate.

The above compound is dissolved in 2:3 methylene chloride/formic acid and treated by the procedure described in Example 15D to give the title compound.

EXAMPLE 23

5-Methyl-3-{N-Propyl-N-[(2'-[1H-tetrazol-5-yl]biphenyl-4-yl)methyl]amino}isothiazole-4-carboxylic acid The compound resulting from Example 22 is hydrolyzed with sodium hydroxide in ethanol to give the title compound.

EXAMPLE 24

Methyl 2-{N-propyl-N-[(2'-[1H-tetrazol-5-yl]biphenyl-4-yl)methyl]amino}thiazole-5-carboxylate Methyl 2-aminothiazole-5-carboxylate, prepared by the procedure described in U.S. Pat. No. 4,001,421, is reacted with allyl bromide using the conditions described in Example 15A. This product is then hydrogenated using the procedure described in Example 15B to give methyl 2-propylaminothiazole-5-carboxylate.

The above compound is reacted with N-triphenylmethyl-5-[2-(4'-bromomethyl-biphenyl)]tetrazole according to the procedure described in Example 15C to give methyl 2-{N-Propyl-N-[(2'-[N-triphenylmethyl-1H-tetrazol-5-yl]biphenyl-4-yl)methyl]amino}thiazole-5-carboxylate.

The above compound is dissolved in 2:3 methylene chloride/formic acid and treated by the procedure described in Example 15D to give the title compound.

EXAMPLE 25

2-{N-Propyl-N-[(2'-[1H-tetrazol-5-yl]biphenyl-4-yl)methyl]amino}thiazole-5-carboxylic acid The compound resulting from Example 24 is hydrolyzed with sodium hydroxide in ethanol to give the title compound.

EXAMPLE 26

5-[2-(4'-N-Propylaminomethyl-biphenyl)]tetrazole hydrochloride

Example 26A

N-Benzyloxymethyl-5-(2-bromophenyl)tetrazole 5-(2-Bromophenyl)-[1H]-tetrazole was nitrogen-protected as the benzyloxymethyl (BOM) ether by reaction of a solution of the tetrazole in anhydrous dimethylformamide with technical grade BOM-chloride and anhydrous potassium carbonate. The reaction was complete in less than 60 minutes and the work up involved filtration through Celite and evaporation of the solvent under reduced pressure. The residue obtained was purified by chromatography to afford the title product in 70% yield as an oil which crystallized on standing.

Example 26B

N-(4-Bromobenzyl-N-propylamine

To 4-bromobenzaldehyde (100 g, 0.54 mol) and n-propylamine (36.3 g, 0.60 mol) in methanol (100 mL) was added 5% platinum on carbon (1.00 g). This mixture was shaken in a Parr hydrogenation reactor overnight to complete formation of the Schiff base. The reaction was then hydrogenated under 4 atmospheres of hydrogen until the theoretical uptake of hydrogen had been consumed. The catalyst was removed by filtration through a 0.45 m nylon frit and washed with methanol. The filtrate was concentrated under reduced pressure and the residue obtained dissolved in ether (500 mL). The ether solution was washed with water (2 ×100 mL), 10% sodium bicarbonate solution (2×100 mL), and water (2×100 mL), dried over magnesium sulfate, filtered, and concentrated under reduced pressure to afford the crude title compound (121.34 g). GC-MS showed this material to be 98.5% pure product containing 1.5% of the desbromo compound; the yield is 96.93% based on the GC purity of the product obtained. A sample of this material was purified by bulb-to-bulb distillation (bath temperature 130°-150° C., 0.18 torr). $^1$H NMR (CDCl$_3$, 300 MHz) d 0.92 (t, J=7.4 Hz, 3H), 1.36 (bs, 1H), 1.53 (tq, J$_1$=J$_2$=7.4Hz, 2H), 2.57 (t, J=7.4Hz, 2H), 3.74 (s, 2H), 7.20 (d, J=9Hz, 2H), 7.44 (d, J=9Hz, 2H). IR (film) 1430, 1060 cm$^{-1}$. MS (DCl/NH$_3$) m/e 228, 230 (M+H)$^+$.

Example 26C

4-[(N-tert-Butyloxycarbonyl-N-propylamino)methyl]phenyl boronic acid

To the compound resulting from Example 26B in methylene chloride at 0° C. was added triethylamine (2 equivalents) and di-tert-butyldicarbonate (1.05 equivalents). The cooling bath was removed and the mixture allowed to warm to ambient temperature. The solution was diluted with a suitable solvent (ether or hexane), washed with 2N hydrochloric acid, dried over sodium sulfate and concentrated in vacuo. The Boc-protected compound was obtained as a colorless oil in quantitative yield and was used without further purification.

Grignard formation was effected by treatment of magnesium (1.2 equivalents) in tetrahydrofuran with dibromoethane (0.05 equivlants) followed by heating to reflux and then adding a solution of the protected compound from above in tetrahydrofuran. The reaction mixture turned brown and after 4 hours, most of the metal had been consumed. The Grignard reagent was cooled in a dry ice/acetone bath and then transferred via cannula into a −70° C. solution of trimethyl borate (2.5 equivalents) (~2M in tetrahydrofuran). Upon completion of the addition, the cooling bath was removed and the mixture allowed to warm to ambient temperature. The solution was diluted with ether (4 volumes), washed with 3N hydrochloric acid, ensuring that the aqueous layer was pH 2 or lower. The pH was then adjust to 10 by the addition of 1N sodium hydroxide and the ether layer was discarded. The aqueous solution was cooled to 0° C., carefully acidified to pH 2 with 3N hydrochloric acid and extracted with ether. The combined organic extracts were dried over sodium sulfate and concentrated in vacuo to about 20% of volume whereupon the boronic acid crystallizes in 36% yield.

Example 26D

N-Benzyloxymethyl-5-{2-[4′-(N-propyl-N-tert-butyloxycarbonylamino)methyl-biphenyl]}tetrazole To palladium tetrakis(triphenylphosphine) (0.05 equivalents) dissolved in toluene was added a solution of the compound resulting from Example 26A (1 equivalent). After 10 minutes, a 2M aqueous solution of sodium carbonate was added followed by the compound resulting from Example 26C dissolved in the minimum amount of ethanol. The two-phase mixture was rapidly stirred under reflux for 2.5 hours and then cooled to ambient temperature. The solution was diluted with ether and the organic phase was dried over sodium sulfate and concentrated in vacuo to afford a brown oil. Filtration through silica gel eluting with 35% ether in hexanes afforded the title compound as a colorless oil (87%).

Example 26E

5-[2-4′-N-Propylaminomethyl-biphenyl)]tetrazole hydrochloride

To the compound resulting from Example 26D (1.00 g, 1.94 mmol) dissolved in 1 mL of absolute ethanol at ambient temperature was added a solution of anhydrous hydrogen chloride (g) dissolved in ethanol (5 mL, 11.2M). There was observed an immediate evolution of carbon dioxide which lasted about 90 minutes; also during this time a heavy white precipitate appeared. After 3 hours, the solvent was removed in vacuo and the residue triturated with 8 mL of ethyl acetate. The white solid was then dried in vacuo at 60° C. to afford the title compound (553 mg, 86%).

EXAMPLE 27

2-{N-Butyl-N-[(2′-[1H-tetrazol-5-yl]biphenyl-4-yl)methyl]amino}thiazole-5-carboxylic acid

Example 27A

Ethyl 2-chlorothiazole-5-carboxylate

To a solution of tert-butyl nitrite (9.3 g, 90 mmol) and cupric chloride (9.7 g, 72 mmol) in 150 mL of acetonitrile at 65° C. was added portionwise ethyl 2-aminothiazole-5-carboxylate (10.3 g, 60 mmol) (prepared by the method of Dann, O. Chem Ber 76 419 (1943)) resulting in vigorous gas evolution. After the addition was complete, the solution was stirred until gas evolution ceased (30 minutes). The solution was cooled and poured into 250 mL of cold 20% v/v aqueous HCl. The aqueous solution was extracted 3 times with 200 mL of EtOAc. The organics were combined, washed once with 100 mL of 20% aqueous HCl and 2 times with 100 mL saturated brine and dried over magnesium sulfate. Concentration in vacuo gave 11.1 g (97% yield) of a brown oil which required no purification.

Example 27B

Ethyl 2-{N-butyl-N-[(2′-[N-triphenylmethyl-1H-tetrazol-5-yl]biphenyl-4-yl)methyl]amino}thiazole-5-carboxylate A mixture of the compound resulting from Example 27A (1.34 g, 7.0 mmol), N-triphenylmethyl-5-[2-(4′-butylaminomethyl-biphenyl)]tetrazole (3.8 g, 6.9 mmol), the compound resulting from Example 11A, and N,N-diisopropylethylamine (9.0 g, 70 mmol) in 20 mL of DMF was stirred at 100° C. for 16 hours. The solution was cooled and concentrated under reduced pressure, and the resulting residue was partitioned between 100 mL of EtOAc and 100 mL of H$_2$O. The aqueous phase was extracted 3 times with 100 mL of EtOAc. The combined organic extracts were washed once with 50 mL of saturated brine, dried over MgSO$_4$ and concentrated in vacuo. The crude product was purified by flash chromatography on silica gel eluting with 3:1 hexane/EtOAc to give 3.2 g (66%) of the title compound as a light yellow solid.

Example 27C

Ethyl 2-{N-butyl-N-[(2′-[1H-tetrazol-5-yl]biphenyl-4-yl)methyl]amino}thiazole-5-carboxylate A mixture of the compound resulting from Example 27B (1.5 g, 2.1 mmol) and p-toluenesulfonic acid (2.4 g, 12.6 mmol) in 30 mL of THF was heated at 55° C. for 4 hours. The solution was cooled and adjusted to pH 9 by the addition of 1N NaOH. The basic solution was concentrated under reduced pressure and the residue partitioned between Et$_2$O and H$_2$O. The aqueous phase was washed 2 times with 80 mL of Et$_2$O, cooled to 0° C. and acidified to pH 2 with glacial acetic acid. The acidic aqueous soln was then extracted 3 times with 100 mL of EtOAc. The extracts were combined, washed once with 50 mL of saturated brine, dried (MgSO$_4$) and concentrated in vacuo. The residue was azeotroped several times with toluene to remove residual acetic acid. The sample was dried under high vacuum to give 820 mg (84%) of the title compound. m.p. 65°–70° C.

Example 27D

2-{N-Butyl-N-[(2′-[1H-tetrazol-5-yl]biphenyl-4-yl)methyl]amino}thiazole-5-carboxylic acid A mixture of the compound resulting from Example 27C (200 mg, 0.43 mmol) dissolved in 1N NaOH (4.3 mL, 4.3 mmol), 1 mL EtOH and 1 mL dioxane was stirred at ambient temperature for 72 hours. The solution was concentrated under reduced pressure and the residue partitioned between EtOAc and 1M H$_3$PO$_4$. The aqueous layer was extracted with EtOAC (3×30 mL). The combined organic extracts were washed once with 10 mL of saturated brine, dried over magnesium sulfate and concentrated in vacuo to afford a sticky solid. Trituration of the solid with hexane gave an off-white solid which was collected by filtration and dried to yield 105 mg (56%) of the title compound. m.p. 183°–184° C. $^1$H NMR (DMSO-$d_6$, 300 MHz) δ 0.88 (t, J=7.5Hz, 3H), 1.28 (m, 2H), 1.57 (m, 2H), 3.44 (m, 2H), 4.73 (s, 2H), 7.07 (d, J=8.1Hz, 2H), 7.23 (d, J=8.1Hz, 2H), 7.50–7.73 (m, 4H), 7.76 (s, 1H). MS (FAB) m/e 435 (M)$^+$. Analysis calcd for $C_{22}H_{22}N_6O_2S$: C, 60.81; H, 5.10; N, 19.34. Found: C, 60.56; H, 5.09; N, 18.98.

EXAMPLE 28

2-{N-Propyl-N-[(2'-[1H-tetrazol-5-yl]biphenyl-4-yl)methyl]amino}thiazole-5-carboxylic acid The title compound was prepared according to the procedures described in Example 27. Recrystallization of the crude acid from EtOAc/hexane afforded 243 mg (78% yield) of the title compound as a white solid. m.p. 177°–178° C. $^1$H NMR (DMSO-$d_6$, 300 MHz) δ 0.85 (t, J=7.5Hz, 3H), 1.62 (m, 2H), 3.38 (m, 2H), 4.73 (s, 2H), 7.07 (d, J=8.1Hz, 2H), 7.23(d,J=8.1Hz, 2H),7.52–7.73(m, 4H),7.76(s, 1H). MS (FAB)m/e421 (M)$^+$. Analysis calcd for $C_{21}H_{20}N_6O_2S$: C, 59.99; H 4.79; N 19.99. Found: C, 60.21; H, 4.99; N, 19.84.

EXAMPLE 29

4-Methyl-2-{N-propyl-N-[(2'-[1H-tetrazol-5-yl]biphenyl-4-yl)methyl]amino}thiazole-5-carboxylic acid The title compound was prepared according to the procedures described in Example 27. Recrystallization from EtOAc/hexane gave 110 mg (80% yield) of the title compound as a white solid. m.p. 119°–122° C. $^1$H NMR (DMSO-$d_6$, 300 MHz) δ 0.85 (t, J=7.5Hz, 3H), 1.59 (m, 2H), 2.42 (s, 3H), 3.38 (m, 2H), 4.71 (s, 2H), 7.07 (d, J=8.1Hz, 2H), 7.23 (d, J= 8.1Hz, 2H), 7.52–7.70 (m, 4H). MS (FAB) role 435 (M)$^+$. Analysis calcd for $C_{22}H_{22}N_6O_2S_1.0.125 C_6H_{14}$: C, 61.36; H 5.38; N, 18.87. Found: C, 61.31; H, 5.30; N, 18.75.

EXAMPLE 30

2-{N-Propyl-N-[(2'-[1H-tetrazol-5-yl]biphenyl-4-yl)methyl]amino}thiazole-4-trifluoromethyl-5-carboxylic acid The title compound was prepared according to the procedures described in Example 27. Recrystallization from EtOAc/hexane gave 850 mg (79% yield) of the title compound as a light yellow solid. m.p. 182°–184° C. $^1$H NMR (DMSO-$d_6$, 300 MHz) δ 0.85 (t, J=7.5Hz, 3H), 1.62 (6 line m, 2H), 3.38 (m, 2H), 4.73 (s, 2H), 7.07 (d, J=8.1Hz, 2H), 7.23 (d, J=8.1Hz, 2H), 7.52–7.71 (m, 4H). MS (FAB) role 489 (M)$^+$. Analysis calc for $C_{22}H_{19}N_6O_2SF_3$: C, 54.09; H 3.92; N, 17.20. Found: C, 54.20; H, 4.13; N, 16.78.

EXAMPLE 31

2-{N-Propyl-N-[(2'-[1H-tetrazol-5-yl]biphenyl-4-yl)methyl]amino}thiazole-4-propyl-5-carboxylic acid The title compound was prepared according to the procedures described in Example 27 with no purification to give 600 mg (81% yield) of the desired carboxylic acid as a yellow solid. m.p. 150°–152° C. $^1$H NMR (DMSO-$d_6$, 300 MHz) δ 0.85 (t, J=7.5Hz, 3H), 0.86 (t, J=7.5Hz, 3H), 1.60 (m, 4H), 2.84 (t, J=7.5Hz, 2H), 3.38 (m, 2H), 4.71 (s, 2H), 7.07 (d, J=8.1Hz, 2H), 7.23 (d, J=8.1Hz, 2H), 7.52–7.71 (m, 4H). MS (FAB) m/e 463 (M)$^+$. Analysis calcd for $C_{24}H_{26}N_6O_2S$: C, 62.32; H 5.67; N, 18.17. Found: C, 62.22; H, 5.72; N, 17.75.

EXAMPLE 32

2-{N-[(2'-[1H-Tetrazol-5-yl]biphenyl-4-yl)methyl]amino}thiazole-5-carboxylic acid The title compound was prepared according to the procedures described in Example 27. Treatment of the saponification mixture with 1M phosphoric acid gave a precipitate which was collected by filtration and dried to afford 329 mg (87% yield) of the desired acid. m.p. 200°–201° C. $^1$H NMR (DMSO-$d_6$, 300 MHz) δ 4.49 (d, J=4.8Hz, 2H), 7.07 (d, J=8.1Hz, 2H), 7.27 (d, J=8.1Hz, 2H), 7.52–7.71 (m, 5H), 8.87 (bt, J=4.5Hz, 1H). MS (FAB) m/e 379 (M)$^+$. Analysis calcd for $C_{18}H_{14}N_6O_2S.0.25 H_2O$: C, 56.46; H 3.82; N, 21.95. Found: C, 56.62; H, 3.79; N, 21.56.

EXAMPLE 33

2-{N-Hexyl-N-[(2'-[1H-tetrazol-5-yl]biphenyl-4-yl)methyl]amino}thiazole-5-carboxylic acid Following the procedures described in Example 27, the title compound was prepared as an off-white solid in 90% yield (830 mg). m.p. 113°–117° C. $^1$H NMR (DMSO-$d_6$, 300 MHz) δ 0.84 (t, J=7.5Hz, 3H),1.19–1.20 (m, 6H), 1.58 (m, 2H), 3.42 (m, 2H), 4.73 (s, 2H), 7.07 (d, J=8.1Hz, 2H), 7.23 (d, J=8.1Hz, 2H), 7.52–7.71 (m, 4H), 7.76 (s, 1H). MS (FAB) m/e 463 (M)$^+$. Analysis calcd. for $C_{24}H_{26}N_6O_2S.0.5$ HOAc: C, 60.96; H 5.73; N, 17.05. Found: C, 61.29; H, 5.61; N, 17.27.

EXAMPLE 34

4-Propyl-2-{N-[(2'-[1H-tetrazol-5-yl]biphenyl-4-yl)methyl]amino}thiazole-5-carboxylic acid The title compound was prepared according to the procedures described in Example 27. Treatment of the saponification mixture with 1M phosphoric acid gave a precipitate which was collected by filtration and dried to afford 450 mg (63% yield) of the desired acid. m.p. 147°–149° C. $^1$H NMR (DMSO-$d_6$, 300 MHz) δ 0.84 (t, J=7.5Hz, 3H), 1.58 (6 line m, 2H), 2.82 (t, J=7.5Hz, 2H), 4.45 (d, J=4.8Hz, 2H), 7.07 (d, J=8.1Hz, 2H), 7.25 (d, J=8.1Hz, 2H), 7.49–7.69 (m, 4H), 8.69 (bt, J=4.5Hz, 1H). MS (FAB) m/e 421 (M+H)$^+$. Analysis calcd for $C_{21}H_{20}N_6O_2S.0.375 H_3PO_4$: C, 55.20; H, 4.66; N, 18.40. Found: C, 55.55; H, 4.48; N, 18.53.

EXAMPLE 35

1-Methyl-4-{N-[(2'-[1H-tetrazol-5-yl]biphenyl-4-yl)methyl]amino}-1H-1,2,3-triazole-5-carboxylic acid

Example 35A

Ethyl 5-amino-1-benzyl-1H-1,2,3-triazole-4-carboxylate

To 24 mL (0.2 mol) of benzyl bromide dissolved in 42 mL of absolute ethanol was added 14.3 g (0.22 mol) of sodium azide. The mixture was refluxed slowly for 3 hours, cooled to ambient temperature and filtered. The filtrate was concentrated in vacuo and the resulting residue was diluted with 800 mL of heptane. Insoluble material was removed by filtration and the filtrate concentrated under reduced pressure to give 16.0 g (60%) of benzyl azide which was used without further purification.

To a solution of 1.15 g (0.05 mol) of sodium in 80 mL of absolute ethanol was added 4.5 mL of methyl cyanoacetate and 6.5 g (0.05 mol) of benzyl azide. A white precipitate formed immediately, and the resulting mixture was stirred overnight. The yellowish creamy mixture was poured into 500 mL of ice water, and a crude yellow precipitate was collected by filtration. Recrystallization from ethanol afforded the title compound as a pale yellow solid (5.0 g, 42%). m.p. 153° C.

Example 35B

Ethyl 5-amino-1-benzyl-3-methyl-[1,2,3]-triazolium-4-carboxylate tosylate

The compound resulting from Example 35A (1.2 g, 4.9 mmol), methyl p-toluenesulfonate (1.37 g, 7.35 mmol) and methyl sulfoxide (1.0 mL) were heated for 15 minutes at 150° C. (oil bath temperature). The mixture was cooled to 50° C., 15 mL of ethanol was added and the mixture was concentrated under reduced pressure. The residue obtained was purified by column chromatography on silica gel eluting with 1:1 ethyl acetate-hexane and 7% methanol in methylene chloride to give 1.9 g (90%) of the title compound.

Example 35C

Ethyl 4-amino-1-methyl-1H-1,2,3-triazole-5-carboxylate

The compound resulting from Example 35B (1.50 g, 3.47 mmol), manganese(II)oxide (150 mg), and 5% palladium on carbon (420 mg) were suspended in 50 mL of absolute ethanol at 1 atmosphere of hydrogen overnight. The catalyst was removed by filtration and the filtrate concentrated under reduced pressure. The residue obtained was suspended in 5.0 mL of saturated sodium bicarbonate solution and 5.0 mL of water. The resulting solution was extracted with ethyl acetate (2×150 mL). The combined organic extracts were back washed with water and brine, dried and concentrated in vacuo to afford 400 mg (68%) of the title compound as a white solid.

Example 35C

Ethyl 4-N-butylamino-1-methyl-1H-1,2,3-triazole-5-carboxylate]

To the compound resulting from Example 35B (340 mg, 2.0 mmol) dissolved in 2 mL of anhydrous THF in a dry ice bath was added 2.0 mL of anhydrous 1,3-dimethyl-3,4,5,6-tetrahydro-2(1H)-pyrimidone (DMPU) followed by 2.3 mL of a 1M solution of lithium bis(trimethylsilyl)amide in THF. The mixture was stirred for 30 minutes and then 0.28 mL of 1-iodobutane was added. The ice bath was removed and the solution stirred for 1 hour. The solvent was removed under reduced pressure and the resulting residue was purified by column chromatography on silica gel eluting with 15–20% ethyl acetate in hexane to afford 294 mg (65%) of the title compound.

Example 35D

Ethyl 4-{N-butyl-N-[(2'-[N-triphenylmethyl-1H-tetrazol-5-yl]biphenyl-4-yl)methyl]amino}-1-methyl-1H-1,2,3-triazole-5-carboxylate To the compound resulting from Example 35C (136 mg, 0.6 mmol) dissolved in 2.5 mL of THF and cooled in an ice bath was added 1.0 mL of 1,3-dimethyl-3,4,5,6-tetrahydro-2(1H)-pyrimidinone (DMPU) followed by 1.2 mL (2 equivalents) of 1M lithium bis(trimethylsilyl)amide in THF. The resulting mixture was stirred for 20 minutes and then N-triphenylmethyl-5-[2-(4'-bromomethyl-biphenyl)]tetrazole (350 mg, 0.63 mmol) was added. The resulting mixture was stirred for 2 hours at ambient temperature and then concentrated under reduced pressure. The residue obtained was purified by column chromatography on silica gel eluting with 30–40% ethyl acetate in hexane to afford 295 mg (70%) of the title compound.

Example 35E

4-{N-Butyl-N-[(2'-[1H-tetrazol-5-yl]biphenyl-4-yl)methyl]amino}-1-methyl-1H-1,2,3-triazole-5-carboxylic acid The compound resulting from Example 35D (280 mg, 0.4 mmol) was dissolved in 8.0 mL of methylene chloride and 12.0 mL of formic acid (88%) and stirred for 2 hours at ambient temperature. The solvents were removed under reduced pressure and the residue was chased twice with toluene (2×5 mL). The residue obtained was treated with 6 mL of 50% formic add in water to precipitate triphenylcarbinol which was removed by filtration. The filtrate was concentrated in vacuo and dissolved in methylene chloride (100 mL). This solution was washed with water and brine, dried over sodium sulfate and concentrated in vacuo to give the detritylated ethyl ester as a white solid (165 mg, 90%).

To the above ethyl ester (100 mg, 0.22 mmol) dissolved in 4.0 mL of ethanol was added a solution of 150 mg of sodium hydroxide dissolved in 2.0 mL of water. The resulting mixture was refluxed for 1 hour, cooled to ambient temperature and concentrated under reduced pressure. The residue obtained was dissolved in 3 mL of water, acidified by the addition of formic acid, and extracted with ethyl acetate (2×100 mL). The combined organic extracts were dried over sodium sulfate, concentrated in vacuo and crystallized from ether. The title compound was recrystallized from ethyl acetate, ether and hexanes to afford 76 mg (80%). m.p. 168°–169° C. $^1$H NMR (CDCl$_3$, 300 MHz) δ 0.90 (t, J=7.5Hz, 3H), 1.35 (m, 2H), 1.52 (m, 2H), 3.42 (t, J=7.5Hz, 2H), 4.28 (s, 3H), 4.36 (s, 2H), 7.08 (s, 3H), 7.26 (s, 2H), 7.41 (dd, J=2Hz, 9Hz, 1H), 7.55 (m, 2H), 8.06 (dd, J=2Hz, 9Hz, 1H), MS (FAB) m/e 433 (M+H)$^+$.

EXAMPLE 36

4-{(2'-[1H-tetrazol-5-yl]biphenyl-4-yl)methyl]amino}-1-isobutyl-1H-1,2,3-triazole-5-carboxylic acid

Example 36A

Ethyl 4-amino-1-isobutyl-1H-1,2,3-triazole-5-carboxylate

The compound resulting from Example 35A was reacted with isobutyl p-toluenesulfonate by the procedure described in Example 35B to give 1.3 g (68%) of the title compound.

Example 36B

4-{N-Butyl-N-[(2'-[1H-tetrazol-5-yl]biphenyl-4-yl)methyl]amino}-1-isobutyl-1H-1,2,3-triazole-5-carboxylic acid The compound resulting from Example 36A was reacted by the procedures described in Example 35C, D, and E to give the title compound (56 mg, 70%). m.p. 105°–106° C. $^1$H NMR (CDCl$_3$, 300 MHz) δ 0.82 (d, J=7.5Hz, 6H), 0.92 (t, J=6.8Hz, 3H), 1.36 (m, 2H), 1.48 (m, 2H), 2.18 (m, 1H), 3.38 (t, J=6.8Hz, 2H), 4.28 (s, 2H), 4.47 (d, J=7.5 Hz, 2H), 7.30 (dd, J=7.5Hz, 18Hz, 4H), 7.38 (m, 1H), 7.55 (m, 2H), 8.12 (m, 1H). MS (FAB) m/e 475 (M+H)$^+$.

EXAMPLE 37

1-n-Butyl-4-{N-butyl-N-[(2'-[1H-tetrazol-5-yl]biphenyl-4-yl)methyl]amino}-1H-1,2,3-triazole-5-carboxylic acid

Example 37A

Ethyl 4-amino-1-n-butyl-1 H-1,2,3-triazole-5-carboxylate

The compound resulting from Example 35A was reacted with n-butyl p-toluenesulfonate by the procedure described in Example 35B to give 1.3 g (68%) of the title compound.

Example 37B 1-n-Butyl-4-{N-[(2'-[1H-tetrazol-5-yl]biphenyl-4-yl)methyl]amino}-1H-1,2,3-triazole-5-carboxylic acid The compound resulting from Example 37A was reacted by the procedures described in Example 35C, D, and E to give the title compound (14.5 mg). m.p. 154°–155° C. $^1$H NMR (CDCl$_3$, 300 MHz) δ 0.88 (m, 6H), 1.20–1.38 (m, 5H), 1.50 (m, 2H), 1.78 (m, 2H), 3.42 (m, 2H), 4.34 (bs, 2H), 4.65 (t, J=7Hz, 2H), 7.02 (bs, 4H), 7.38 (d, J=7Hz, 1H), 7.55 (m, 2H), 8.08 (d J=7Hz, 1H). MS (FAB) m/e 475 (M+H)$^+$.

EXAMPLE 38

4-{N-Propyl-N-[(2'-[1H-tetrazol-5-yl]biphenyl-4-yl)methyl]amino}-1,2,5-thiadiazole-4-carboxylic acid

Example 38A

Methyl 3-amino-1,2,5-thiadiazole-4-carboxylate

A stirred suspension of 4.0 g (17 mmol) of 4,5-diaminopyridine-4(3H)-one sulfate in 20 mL of 1,1,1,3,3,3,-hexamethyldisilazane was refluxed for 15 hours under a nitrogen atmosphere. After the addition of 75 mL of toluene, the filtered solution was evaporated to dryness under reduced pressure to give 4.5 g of crude silylated pyrimidine. To this crude material was slowly added 15 mL of thionyl chloride under nitrogen and the mixture was refluxed for 20 minutes. After removal of the excess thionyl chloride under reduced pressure, 100 mL of methanol was added, and the mixture was refluxed for 2 hours. The solvents were removed under reduced pressure and the solid obtained was recrystallized from methanol to afford 2.19 g (78%) of the title compound. m.p. 142°–143° C.

Example 38B

Methyl 3-bromo-1,2,5-thiadiazole-4-carboxylate

To a solution of 1.07 g (4.8 mmol) of copper(II)bromide and 618 mg (6 mmol) of tert-butyl nitrite in acetonitrile (20 mL) at 60° C. was added portionwise the compound resulting from Example 38A (636 mg, 4 mmol). After the addition, the solution was heated at 65° C. for 30 additional minutes. The reaction mixture was cooled and poured into 75 mL of cold aqueous 20% hydrobromic acid. The aqueous solution was extracted with 400 mL of ethyl acetate. The organic layer was washed with water and brine, dried and concentrated under reduced pressure. The residue obtained was purified by column chromatography on silica gel eluting with 10% ethyl acetate in hexane to give 520 mg (59%) of the title compound. m.p. 57°–58° C.

Example 38C

Methyl 4-{N-propyl-N-[(2'-[N-triphenylmethyl-1H-tetrazol-5-yl]biphenyl-4-yl)methyl]amino}-1,2,5-thiadiazole-4-carboxylate N-Triphenylmethyl-5-[2-(4'-propylaminomethyl-biphenyl)]tetrazole (107 mg, 0.2 mmol), the compound resulting from Example 21A, and 133 mg (3 equivalents) of the compound resulting from Example 38B were dissolved in 5 ML of anhydrous acetonitrile and 0.5 mL of diisopropylethylamine. The reaction tube was sealed and the mixture was stirred in an oil bath at 100°–110° C. for 1.5 hours. The solvents were removed under reduced pressure and the residue obtained was purified by column chromatography on silica gel eluting with 10–15% ethyl acetate in hexane to afford the title compound (95 mg, 70%).

Example 38D

4{N-Propyl-N-[(2'-[1H-tetrazol-5-yl]biphenyl-4-yl)methyl]amino}-1,2,5-thiadiazole-4-carboxylic acid The compound resulting from Example 38C was treated with formic acid by the procedure described in Example 35E to give 52 mg (90%) of the deprotected tetrazole compound. Ester hydrolysis of this compound was carried out by the procedure described in Example 35E using methanol as the solvent and running the reaction at ambient temperature to afford 36 mg (75%) of the title compound. m.p. 97°–98 ° C. $^1$H NMR (CDCl$_3$, 300 MHz) δ 0.94 (t, J=7.5Hz, 3H), 1.72 (m, 2H), 3.50 (t, J=7.5Hz, 2H), 4.70 (s, 2H), 7.14 (d, J=8Hz, 2H), 7.25 (d, J=8Hz, 3H), 7.44 (dd, J=1.5Hz, 7.5Hz, 1H), 7.58 (m, 2H), 8.12 (dd, J=1.5Hz, 7.5Hz, 1H). MS (FAB) m/e 422 (M+H)$^+$.

The compounds of the present invention can be used in the form of salts derived from inorganic or organic acids. Pharmaceutically acceptable salts are described in Berge, et al., J. Pharmaceutical Sciences 66 1–19 (1977). These salts include but are not limited to the following: acetate, adipate, alginate, citrate, ascorbate, aspartate, benzoate, benzenesulfonate, bisulfate, borate, butyrate, camphorate, camphorsulfonate, citrate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxyethanesulfonate, lactobionate, lactate, laurate, lauryl sulfate, maleate, methanesulfonate, nicotinate, 2-naphthalenesulfonate, oleate, oxalate, palmitate, pamoate, pectinate, persulfate, phosphate, 3-phenyl-propionate, picrate, pivalate, propionate, stearate, succinate, tartrate, thiocyanate, toluenesulfonate (tosylate), undecanoate and valerate.

Examples of acids which can be employed to form pharmaceutically acceptable acid addition salts include such inorganic acids as hydrochloric acid, sulphuric acid and phosphoric acid and such organic acids as oxalic acid, maleic acid, succinic acid, methanesulfonic acid and citric acid. Other salts include salts with alkali metals or alkaline earth metals, such as sodium, potassium, calcium or magnesium or with organic bases. The salts can be prepared in situ during the final isolation and purification of the compounds of formula (I), or separately by reacting the free base function with a suitable acid or by reacting the acidic function with a suitable base.

The compounds of the present invention are useful for blocking the interaction of angiotensin II with angiotensin II receptors and for treating hypertension, edema, renal failure, congestive heart failure, glaucoma, psoriasis, benign prostatic hypertrophy, diabetic nephropathy, diabetic retinopathy, or to prevent atherosclerosis or for treating gastrointestinal disorders associated with enhanced contractility and/or motility of intestinal smooth muscle or for treating contractile disorders of the uterus (including premature contractions, dysmenorrhea and the like) or for treating or preventing stroke, cerebral vasospasm or cerebral infarction or for treating CNS disorders (depression, schizophrenia, anxiety or cognitive disorders (Alzheimer's disease, amnesia and senile dementia))in a human or other mammal. The compounds of the invention are also useful for enhancing intimal wound closure and for reducing luminal thrombogenicity in a human or other mammal.

ANGIOTENSIN II FUNCTIONAL ASSAY:
Antagonism of Contraction of Rabbit Aorta

The protocol reported by A. T Chiu and P. Timmermans (P. C. Wong, et al. *Hypertension*, 13, 489–497 (1989)) was followed with a few modifications. Female New Zealand White rabbits weighing 2–5 kg were sedated with carbon dioxide and then sacrificed. Main abdominal aortas were removed and placed in Krebs-Henseleit buffer at room temperature.

| Krebs-Henseleit buffer | |
|---|---|
| Buffer Component | mM Concentration |
| sodium chloride | 119.00 |
| potassium chloride | 4.70 |
| potassium dihydrogen phosphate | 1.20 |
| calcium chloride | 2.50 |
| sodium bicarbonate | 20.00 |
| magnesium sulfate | 1.50 |
| dextrose | 11.00 |
| EDTA* disodium calcium salt | 0.01 |

*EDTA = ethylenediamine tetraacetic acid
The buffer contained no cocaine, propanolol or steroid.
The pH of the buffer was 7.40 at 37° C. when saturated with 5% carbon dioxide/95% oxygen.

The tissues were cleaned of extraneous connective tissue, cut into 3 mm rings, and suspended within a 10 mL tissue bath. All dilutions of peptide preparations were made with 0.3% aqueous BSA. The tissues were primed with 55 mM potassium chloride. Tissues were pre-loaded with 1 g of tension. Tension was recorded on a model 7 Grass polygraph using FT03 transducers. At the end of the equilibrium period, a control cumulative concentration-contractile response curve for angiotensin II (A II: $1 \times 10^{-10} - 10^{-8}$ M) was obtained. The tissue was washed several times until the baseline was reached. Forty five minutes later, test compound (antagonist) was added and the tissue was incubated for 30 minutes. The concentration-response curve for A II was then repeated in the presence of the test compound. One dose of antagonist was tested per tissue only. For single dose shift experiments a dose of 1 mM of test compound was used, for a full $pA_2$ experiment multiple doses were used depending upon the potency of the antagonist.

All responses to the control agonist were calculated as a percentage of the maximum response. These points in duplicate were plotted and analyzed according to standard Schild analysis (H. O. Schild, *British J Pharmacology and Chemotherapy*, 2, 189–206 (1947). The $pA_2$ values calculated for the compounds of the invention are shown in Table 6. The $pA_2$ value is the negative logarithm of the $[A]_2$ value. $[A]_2$ is the concentration of antagonist which necessitates doubling the agonist concentration in order to achieve the agonist effect which was measured in the absence of antagonist.

The $pA_2$ value, therefore, is a measure of the effectiveness of the compound as an antagonist. The data in Table 5 show that the compounds of the invention are potent antagonists at the angiotensin II receptor.

TABLE 5

| $pA_2$ Values from Isolated Rabbit Aorta Assay | |
|---|---|
| Example | $pA_2$ |
| 1 | 6.98 |
| 3 | 8.20 |
| 5 | 7.06 |
| 6 | 8.12 |
| 9 | 7.78 |
| 10 | 8.36 |
| 11 | 8.53 |
| 12 | 7.70 |
| 14 | 7.94 |
| 27 | 8.78 |
| 28 | 7.87 |
| 29 | 8.63 |
| 30 | 7.56 |
| 31 | 7.43 |

Sar, −1, Thr-8 AII (SARILE) 9.02

The ability of the compounds of the invention to lower blood pressure in vivo in renal artery ligated rats can be demonstrated according to the method disclosed by Cangiano, et al., J. Pharmacol. Exp. Ther. 208 310 (1979)).

The total daily dose of the compounds of this invention administered to a human or other mammal in single or in divided doses can be in amounts, for example, from 0.01 to 25 mg/kg body weight or more usually from 0.1 to 15 mg/kg body weight. Single dose compositions can contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose of from 10 mg to 1000 mg.

It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches. The term parenteral as used herein includes subcutaneous injections, intravenous, intramuscular, intrasternal injection, or infusion techniques.

Liquid dosage forms for oral administration can include pharmaceutically acceptable emulsions, microemulsions, solutions, suspensions, syrups and elixirs containing inert diluents commonly used in the art such as water. Such compositions can also comprise adjuvants, such as wetting agents; emulsifying and suspending agents; sweetening, flavoring and perfuming agents.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration can include capsules, tablets, pills, powders, prills and granules. In such solid dosage forms the active compound can be admixed with at least one inert diluent such as sucrose, lactose or starch. Such dosage forms can also comprise, as is normal practice, additional substances other than inert diluents, e.g., tableting lubricants and other tableting aids such as magnesium stearate and microcrystalline cellulose. In the case of capsules, tablets and pills, the dosage forms can also comprise buffering agents. Tablets and pills can additionally be prepared with enteric coatings and other release-controlling coatings.

Solid compositions of a similar type can also be employed as fillers in soft and hard-filled gelatin capsules using such exipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulations, ear drops, eye ointments, powders and solutions are also contemplated as being within the scope of this invention.

The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonires, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

The compounds of the present invention can be administered alone or in combination or in concurrent therapy with other cardiovascular agents independently selected from diuretics, adrenergic blocking agents, vasodilators, calcium channel blockers, angiotensin converting enzyme (ACE) inhibitors, potassium channel activators, antiserotoninergic agents, thromboxane synthetase inhibitors, renin inhibitors and other agents useful for treating (in a human or other mammal) hypertension, edema or congestive heart failure.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside, flosequinan and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Representative antiserotoninergic agents include ketanserin and the like or a pharmaceutically acceptable salt thereof.

Representative renin inhibitiors include enalkiren, A-72517, PD-134672 or Ro 42-5892 and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compound of formula I and the other cardiovascular agent can be administered at the recommended maximum clinical dosage or at lower doses. Dosage levels of the active compounds in the compositions of the invention can be varied so as to obtain a desired therapeutic response depending on the route of administration, severity of the disease and the response of the patient. The combination can be administered as separate compositions or as a single dosage form containing both agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

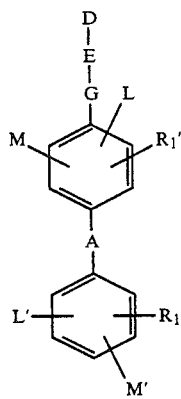

I wherein
  A is
    (i) a covalent bond,
    (ii) —O—,
    (iii) —C(O)—,
    (iv) —CH$_2$—,
    (v) —S—, —S(O)— or —S(O)$_2$—;
  E—G is
    (i) —N(R$_5$)—,
    (ii) —O—,
    (iii) —S—,
    (iv) —N(R$_5$)—CH(R$_5$)—,
    (v) —O—CH(R$_5$)—,
    (vi) —S—CH(R$_5$)—,
    (vii) —CH(R$_5$)—N(R$_5$)—,
    (viii) —CH(R$_5$)—O—,
    (ix) —CH(R$_5$)—S—,
    (x) —N(R$_5$)—N(R$_5$)—,
    (xi) —C(R$_5$)=C(R$_5$)— or (xii) —CH(R$_5$)—C(R$_5$')(R$_5$)—N(R$_5$)— wherein at each occurrence R$_5$ is independently selected from hydrogen, loweralkyl, alkoxy-substituted loweralkyl, halo-substituted loweralkyl, carboxy-substituted loweralkyl, heterocyclic-substituted loweralkyl, alkenyl, alkynyl, cycloalkyl or cycloalkylalkyl and R$_5$' is hydrogen, halo, hydroxy, carboxy, alkoxy or thioalkoxy;
  L, L', M and M' are independently selected from
    (i) hydrogen,
    (ii) loweralkyl,
    (iii) halo-substituted loweralkyl,
    (iv) halo,
    (v) —CN,
    (vi) —NO$_2$,
    (vii) —OH,
    (vii) hydroxy-substituted loweralkyl,
    (ix) alkoxy-substituted loweralkyl,
    (x) —NH$_2$,
    (xi) alkylamino,
    (xii) dialkylamino,
    (xiii) —SH,
    (xiv) alkoxy and
    (xv) thioalkoxy;
  R$_1$ and R$_1$' are independently selected from
    (i) tetrazolyl,

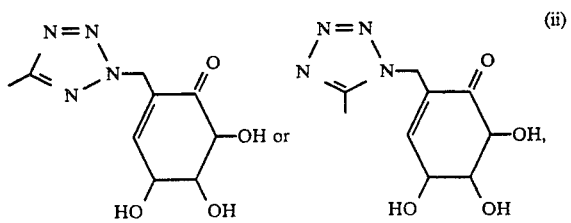

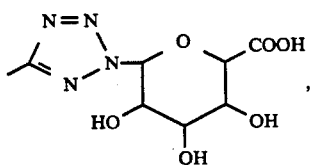

and (iv) hydrogen:
with the proviso that one of $R_1$ and $R_1'$ is hydrogen, but $R_1$ and $R_1'$ are not both hydrogen; and D is a 5-membered heterocyclic ring comprising 1, 2, 3 or 4 nitrogen atoms or 2 nitrogen atoms and 1 oxygen atom or 2 nitrogen atoms and 1 sulfur atom, the remaining ring atoms being carbon atoms and the 5-membered heterocyclic ring comprising 0, 1 or 2 double bonds; the nitrogen atoms of the 5-membered heterocyclic ring can be substituted with a substituent $R_2$ wherein at each occurrence $R_2$ is independently selected from hydrogen, loweralkyl, carboxy-substituted loweralkyl or alkoxycarbonyl-substituted loweralkyl; one or two carbon atoms of the 5-membered heterocyclic ring can also be substituted with an oxo (=O) substituent and the sulfur atoms of the 5-membered heterocyclic ring can be substituted with one or two oxo (=O) substituents; the nitrogen atoms of the 5-membered heterocyclic ring can be oxidized; the 5-membered heterocyclic ring can also be substituted with one or two substituents independently selected from $R_3$ and $R_4$, $R_3$ being bonded to a carbon atom or a nitrogen atom of the 5-membered heterocyclic ring and $R_4$ being bonded to a carbon atom or a nitrogen atom of the 5-membered heterocyclic ring, wherein $R_3$ is
(i) hydrogen
(ii) loweralkyl,
(iii) halo,
(iv) halo-substituted loweralkyl,
(v) thioalkoxy,
(vi) alkoxy-substituted loweralkyl,
(vii) thioalkoxy-substituted loweralkyl,
(viii) aryl,
(ix) arylalkyl,
(x) —$NO_2$, or
(xi) —$COOR_8$ wherein $R_8$ is hydrogen or a carboxy-protecting group, and $R_4$ is
(i) hydrogen,
(ii) loweralkyl,
(iii) halo-substituted loweralkyl,
(iv) —CN,
(v) —$NO_2$,
(vi) —$NH_2$,
(vii) —NH—C(=N($R_{25a}$))($R_{26a}$) wherein $R_{25a}$ is hydrogen, —CN or —$NO_2$ and $R_{26a}$ is hydrogen, loweralkyl, alkylamino, dialkylamino, alkoxy or thioalkoxy,
(viii) —CHO or —CH(=N—OH),
(ix) —NHS(O)$_2R_{20}$ or —CH$_2$NHS(I)$_2R_{20}$ or —NHC(O)$R_{21}$ or —N(OH)C(O)$R_{21}$ or —CH$_2$NHC(O)$R_{21}$ or —CH$_2$N(OH)C(O)$R_{21}$ wherein $R_{20}$ is loweralkyl, halo-substituted loweralkyl or —$NR_{27a}R_{27b}$ wherein $R_{27a}$ and $R_{27b}$ are independently selected from hydrogen, —OH and loweralkyl and $R_{21}$ is loweralkyl, halo-substituted loweralkyl, amino, alkylamino, dialkylamino or —COOH, (x) —CH(OH)$R_{22}$ or —C(O)$R_{22}$ wherein $R_{22}$ is loweralkyl, halo-substituted loweralkyl, —CF$_2$COOR$_{23}$ or —CH$_2$COOR$_{23}$ wherein $R_{23}$ is hydrogen or a carboxy-protecting group, (xi) —COOR$_{24}$ or —CH$_2$COOR$_{24}$ wherein $R_{24}$ is hydrogen or a carboxy-protecting group, (xii) —C(O)NR$_{25}$R$_{26}$ or —CH$_2$C(O)NR$_{25}$R$_{26}$ or —NHC(O)NR$_{25}$R$_{26}$ or —CH$_2$NHC(O)NR$_{25}$R$_{26}$ or —NHC(S)NR$_{25}$R$_{26}$ or —CH$_2$NHC(S)NR$_{25}$R$_{26}$ wherein $R_{25}$ and $R_{26}$ are independently selected from hydrogen, loweralkyl, hydroxy, alkoxy, hydroxy-substituted loweralkyl, alkoxy-substituted loweralkyl, alkoxy-substituted alkoxy and —S(O)$_2$R$_{28a}$ wherein $R_{28a}$ is loweralkyl or aryl;

(xiii) —CH$_2$OR$_{27}$ wherein $R_{27}$ is selected from hydrogen, loweralkyl and —C(O)R$_{28}$ wherein $R_{28}$ is hydrogen, loweralkyl or aryl;

(xiv) —CH$_2$NR$_{29}$R$_{30}$ wherein $R_{29}$ is selected from hydrogen, loweralkyl, —C(O)R$_{31}$, —C(O)NR$_{31}$R$_{32}$ and —S(O)$_2$R$_{33}$ wherein $R_{31}$ is selected from hydrogen, loweralkyl and aryl and $R_{33}$ is selected from loweralkyl and halo-substituted loweralkyl and wherein $R_{30}$ and $R_{32}$ are independently selected from hydrogen, loweralkyl, hydroxy and alkoxy;

(xv) —SO$_3$H, —OSO$_3$H or —CH$_2$SO$_3$H,
(xvi) —OPO$_3$H, —PO$_3$H$_2$ or —CH$_2$PO$_3$H$_2$,
(xvii) —SO$_2$NR$_{25}$R$_{26}$ or —CH$_2$SO$_2$NR$_{25}$R$_{26}$ wherein $R_{25}$ and $R_{26}$ are defined as above or (xviii) —C(O)NHSO$_2$R$_{59}$, —C(O)NHC(O)R$_{59}$ or —C(O)NHNHSO$_2$R$_{59}$ wherein $R_{59}$ is loweralkyl, halo-substituted loweralkyl or aryl;

or a pharmaceutically acceptable salt or prodrug thereof.

2. The compound of claim 1 wherein A is a covalent bond, L, L', M, M' and $R_1'$ are hydrogen, $R_1$ is tetrazolyl, —G—E— is —CH$_2$—N(R$_5$)— and D is a substituted 1,2,3-triazolyl group, a 1,2,5-thiadiazolyl group, a substituted imidazolyl group, a substituted pyrazolyl group, a substituted oxadiazolyl group or a substituted pyrrolidinyl group.

3. A compound of the formula:

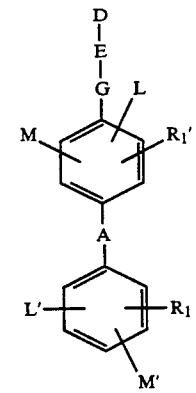

wherein
A is
(i) a covalent bond,
(ii) —O—,
(iii) —C(O)—, (iv) —CH₂—,
(v) —S—, —S(O)— or —S(O)₂—;

E—G is
(i) —N(R₅)—,
(ii) —O—,
(iii) —S—,
(iv) —N(R₅)—CH(R₅)—,
(v) —O—CH(R₅)—,
(vi) —S—CH(R₅)—,
(vii) —CH(R₅)—N(R₅)—,
(viii) —CH(R₅)—O—,
(ix) —CH(R₅)—S—,
(x) —N(R₅)—N(R₅)—,
(xi) —C(R₅)=C(R₅)— or
(xii) —CH(R₅)—C(R₅')(R₅)—N(R₅)— wherein at each occurrence R₅ is independently selected from hydrogen, loweralkyl, alkoxy-substituted loweralkyl, halo-substituted loweralkyl, carboxy-substituted loweralkyl, heterocyclic-substituted loweralkyl, alkenyl, alkynyl, cycloalkyl or cycloalkylalkyl and R₅' is hydrogen, halo, hydroxy, carboxy, alkoxy or thioalkoxy;

L, L', M and M' are independently selected from
(i) hydrogen,
(ii) loweralkyl,
(iii) halo-substituted loweralkyl,
(iv) halo,
(v) —CN,
(vi) —NO₂,
(vii) —OH,
(viii) hydroxy-substituted loweralkyl,
(ix) alkoxy-substituted loweralkyl,
(x) —NH₂,
(xi) alkylamino,
(xii) dialkylamino,
(xiii) —SH,
(xiv) alkoxy and
(xv) thioalkoxy;

R₁ and R₁' are independently selected from
(i) tetrazolyl,

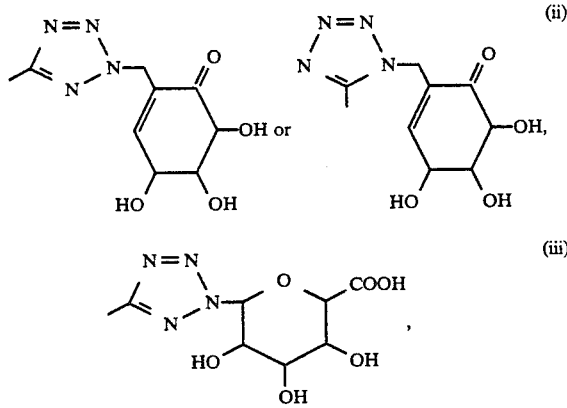

and
(iv) hydrogen:
with the proviso that one of R₁ and R₁' is hydrogen, but R₁ and R₁' are not both hydrogen; and
D is

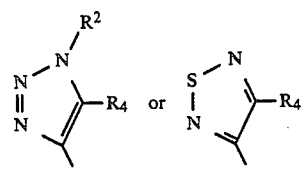

wherein R₂ is hydrogen, loweralkyl, carboxy-substituted loweralkyl or alkoxycarbonyl-substituted loweralkyl, and R₄ is
(i) hydrogen,
(ii) loweralkyl,
(iii) halo-substituted loweralkyl,
(iv) —CN,
(v) —NO₂,
(vi) —NH₂,
(vii) —NH—C(=N(R₂₅ₐ))(R₂₆ₐ) wherein R₂₅ₐ is hydrogen, —CN or —NO₂ and R₂₆ₐ is hydrogen, loweralkyl, alkylamino, dialkylamino, alkoxy or thioalkoxy,
(viii) —CHO or —CH(=N—OH),
(ix) —NHS(O)₂R₂₀ or —CH₂NHS(O)₂R₂₀ or —NHC(O)R₂₁ or —N(OH)C(O)R₂₁ or —CH₂NHC(O)R₂₁ or —CH₂N(OH)C(O)R₂₁ wherein R₂₀ is loweralkyl, halo-substituted loweralkyl or —NR₂₇ₐR₂₇ᵦ wherein R₂₇ₐ and R₂₇ᵦ are independently selected from hydrogen, —OH and loweralkyl and R₂₁ is loweralkyl, halo-substituted loweralkyl, amino, alkylamino, dialkylamino or —COOH,
(x) —CH(OH)R₂₂ or —C(O)R₂₂ wherein R₂₂ is loweralkyl, halo-substituted loweralkyl, —CF₂COOR₂₃ or —CH₂COOR₂₃ wherein R₂₃ is hydrogen or a carboxy-protecting group,
(xi) —COOR₂₄ or —CH₂COOR₂₄ wherein R₂₄ is hydrogen or a carboxy-protecting group,
(xii) —C(O)NR₂₅R₂₆ or —CH₂C(O)NR₂₅R₂₆ or —NHC(O)NR₂₅R₂₆ or —CH₂NHC(O)NR₂₅R₂₆ or —NHC(S)NR₂₅R₂₆ or —CH₂NHC(S)NR₂₅R₂₆ wherein R₂₅ and R₂₆ are independently selected from hydrogen, loweralkyl, hydroxy, alkoxy, hydroxy-substituted loweralkyl, alkoxy-substituted loweralkyl, alkoxy-substituted alkoxy and —S(O)₂R₂₈ₐ wherein R₂₈ₐ is loweralkyl or aryl;
(xiii) —CH₂OR₂₇ wherein R₂₇ is selected from hydrogen, loweralkyl and —C(O)R₂₈ wherein R₂₈ is hydrogen, loweralkyl or aryl;
(xiv) —CH₂NR₂₉R₃₀ wherein R₂₉ is selected from hydrogen, loweralkyl, —C(O)R₃₁, —C(O)NR₃₁R₃₂ and —S(O)₂R₃₃ wherein R₃₁ is selected from hydrogen, loweralkyl and aryl and R₃₃ is selected from loweralkyl and halo-substituted loweralkyl and wherein R₃₀ and R₃₂ are independently selected from hydrogen, loweralkyl, hydroxy and alkoxy;
(xv) —SO₃H, —OSO₃H or —CH₂SO₃H,
(xvi) —OPO₃H, —PO₃H₂ or —CH₂PO₃H₂,
(xvii) —SO₂NR₂₅R₂₆ or —CH₂SO₂NR₂₅R₂₆ wherein R₂₅ and R₂₆ are defined as above or
(xviii) —C(O)NHSO₂R₅₉, —C(O)NHC(O)R₅₉ or —C(O)NHNHSO₂R₅₉ wherein R₅₉ is loweralkyl, halo-substituted loweralkyl or aryl;

or a pharmaceutically acceptable salt or prodrug thereof.

4. The compound of claim 3 wherein A is a covalent bond, L, L', M, M' and $R_1'$ are hydrogen, —G—E— is —CH$_2$—N(R$_5$)— and $R_1$ is tetrazolyl.

5. A compound of the formula:

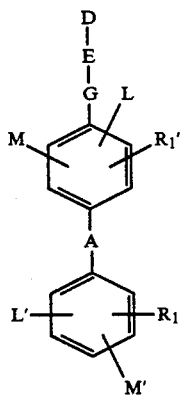

wherein
A is a covalent bond;
E—G is —N(R$_5$)—CH$_2$— wherein R$_5$ is hydrogen, loweralkyl, alkenyl, alkynyl, cycloalkyl or cycloalkylalkyl;
L, L', M and M' are independently selected from
  (i) hydrogen,
  (ii) loweralkyl,
  (iii) halo-substituted loweralkyl,
  (iv) halo,
  (v) —OH and
  (vi) alkoxy;
$R_1$ is tetrazolyl;
$R_1'$ is hydrogen; and
D is

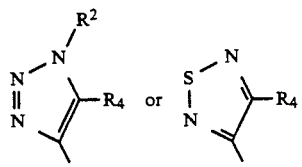

wherein $R_2$ is hydrogen or loweralkyl, and
$R_4$ is —COOR$_{24}$ wherein $R_{24}$ is hydrogen or a carboxy-protecting group; or a pharmaceutically acceptable salt or prodrug thereof.

6. A pharmaceutical composition for blocking the interaction of angiotensin II with angiotensin II receptors comprising a pharmaceutically acceptable carrier and a therapeutically effective amount of a compound of claim 1.

7. A method of blocking the interaction of angiotensin II with angiotensin II receptors comprising administering to a human or other mammal in need a therapeutically effective amount of a compound of claim 1.

8. A method of treating hypertension or congestive heart failure comprising administering to a human or other mammal in need a therapeutically effective amount of a compound of claim 1.

9. A compound of the formula:

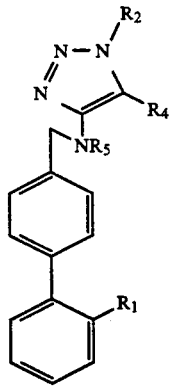

wherein $R_1$ is tetrazolyl; $R_2$ is hydrogen or loweralkyl; $R_4$ is —COOR$_{24}$ wherein $R_{24}$ is hydrogen or a carboxy-protecting group; and $R_5$ is hydrogen, loweralkyl, alkenyl, alkynyl, cycloalkyl or cycloalkylalkyl; or a pharmaceutically acceptable salt or prodrug thereof.

10. A compound of the formula:

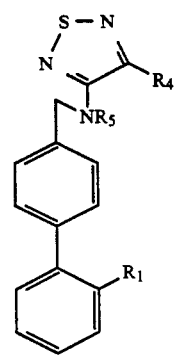

wherein $R_1$ is tetrazolyl; $R_4$ is —COOR$_{24}$ wherein $R_{24}$ is hydrogen or a carboxy-protecting group; and $R_5$ is hydrogen, loweralkyl, alkenyl, alkynyl, cycloalkyl or cycloalkylalkyl; or a pharmaceutically acceptable salt or prodrug thereof.

11. A compound selected from the group consisting of:
ethyl 4-{N-butyl-N-[(2'-[1H-tetrazol-5-yl]biphenyl-4-yl)methyl]amino}-1-methyl-2-(methylthio)imidazole-5-carboxylate;
ethyl 4-{N-butyl-N-[(2'-[1H-tetrazol-5-yl]biphenyl-4-yl)methyl]amino}-1-methylimidazole-5-carboxylate;
tert-butyl 4-{N-butyl-N-[(2'-[1H-tetrazol-5-yl]biphenyl-4-yl)methyl]amino}-1-(N-ethyl)imidazole-5-carboxylate;
4-{N-butyl-N-[(2'-[1H-tetrazol-5-yl]biphenyl-4-yl)methyl]amino}-1-(N-ethyl)imidazole;
ethyl 5-{N-butyl-N-[(2'-[1H-tetrazol-5-yl]biphenyl-4-yl)methyl]amino}-1-methylimidazole-4-carboxylate;
5-{N-butyl-N-[(2'-[1H-tetrazol-5-yl]biphenyl-4-yl)methyl]amino}-1-methylimidazole-4-carboxylic acid;
ethyl 5-{N-butyl-N-[(2'-[1H-tetrazol-5-yl]biphenyl-4-yl)methyl]amino}-1,2,3-thiadiazole-4-carboxylate;
5-[N-butyl-N-[[2'-(1H-tetrazol-5-yl)biphenyl-4-yl]methyl]amino]-1,2,3-thiadiazole-4-carboxylic acid;
ethyl 2-{N-butyl-N-[(2'-[1H-tetrazol-5-yl]biphenyl-4-yl)methyl]amino}-1,3,4-thiadiazole-5-carboxylate;
2-{N-butyl-N-[(2'-[1H-tetrazol-5-yl]biphenyl-4-yl)methyl]amino}-1,3,4-thiadiazole;

ethyl 1-methyl-3-{N-propyl-N-[(2'-[1H-tetrazol-5-yl]biphenyl-4-yl)methyl]amino}pyrazole-4-carboxylate;

1-methyl-3-{N-propyl-N-[(2'-[1H-tetrazol-5-yl]biphenyl-4-yl)methyl]amino}pyrazole-4-carboxylic acid;

ethyl 5-{N-butyl-N-[(2'-[1H-tetrazol-5-yl]biphenyl-4-yl)methyl]amino}-1-methylpyrazole-4-carboxylate;

5-{N-butyl-N-[(2'-[1H-tetrazol-5-yl]biphenyl-4-yl)methyl]amino}-1-(methyl)pyrazole-4-carboxylic acid;

4-{N-butyl-N-[(2'-[1H-tetrazol-5-yl]biphenyl-4-yl)methyl]amino}-1-methyl-1H-1,2,3-triazole-5-carboxylic acid;

4-{N-butyl-N-[(2'-[1H-tetrazol-5-yl]biphenyl-4-yl)methyl]amino}-1-isobutyl-1H-1,2,3-triazole-5-carboxylic acid;

1-n-butyl-4-{N-[(2'-[1H-tetrazol-5-yl]biphenyl-4-yl)methyl]amino}-1H-1,2,3-triazole-5-carboxylic acid; and 4-{N-propyl-N-[(2'-[1H-tetrazol-5-yl]biphenyl-4-yl)methyl]amino}-1,2,5-thiadiazole-4-carboxylic acid;

or a pharmaceutically acceptable salt or ester thereof.

12. A pharmaceutical composition for blocking the interaction of angiotensin II with angiotensin II receptors comprising a pharmaceutically acceptable carrier and a therapeutically effective amount of a compound of claim 3.

13. A method of blocking the interaction of angiotensin II with angiotensin II receptors comprising administering to a human or other mammal in need a therapeutically effective amount of a compound of claim 3.

14. A method of treating hypertension or congestive heart failure comprising administering to a human or other mammal in need a therapeutically effective amount of a compound of claim 3.

15. A pharmaceutical composition for blocking the interaction of angiotensin II with angiotensin II receptors comprising a pharmaceutically acceptable carrier and a therapeutically effective amount of a compound of claim 5.

16. A method of blocking the interaction of angiotensin II with angiotensin II receptors comprising administering to a human or other mammal in need a therapeutically effective amount of a compound of claim 5.

17. A method of treating hypertension or congestive heart failure comprising administering to a human or other mammal in need a therapeutically effective amount of a compound of claim 5.

18. A pharmaceutical composition for blocking the interaction of angiotensin II with angiotensin II receptors comprising a pharmaceutically acceptable carrier and a therapeutically effective amount of a compound of claim 9.

19. A method of blocking the interaction of angiotensin II with angiotensin II receptors comprising administering to a human or other mammal in need a therapeutically effective amount of a compound of claim 9.

20. A method of treating hypertension or congestive heart failure comprising administering to a human or other mammal in need a therapeutically effective amount of a compound of claim 9.

21. A pharmaceutical composition for blocking the interaction of angiotensin II with angiotensin II receptors comprising a pharmaceutically acceptable carrier and a therapeutically effective amount of a compound of claim 10.

22. A method of blocking the interaction of angiotensin II with angiotensin II receptors comprising administering to a human or other mammal in need a therapeutically effective amount of a compound of claim 10.

23. A method of treating hypertension or congestive heart failure comprising administering to a human or other mammal in need a therapeutically effective amount of a compound of claim 10.

24. A pharmaceutical composition for blocking the interaction of angiotensin II with angiotensin II receptors comprising a pharmaceutically acceptable carrier and a therapeutically effective amount of a compound of claim 11.

25. A method of blocking the interaction of angiotensin II with angiotensin II receptors comprising administering to a human or other mammal in need a therapeutically effective amount of a compound of claim 11.

26. A method of treating hypertension or congestive heart failure comprising administering to a human or other mammal in need a therapeutically effective amount of a compound of claim 11.

* * * * *

UNITED STATES PATENT AND TRADEMARK OFFICE
CERTIFICATE OF CORRECTION

PATENT NO. : 5,326,776
DATED : July 5, 1994
INVENTOR(S) : Diane M. Yamamoto; Anthony K. L. Fung; Martin Winn; Biswanath De; Thomas M. Zydowsky; Daniel J. Kerkman; John F. DeBernardis; Saul H. Rosenberg; Kazumi Shiosaki; Fatima Basha; Kenneth P. Spina; Thomas W. vonGeldern; Steven Boyd;

It is certified that error appears in the above-indentified patent and that said Letters Patent is hereby corrected as shown below:

COLUMN 89, LINE 62: Replace "$-CH_2NHS(I)_2R_{20}$"

with -- $-CH_2NHS(O)_2R_{20}$ --

COLUMN 92, LINE 54:

Replace "$-S(\ )_2R_{33}$"

with -- $-S(O)_2R_{33}$ --

Signed and Sealed this

Twenty-seventh Day of December, 1994

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 13 amino acid residues
( B ) TYPE: amino acid
( D ) TOPOLOGY: unknown ( i i ) MOLECULE TYPE:
( A ) DESCRIPTION:peptide ( v ) FRAGMENT TYPE:N-terminal fragment of angiotensinogen ( x i ) SEQUENCE DESCRIPTION: SEQ ID NO:1:

Asp Arg Val Tyr Ile His Pro Phe His Leu Val Ile His
                  5                       10

( 2 ) INFORMATION FOR SEQ ID NO:2:

( i ) SEQUENCE CHARACTERISTICS:
( A ) LENGTH: 10 amino acid residues
( B ) TYPE: amino acid
( D ) TOPOLOGY: unknown ( i i ) MOLECULE TYPE:
( A ) DESCRIPTION:peptide ( x i ) SEQUENCE DESCRIPTION: SEQ ID NO:2:

Asp Arg Val Tyr Ile His Pro Phe His Leu
                  5                       10

( 2 ) INFORMATION FOR SEQ ID NO:3:

( i ) SEQUENCE CHARACTERISTICS:
        ( A ) LENGTH: 8 amino acid residues
        ( B ) TYPE: amino acid
        ( D ) TOPOLOGY: unknown ( i i ) MOLECULE TYPE:
        ( A ) DESCRIPTION:peptide ( x i ) SEQUENCE DESCRIPTION: SEQ ID NO:3:

Asp Arg Val Tyr Ile His Pro Phe
                  5

( 2 ) INFORMATION FOR SEQ ID NO:4:

( i ) SEQUENCE CHARACTERISTICS:
        ( A ) LENGTH: 7 amino acid residues
        ( B ) TYPE: amino acid
        ( D ) TOPOLOGY: unknown ( i i ) MOLECULE TYPE:
        ( A ) DESCRIPTION:peptide ( x i ) SEQUENCE DESCRIPTION: SEQ ID NO:4:

Arg Val Tyr Ile His Pro Phe
              5